US012593986B2

(12) United States Patent
Zhang et al.

(10) Patent No.: US 12,593,986 B2
(45) Date of Patent: Apr. 7, 2026

(54) TRANSMISSION MODE-PHOTOACOUSTIC TOMOGRAPHY OF THE HUMAN BRAIN THROUGH AN ACOUSTIC WINDOW

(71) Applicant: California Institute of Technology, Pasadena, CA (US)

(72) Inventors: Yang Zhang, San Marino, CA (US); Sri Sai Narasimha KS Dhara Venkata, Pasadena, CA (US); Lihong Wang, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 18/633,290

(22) Filed: Apr. 11, 2024

(65) Prior Publication Data

US 2024/0341603 A1     Oct. 17, 2024

Related U.S. Application Data

(60) Provisional application No. 63/458,853, filed on Apr. 12, 2023.

(51) Int. Cl.
A61B 5/00 (2006.01)
G01N 21/17 (2006.01)

(52) U.S. Cl.
CPC .......... A61B 5/0095 (2013.01); A61B 5/4064 (2013.01); A61B 5/6814 (2013.01); A61B 5/6835 (2013.01); G01N 21/1702 (2013.01); A61B 2560/0462 (2013.01); A61B 2562/0233 (2013.01)

(58) Field of Classification Search
CPC .................................................... A61B 5/0095
See application file for complete search history.

(56) References Cited

U.S. PATENT DOCUMENTS

| | | | |
|---|---|---|---|
| 4,029,756 | A | 6/1977 | Gaafar |
| 4,127,318 | A | 11/1978 | Determann et al. |
| 4,255,971 | A | 3/1981 | Rosencwaig |
| 4,267,732 | A | 5/1981 | Quate |
| 4,284,324 | A | 8/1981 | Huignard et al. |
| 4,375,818 | A | 3/1983 | Suwaki et al. |
| 4,385,634 | A | 5/1983 | Bowen |
| 4,430,897 | A | 2/1984 | Quate |
| 4,430,987 | A | 2/1984 | Heller |
| 4,462,255 | A | 7/1984 | Guess et al. |
| 4,468,136 | A | 8/1984 | Murphy et al. |

(Continued)

FOREIGN PATENT DOCUMENTS

| | | |
|---|---|---|
| CN | 1883379 A | 12/2006 |
| CN | 106338473 A | 1/2017 |

(Continued)

OTHER PUBLICATIONS

Photoacoustic computed tomography for functional human brain imaging Biomedical optics, 2021.*

(Continued)

*Primary Examiner* — Joseph M Santos Rodriguez
(74) *Attorney, Agent, or Firm* — Sheila Martinez-Lemke; Kwan & Olynick LLP

(57) ABSTRACT

Photoacoustic imaging techniques that deliver diffuse light in transmission mode to the brain and detect acoustic waves transmitted through an acoustic window in the skull.

27 Claims, 16 Drawing Sheets

(56)                    References Cited

U.S. PATENT DOCUMENTS

| | | | |
|---|---|---|---|
| 4,489,727 A | 12/1984 | Matsuo et al. |
| 4,546,771 A | 10/1985 | Eggleton et al. |
| 4,596,254 A | 6/1986 | Adrian et al. |
| 4,687,304 A | 8/1987 | Piller et al. |
| 4,740,081 A | 4/1988 | Martens et al. |
| 4,802,461 A | 2/1989 | Cho |
| 4,802,487 A | 2/1989 | Martin et al. |
| 4,809,703 A | 3/1989 | Ishikawa et al. |
| 4,850,363 A | 7/1989 | Yanagawa |
| 4,860,758 A | 8/1989 | Yanagawa et al. |
| 4,869,256 A | 9/1989 | Kanno et al. |
| 4,872,758 A | 10/1989 | Miyazaki et al. |
| 4,921,333 A | 5/1990 | Brody et al. |
| 4,929,951 A | 5/1990 | Small |
| 4,995,396 A | 2/1991 | Inaba et al. |
| 5,070,455 A | 12/1991 | Singer et al. |
| 5,083,549 A | 1/1992 | Cho et al. |
| 5,107,844 A | 4/1992 | Kami et al. |
| 5,115,814 A | 5/1992 | Griffith et al. |
| 5,125,410 A | 6/1992 | Misono et al. |
| 5,140,463 A | 8/1992 | Yoo et al. |
| 5,170,793 A | 12/1992 | Takano et al. |
| 5,194,723 A | 3/1993 | Cates et al. |
| 5,207,672 A | 5/1993 | Roth et al. |
| 5,227,912 A | 7/1993 | Ho et al. |
| 5,305,759 A | 4/1994 | Kaneko et al. |
| 5,321,501 A | 6/1994 | Swanson et al. |
| 5,329,817 A | 7/1994 | Garlick et al. |
| 5,331,466 A | 7/1994 | Van Saarloos |
| 5,345,938 A | 9/1994 | Nishiki et al. |
| 5,373,845 A | 12/1994 | Gardineer et al. |
| 5,414,623 A | 5/1995 | Lu et al. |
| 5,445,155 A | 8/1995 | Sieben |
| 5,465,722 A | 11/1995 | Fort et al. |
| 5,546,187 A | 8/1996 | Pepper et al. |
| 5,546,947 A | 8/1996 | Yagami et al. |
| 5,546,948 A | 8/1996 | Hamm et al. |
| 5,606,975 A | 3/1997 | Liang et al. |
| 5,615,675 A | 4/1997 | O'Donnell et al. |
| 5,635,784 A | 6/1997 | Seale |
| 5,651,366 A | 7/1997 | Liang et al. |
| 5,713,356 A | 2/1998 | Kruger |
| 5,718,231 A | 2/1998 | Dewhurst et al. |
| 5,781,294 A | 7/1998 | Nakata et al. |
| 5,827,531 A | 10/1998 | Morrison |
| 5,836,872 A | 11/1998 | Kenet et al. |
| 5,840,023 A | 11/1998 | Oraevsky et al. |
| 5,860,934 A | 1/1999 | Sarvazyan |
| 5,913,234 A | 6/1999 | Julliard et al. |
| 5,971,998 A | 10/1999 | Russell et al. |
| 5,977,538 A | 11/1999 | Unger et al. |
| 5,991,697 A | 11/1999 | Nelson et al. |
| 6,055,097 A | 4/2000 | Lanni et al. |
| 6,102,857 A | 8/2000 | Kruger |
| 6,104,942 A | 8/2000 | Kruger |
| 6,108,576 A | 8/2000 | Alfano et al. |
| 6,111,645 A | 8/2000 | Tearney et al. |
| 6,134,003 A | 10/2000 | Tearney et al. |
| 6,216,025 B1 | 4/2001 | Kruger |
| 6,233,055 B1 | 5/2001 | Mandella et al. |
| 6,282,011 B1 | 8/2001 | Tearney et al. |
| 6,292,682 B1 | 9/2001 | Kruger |
| 6,309,352 B1 | 10/2001 | Oraevsky et al. |
| 6,341,036 B1 | 1/2002 | Tearney et al. |
| 6,379,325 B1 | 4/2002 | Benett et al. |
| 6,405,069 B1 | 6/2002 | Oraevsky et al. |
| 6,409,671 B1 | 6/2002 | Eriksen et al. |
| 6,413,228 B1 | 7/2002 | Hung et al. |
| 6,421,164 B2 | 7/2002 | Tearney et al. |
| 6,432,067 B1 | 8/2002 | Martin et al. |
| 6,466,806 B1 | 10/2002 | Geva et al. |
| 6,485,413 B1 | 11/2002 | Boppart et al. |
| 6,490,470 B1 | 12/2002 | Kruger |
| 6,498,942 B1 | 12/2002 | Esenaliev et al. |
| 6,498,945 B1 | 12/2002 | Alfheim et al. |
| 6,501,551 B1 | 12/2002 | Tearney et al. |
| 6,545,264 B1 | 4/2003 | Stern |
| 6,564,087 B1 | 5/2003 | Pitris et al. |
| 6,567,688 B1 | 5/2003 | Wang |
| 6,590,830 B1 | 7/2003 | Garlick et al. |
| 6,626,834 B2 | 9/2003 | Dunne et al. |
| 6,628,404 B1 | 9/2003 | Kelley et al. |
| 6,633,774 B2 | 10/2003 | Kruger |
| 6,654,630 B2 | 11/2003 | Zuluaga et al. |
| 6,658,279 B2 | 12/2003 | Swanson et al. |
| 6,694,173 B1 | 2/2004 | Bende et al. |
| 6,701,181 B2 | 3/2004 | Tang et al. |
| 6,751,490 B2 | 6/2004 | Esenaliev et al. |
| 6,764,450 B2 | 7/2004 | Yock |
| 6,831,781 B2 | 12/2004 | Tearney et al. |
| 6,833,540 B2 | 12/2004 | MacKenzie et al. |
| 6,839,496 B1 | 1/2005 | Mills et al. |
| 6,846,288 B2 | 1/2005 | Nagar et al. |
| 6,853,446 B1 | 2/2005 | Almogy et al. |
| 6,877,894 B2 | 4/2005 | Vona et al. |
| 6,937,886 B2 | 8/2005 | Zavislan |
| 6,956,650 B2 | 10/2005 | Boas et al. |
| 7,072,045 B2 | 7/2006 | Chen et al. |
| 7,198,778 B2 | 4/2007 | Achilefu et al. |
| 7,231,243 B2 | 6/2007 | Tearney et al. |
| 7,245,789 B2 | 7/2007 | Bates et al. |
| 7,266,407 B2 | 9/2007 | Li et al. |
| 7,322,972 B2 | 1/2008 | Viator et al. |
| 7,357,029 B2 | 4/2008 | Falk |
| 7,382,949 B2 | 6/2008 | Bouma et al. |
| 7,541,602 B2 | 6/2009 | Metzger et al. |
| 7,610,080 B1 | 10/2009 | Winchester, Jr. et al. |
| 7,917,312 B2 | 3/2011 | Wang et al. |
| 8,016,419 B2 | 9/2011 | Zhang et al. |
| 8,025,406 B2 | 9/2011 | Zhang et al. |
| 8,143,605 B2 | 3/2012 | Metzger et al. |
| 8,397,573 B2 | 3/2013 | Kobayashi |
| 8,416,421 B2 | 4/2013 | Wang et al. |
| 8,454,512 B2 | 6/2013 | Wang et al. |
| 8,891,088 B2 | 11/2014 | Goldschmidt et al. |
| 8,997,572 B2 | 4/2015 | Wang et al. |
| 9,086,365 B2 | 7/2015 | Wang et al. |
| 9,096,365 B2 | 8/2015 | Kim |
| 9,220,415 B2 | 12/2015 | Mandelis et al. |
| 9,226,666 B2 | 1/2016 | Wang et al. |
| 9,234,841 B2 | 1/2016 | Wang et al. |
| 9,335,605 B2 | 5/2016 | Wang et al. |
| 9,528,966 B2 | 12/2016 | Wang et al. |
| 9,554,738 B1 | 1/2017 | Gulati et al. |
| 9,618,445 B2 | 4/2017 | Sun et al. |
| 10,285,595 B2 | 5/2019 | Zalev et al. |
| 10,359,400 B2 | 7/2019 | Wang et al. |
| 10,433,733 B2 | 10/2019 | Wang et al. |
| 10,448,850 B2 | 10/2019 | Wang et al. |
| 10,666,928 B2 | 5/2020 | Liu |
| 11,020,006 B2 | 6/2021 | Wang et al. |
| 11,029,287 B2 | 6/2021 | Wang et al. |
| 11,135,375 B2 | 10/2021 | Brady et al. |
| 11,137,375 B2 | 10/2021 | Wang et al. |
| 11,369,280 B2 | 6/2022 | Wang et al. |
| 11,530,979 B2 | 12/2022 | Wang et al. |
| 11,592,652 B2 | 2/2023 | Wang et al. |
| 11,672,426 B2 | 6/2023 | Wang et al. |
| 11,986,269 B2 | 5/2024 | Wang et al. |
| 12,050,201 B2 | 7/2024 | Wang et al. |
| 12,182,940 B2 | 12/2024 | Li |
| 12,408,839 B2 | 9/2025 | Wang |
| 2001/0052979 A1 | 12/2001 | Treado et al. |
| 2002/0093637 A1 | 7/2002 | Yuan et al. |
| 2002/0173780 A1 | 11/2002 | Altshuler et al. |
| 2002/0176092 A1 | 11/2002 | Deck |
| 2003/0097066 A1 | 5/2003 | Shelby et al. |
| 2003/0160957 A1 | 8/2003 | Oldham et al. |
| 2003/0160967 A1 | 8/2003 | Houston et al. |
| 2004/0030255 A1 | 2/2004 | Alfano et al. |
| 2004/0039379 A1 | 2/2004 | Viator et al. |
| 2004/0082070 A1 | 4/2004 | Jones et al. |
| 2004/0111023 A1 | 6/2004 | Edic |
| 2004/0254474 A1 | 12/2004 | Seibel et al. |

(56) References Cited

U.S. PATENT DOCUMENTS

| | | |
|---|---|---|
| 2005/0015002 A1 | 1/2005 | Dixon et al. |
| 2005/0028482 A1 | 2/2005 | Cable et al. |
| 2005/0085725 A1 | 4/2005 | Nagar et al. |
| 2005/0143664 A1 | 6/2005 | Chen et al. |
| 2005/0154313 A1 | 7/2005 | Desilets et al. |
| 2005/0168749 A1 | 8/2005 | Ye et al. |
| 2005/0217381 A1 | 10/2005 | Falk |
| 2005/0234315 A1 | 10/2005 | Mayevsky et al. |
| 2005/0277824 A1 | 12/2005 | Aubry et al. |
| 2006/0055936 A1 | 3/2006 | Yun et al. |
| 2006/0058614 A1 | 3/2006 | Tsujita |
| 2006/0078196 A1 | 4/2006 | Sumanaweera et al. |
| 2006/0122516 A1 | 6/2006 | Schmidt et al. |
| 2006/0181791 A1 | 8/2006 | Van Beek et al. |
| 2006/0184042 A1 | 8/2006 | Wang et al. |
| 2006/0235299 A1 | 10/2006 | Martinelli |
| 2006/0247510 A1 | 11/2006 | Wiemker et al. |
| 2006/0264717 A1 | 11/2006 | Pesach et al. |
| 2007/0075063 A1 | 4/2007 | Wilbanks et al. |
| 2007/0088206 A1 | 4/2007 | Peyman et al. |
| 2007/0093702 A1 | 4/2007 | Yu et al. |
| 2007/0213590 A1 | 9/2007 | Squicciarini |
| 2007/0213618 A1 | 9/2007 | Li et al. |
| 2007/0213693 A1 | 9/2007 | Plunkett |
| 2007/0282200 A1 | 12/2007 | Johnson et al. |
| 2007/0299341 A1 | 12/2007 | Wang et al. |
| 2008/0029711 A1 | 2/2008 | Viellerobe et al. |
| 2008/0037367 A1 | 2/2008 | Gross et al. |
| 2008/0088838 A1 | 4/2008 | Raicu et al. |
| 2008/0123083 A1 | 5/2008 | Wang et al. |
| 2008/0173093 A1 | 7/2008 | Wang et al. |
| 2008/0230717 A1 | 9/2008 | Ashkenazi et al. |
| 2009/0051900 A1 | 2/2009 | Moon et al. |
| 2009/0054763 A1 | 2/2009 | Wang et al. |
| 2009/0088631 A1 | 4/2009 | Dietz et al. |
| 2009/0112096 A1 | 4/2009 | Tamura |
| 2009/0116518 A1 | 5/2009 | Patel et al. |
| 2009/0138215 A1 | 5/2009 | Wang et al. |
| 2009/0185191 A1 | 7/2009 | Boppart et al. |
| 2009/0227997 A1 | 9/2009 | Wang et al. |
| 2010/0053618 A1 | 3/2010 | Nakajima et al. |
| 2010/0079768 A1 | 4/2010 | Wang et al. |
| 2010/0134793 A1 | 6/2010 | Krishnamachari et al. |
| 2010/0151188 A1 | 6/2010 | Ishizuka |
| 2010/0245766 A1 | 9/2010 | Zhang et al. |
| 2010/0245769 A1 | 9/2010 | Zhang et al. |
| 2010/0245770 A1 | 9/2010 | Zhang et al. |
| 2010/0249562 A1 | 9/2010 | Zhang et al. |
| 2010/0268042 A1 | 10/2010 | Wang et al. |
| 2010/0285518 A1 | 11/2010 | Viator et al. |
| 2010/0309466 A1 | 12/2010 | Lucassen et al. |
| 2010/0322497 A1 | 12/2010 | Dempsey et al. |
| 2011/0014297 A1 | 1/2011 | Lee |
| 2011/0071402 A1 | 3/2011 | Masumura |
| 2011/0077526 A1 | 3/2011 | Zwirn |
| 2011/0122416 A1 | 5/2011 | Yang et al. |
| 2011/0201914 A1 | 8/2011 | Wang et al. |
| 2011/0251515 A1 | 10/2011 | Leuthardt et al. |
| 2011/0275890 A1 | 11/2011 | Wang et al. |
| 2011/0282181 A1 | 11/2011 | Wang et al. |
| 2011/0282192 A1 | 11/2011 | Axelrod et al. |
| 2012/0065490 A1 | 3/2012 | Zharov et al. |
| 2012/0070817 A1 | 3/2012 | Wang et al. |
| 2012/0074294 A1 | 3/2012 | Streuber et al. |
| 2012/0118052 A1 | 5/2012 | O'Donnell et al. |
| 2012/0204648 A1 | 8/2012 | Wang et al. |
| 2012/0275262 A1 | 11/2012 | Song et al. |
| 2012/0307250 A1 | 12/2012 | Wang et al. |
| 2013/0151188 A1 | 6/2013 | Rokni et al. |
| 2013/0199299 A1 | 8/2013 | Wang et al. |
| 2013/0218002 A1 | 8/2013 | Kiraly |
| 2013/0245406 A1 | 9/2013 | Wang et al. |
| 2013/0296684 A1 | 11/2013 | Miller |
| 2013/0338501 A1 | 12/2013 | Clingman |
| 2014/0009808 A1 | 1/2014 | Wang et al. |
| 2014/0029829 A1 | 1/2014 | Jiang et al. |
| 2014/0142404 A1 | 5/2014 | Wang et al. |
| 2014/0257079 A1 | 9/2014 | Irisawa |
| 2014/0356897 A1 | 12/2014 | Wang et al. |
| 2015/0005613 A1 | 1/2015 | Kim et al. |
| 2015/0105672 A1 | 4/2015 | Ishikawa et al. |
| 2015/0178959 A1 | 6/2015 | Huang et al. |
| 2015/0185187 A1 | 7/2015 | Wang et al. |
| 2015/0245771 A1 | 9/2015 | Wang et al. |
| 2015/0272444 A1 | 10/2015 | Maslov et al. |
| 2015/0272446 A1 | 10/2015 | Wang et al. |
| 2015/0297176 A1 | 10/2015 | Rincker et al. |
| 2015/0316510 A1 | 11/2015 | Fukushima et al. |
| 2016/0081558 A1 | 3/2016 | Wang et al. |
| 2016/0235305 A1 | 8/2016 | Wang et al. |
| 2016/0242651 A1 | 8/2016 | Wang et al. |
| 2016/0249812 A1 | 9/2016 | Wang et al. |
| 2016/0262628 A1 | 9/2016 | Wang et al. |
| 2016/0305914 A1 | 10/2016 | Wang et al. |
| 2016/0310083 A1 | 10/2016 | Wang et al. |
| 2016/0345886 A1 | 12/2016 | Wang et al. |
| 2016/0361042 A1 | 12/2016 | Razansky et al. |
| 2017/0065182 A1 | 3/2017 | Wang et al. |
| 2017/0105636 A1 | 4/2017 | Wang et al. |
| 2017/0367586 A9 | 12/2017 | Wang et al. |
| 2018/0020920 A1 | 1/2018 | Ermilov et al. |
| 2018/0088041 A1 | 3/2018 | Zhang et al. |
| 2018/0132728 A1 | 5/2018 | Wang et al. |
| 2018/0177407 A1 | 6/2018 | Hashimoto et al. |
| 2019/0008444 A1 | 1/2019 | Wang et al. |
| 2019/0008484 A1 | 1/2019 | Irisawa et al. |
| 2019/0125583 A1 | 5/2019 | Wang et al. |
| 2019/0227038 A1 | 7/2019 | Wang et al. |
| 2019/0298304 A1 | 10/2019 | Igarashi et al. |
| 2019/0307334 A1 | 10/2019 | Wang et al. |
| 2019/0343758 A1 | 11/2019 | Wang et al. |
| 2019/0365355 A1 | 12/2019 | Eldar et al. |
| 2020/0056986 A1 | 2/2020 | Wang et al. |
| 2020/0073103 A1 | 3/2020 | Wang et al. |
| 2020/0268253 A1 | 8/2020 | Wang et al. |
| 2020/0275846 A1 | 9/2020 | Wang et al. |
| 2020/0397523 A1 | 12/2020 | Gao et al. |
| 2021/0010976 A1 | 1/2021 | Wang et al. |
| 2021/0022702 A1 | 1/2021 | Yoshikawa |
| 2021/0132005 A1 | 5/2021 | Wang et al. |
| 2021/0145399 A1 | 5/2021 | Xie et al. |
| 2021/0321874 A1 | 10/2021 | Wang et al. |
| 2021/0333241 A1 | 10/2021 | Wang et al. |
| 2022/0237783 A1 | 7/2022 | Wong |
| 2023/0055979 A1 | 2/2023 | Wang et al. |
| 2023/0404407 A1 | 12/2023 | Garrett et al. |
| 2023/0404520 A1 | 12/2023 | Zhang et al. |
| 2024/0020955 A1 | 1/2024 | Frick |
| 2024/0065555 A1 | 2/2024 | Hu |
| 2024/0241239 A1 | 7/2024 | Wang et al. |
| 2024/0386629 A1 | 11/2024 | Hu |

FOREIGN PATENT DOCUMENTS

| | | |
|---|---|---|
| EP | 0012262 A1 | 6/1980 |
| EP | 0919180 A1 | 6/1999 |
| EP | 1227525 A2 | 7/2002 |
| EP | 1493380 A1 | 1/2005 |
| EP | 2749208 A1 | 7/2014 |
| EP | 3521808 A1 | 8/2019 |
| JP | H05126725 A | 5/1993 |
| JP | 2000292416 A | 10/2000 |
| JP | 4060615 B2 | 3/2008 |
| JP | 2009068977 A | 4/2009 |
| JP | 2010017426 A | 1/2010 |
| JP | 2010040161 A | 2/2010 |
| JP | 2012143384 A | 8/2012 |
| JP | 2013244122 A | 12/2013 |
| JP | 2014124242 A | 7/2014 |
| JP | 2014224806 A | 12/2014 |
| JP | 2016101260 A | 6/2016 |
| JP | 6086718 B2 | 3/2017 |
| JP | 6390516 B2 | 9/2018 |
| KR | 100946550 B1 | 3/2010 |

(56) References Cited

FOREIGN PATENT DOCUMENTS

| KR | 20160091059 A | 8/2016 |
| KR | 20170006470 A | 1/2017 |
| WO | WO-9633656 A1 | 10/1996 |
| WO | WO-2006111929 A1 | 10/2006 |
| WO | WO-2007088709 A1 | 8/2007 |
| WO | WO-2007148239 A2 | 12/2007 |
| WO | WO-2008062354 A1 | 5/2008 |
| WO | WO-2008100386 A2 | 8/2008 |
| WO | WO-2009055705 A2 | 4/2009 |
| WO | WO-2009154298 A1 | 12/2009 |
| WO | WO-2010048258 A1 | 4/2010 |
| WO | WO-2010080991 A2 | 7/2010 |
| WO | WO-2011060101 A2 | 5/2011 |
| WO | WO-2011091360 A2 | 7/2011 |
| WO | WO-2011127428 A2 | 10/2011 |
| WO | WO-2012035472 A1 | 3/2012 |
| WO | WO-2012133295 A1 | 10/2012 |
| WO | WO-2013086293 A1 | 6/2013 |
| WO | WO-2015118881 A1 | 8/2015 |
| WO | WO-2016081321 A2 | 5/2016 |
| WO | WO-2018102446 A2 | 6/2018 |
| WO | WO-2018102467 A1 | 6/2018 |
| WO | WO-2018116963 A1 | 6/2018 |
| WO | WO-2018209046 A1 | 11/2018 |
| WO | WO-2021067754 A1 | 4/2021 |

OTHER PUBLICATIONS

Abdelmohsen, et al., "Micro- and nano-motors for biomedical applications," J. Mater. Chem. B 2, (2014) pp. 2395-2408.

Al, et al., "Spectral-domain optical coherence tomography: Removal of autocorrelation using an optical switch," Applied Physics Letters, (Mar. 15, 2006), 88(11): pp. 111115-1-111115-3. doi:10.1063/1.2186520.

Allen, et al. "Pulsed Near-Infrared Laser Diode Excitation System for Biomedical Photoacoustic Imaging," Optics Letters, Optical Society of America, USA., vol. 31 , No. 23, Dec. 1, 2006, pp. 3462-3464.

Alomair, et al., "In vivo high angular resolution diffusion-weighted imaging of mouse brain at 16.4 Tesla," PloS One 10, Jun. 25, 2015, e0130133, pp. 1-17.

Amendment and Request for Continued Examination dated Nov. 25, 2019 in U.S. Appl. No. 14/436,581.

Arridge, et al., "Accelerated high-resolution photoacoustic tomography via compressed sensing," ArXiv Prepr. ArXiv160500133, 2016, pp. 8908-8940.

Aubry J.F., et al., "Experimental demonstration of noninvasive transskull adaptive focusing based on prior computed tomography scans," J. Acoust. Soc. Am. 113(1), 84-93 (2003).

Baheiraei, et al., "Investigation of magnesium incorporation within gelatin/calcium phosphate nanocomposite scaffold for bone tissue engineering," Int. J. Appl. Ceram. Technol. 12, (2015) pp. 245-253.

Baker, M. J. et al., "Using Fourier transform IR spectroscopy to analyze biological materials," Nat. Protoc. 9, 1771-1791 (2014).

Bansil, et al., "The biology of mucus: Composition, synthesis and organization" Adv. Drug Deliv. Rev. 124, (2018) pp. 3-15.

Beaven, G. H. & Holiday, E. R., "Ultraviolet absorption spectra of proteins and amino acids," Adv. Protein Chem 7, 319-386 (1952).

Beck A., et al., "A Fast Iterative Shrinkage-Thresholding Algorithm for Linear Inverse Problems" (2009) Siam J. Imaging Sciences, vol. 2, No. 1, pp. 183-202.

Bee-Dimmer, L., et al., "The Epidemiology of Chronic Venous Insufficiency and Varicose Veins," Annals of epidemiology, 2005, vol. 15(3), pp. 175-184.

Bell, A.G., "On the Production and Reproduction of Sound by Light," American Journal of Sciences, Oct. 1880, pp. 305-324, Third Series, vol. XX, USA.

Bellinger, et al., "Oral, ultra-long-lasting drug delivery: Application toward malaria elimination goals" Sci Transl. Med. 8(365), Nov. 16, 2016, 365ra157, pp. 1-25. doi:10.1126/scitranslmed.aag2374.

Bioucas-Dias, J.M. and Figueiredo, M.A.T. "A new TwIST: two-step iterative shrinkage/thresholding algorithms for image restoration," IEEE Trans. Image Process. 16, 2992-3004 (Dec. 2007).

Boas, D. A. and Dunn, A. K., "Laser speckle contrast imaging in biomedical optics," Journal of Biomedical Optics, (Jan./Feb. 2010), vol. 15, No. 1, p. 011109, 12 pages.

Brenner, et al., "Computed Tomography—An Increasing Source of Radiation Exposure" N. Engl. J. Med 357;22, Nov. 29, 2007, pp. 2277-2284.

Brunker, J., et al., "Velocity Measurements in Whole Blood Using Acoustic Resolution Photoacoustic Doppler," Biomedical Optics Express, 2016, vol. 7(7), 18 Pages.

Calasso et al., "Photoacoustic Point Source," Physical Review Letters, vol. 86, No. 16, Apr. 16, 2001, pp. 3550-3553.

Cannata et al., "Development of a 35-MHz Piezo-Composite Ultrasound Array for Medical Imaging," IEE Transactions on Ultrasonics, Ferroelectrics, and Frequency Control, 53(1): pp. 224-236 (2006).

Celli, J. P., et al., "Helicobacter pylori moves through mucus by reducing mucin viscoelasticity," Proc. Natl. Acad. Sci. U. S. A. 106, (2009) pp. 14321-14326.

Chan, et al., "New opportunities in micro- and macro-attenuated total reflection infrared spectroscopic imaging: spatial resolution and sampling versatility," Appl. Spectrosc. 57, 381-389 (2003).

Cheng, J.-X. Et al., "Vibrational spectroscopic imaging ofliving systems: an emerging platform for biology and medicine," Science, vol. 350 aaa8870, No. 6264, Nov. 27, 2015, pp. 1054-1063.

Cheong, et al., "A review of the optical properties of biological tissues," IEEE J. Quantum Electronics, 26(12): pp. 2166-2185 (1980).

Chourasia, et al., "Design and Development of Multiparticulate System for Targeted Drug Delivery to Colon," Drug Delivery, 11:3, (2004) pp. 201-207.

Cinotti, E., et al., "Quantification of Capillary Blood Cell Flow Using Reflectance Confocal Microscopy," Skin Research and Technology, 2014, vol. 20, pp. 373-378.

Cox, B., Beard, P., "Photoacoustic tomography with a single detector in a reverberant cavity" J. Acoust. Soc. Am. 125, 1426 (Mar. 2009).

Cox, et al., "Artifact trapping during time reversal photoacoustic imaging for acoustically heterogeneous media," IEEE Trans. Med. Imaging, vol. 29, No. 2, (2010) pp. 387-396.

Cui, Y., et al. "Transferring-conjugated magnetic silica PLGA nanoparticles loaded with doxorubicin and paclitaxel for brain glioma treatment," Biomaterials 34, (2013) pp. 8511-8520.

D'Andrea, et al., "Time-resolved optical imaging through turbid media using a fast data acquisition system based on a gated CCD camera" Journal of Physics D: Applied Physics, vol. 36, No. 14, Jul. 1, 2003, pp. 1675-1681.

Danielli, et al., "Label-free photoacoustic nanoscopy," Journal of Biomedical Optics, vol. 19, No. 8, Aug. 2014, pp. 086006-1-086006-10.

Darvas, F., et al., "Mapping Human Brain Function With Meg and Eeg: Methods and Validation," NeuroImage, 2004, vol. 23, pp. S289-S299.

Dazzi, A. et al., "AFM-IR: technology and applications in nanoscale infrared spectroscopy and chemical imaging," Chem. Rev. 117, 5146-5173 (2017).

Dazzi, A., et al., "Local infrared microspectroscopy with subwavelength spatial resolution with an atomic force microscope tip used as a photothermal sensor," Optics Letters, vol. 30, No. 18, Sep. 15, 2005, pp. 2388-2390.

De Avila, et al., "Micromotor-enabled active drug delivery for in vivo treatment of stomach infection" Nat. Commun. 8: 272, (2017) pp. 1-9.

De Boer, et al., "Improved signal-to-noise ratio in spectral-domain compared with time-domain optical coherence tomography" Optics Letters, vol. 28, No. 21, Nov. 1, 2003, pp. 2067-2069.

De Zerda, et al., "Family of enhanced photoacoustic imaging agents for high-sensitivity and multiplexing studies in living mice," ACS Nano 6(6), Jun. 26, 2012, pp. 4694-4701.

(56)                    References Cited

OTHER PUBLICATIONS

Demene, C. et al., Spatiotemporal clutter filtering of ultrafast ultrasound data highly increases Doppler and fUltrasound sensitivity, IEEE transactions on medical imaging, (Apr. 30, 2015), 34(11):2271-85.

Demene, C., et al., "Transcranial Ultrafast Ultrasound Localization Microscopy of Brain Vasculature in Patients," Nature biomedical engineering, 2021, vol. 5(3), pp. 219-228.

Deán-Ben, et al., "Functional optoacoustic neuro-tomography for scalable whole-brain monitoring of calcium indicators," Light Sci. Appl., vol. 5, No. 12, p. e16201, 2016, pp. 1-7.

Deán-Ben, et al., "Portable spherical array probe for volumetric real-time optoacoustic imaging at centimeter-scale depths," Opt. Express, vol. 21, No. 23, 2013, pp. 28062-28071.

Deserno, M., "How to generate equidistributed points on the surface of a sphere," Polym. Ed, p. 99, 2004, p. 1.

Diebold, et al., "Photoacoustic Monopole Radiation in One, Two and Three Dimensions," Physical Review Letters, Figs. 1 and 2, vol. 67, No. 24, Dec. 9, 1991 , pp. 3384-3387.

Diebold, et al., "Photoacoustic Signature of Particulate Matter: Optical Production of 9 Acoustic Monopole Radiation," Science New Series, Oct. 5, 1990, pp. 101-104, vol. 250, No. 4977, pp. 101-104.

Diem, M., et al., "A decade of vibrational micro-spectroscopy of human cells and tissue (1994-2004)†," Analyst, Oct. 2004, vol. 129, No. 10, pp. 880-885. doi:10.1039/b408952a.

Diem, M. et al., "Molecular pathology via IR and Raman spectral imaging." Journal of Biophotonics, vol. 6, No. 11-12 (2013) pp. 855-886. doi:10.1002/jbio.201300131.

Dong, J., et al., "Walled Vessel-mimicking Phantom for Ultrasound Imaging Using 3d Printing With a Water-soluble Filament: Design Principle, Fluid-structure Interaction (Fsi) Simulation, and Experimental Validation," Physics in medicine and biology, 2020, vol. 65(8).

Draeger, C., Fink, M., "One-channel time reversal of elastic waves in a chaotic 2D-silicon cavity," Phys. Rev. Lett. 79, 407-410 (Jul. 21, 1997).

Duan, T. et al., "Hybrid Multi-wavelength Photoacoustic Imaging",40th Annual International Conference of the IEEE Engineering in Medicine and Biology Society (EMBC), Jul. 18, 2018, pp. 4804-4807.

Dunn, et al., "Transport-based image reconstruction in turbid media with small source-detector separations," Optics Letters, vol. 25, No. 24, Dec. 15, 2000, pp. 1777-1779.

Eggebrecht, A., et al., "Mapping Distributed Brain Function and Networks With Diffuse Optical Tomography," Nature photonics, 2014, vol. 8(6), pp. 448-454.

Eghtedari, et al., "High Sensitivity of In Vivo Detection of Gold Nanorods Using a Laser Optoacoustic Imaging System," Nano Letters, vol. 7, No. 7, 2007, pp. 1914-1918.

EP Office Action dated May 11, 2022, in Application No. EP19849860.2.

Ermilov et al., "Laser optoacoustic imaging system for detection of breast cancer," Journal of Biomedical Optics, vol. 14 No. 2, pp. 24007-024007-14 (2009).

Erpelding et al., "Sentinel Lymph Nodes in the Rat: Noninvasive Photoacoustic and US Imaging with a Clinical US System," Radiology, 256(1): 102-110 (2010).

Errico, C., et al., "Ultrafast Ultrasound Localization Microscopy for Deep Super-resolution Vascular Imaging," Nature, 2015, vol. 527(7579), pp. 499-502.

Evans, et al., "Coherent Anti-Stokes Raman Scattering Microscopy: Chemical Imaging for Biology and Medicine," Annual Review of Analytical Chemistry I, (2008), pp. 883-909.

Extended European Search Report dated Apr. 22, 2022, in Application No. 19849860.2.

Extended European search report dated May 23, 2022, in Application No. EP19857631.6.

Extended European Search Report from European Application Serial No. 08842292.8, dated Dec. 17, 2013 (8 pages).

Fan, et al., "Development of a Laser Photothermoacoustic Frequency-Swept System for Subsurface Imaging: Theory and Experiment," J. Acoust. Soc. Am., vol. 116 (6), Dec. 2004, pp. 3523-3533.

Fan, et al., "Sub-Cellular Resolution Delivery of a Cytokine via Precisely Manipulated Nanowires" Nat. Nanotechnol. 5(7), Jul. 2010, 545-551. doi:10.1038/nnano.2010.104.

Fang, et al., "Photoacoustic Doppler effect from flowing small light-absorbing particles," Physical Review Letters 99(18) 184501-(1-4) (Nov. 2, 2007).

Farneback, G., et al., "Two-frame motion estimation based on polynomial expansion, in Scandinavian conference on Image analysis," 2003, pp. 363-370.

Fatima A., et al., "Review of Cost Reduction Methods in Photoacoustic Computed Tomography", Photoacoustics, 2019, vol. 15(100137), pp. 1-12.

Fercher, et al., "Measurement of Intraocular Distances by Backscattering Spectral Interferometry," Optics Communications, 1995, vol. 117, pp. 43-48.

Fernandez, D. C., Bhargava, R., Hewitt, S. M. & Levin, I. W., "Infrared spectroscopic imaging for histopathologic recognition," Nat. Biotechnol. 23, 469-474 (2005).

Fernandez-Colino, A., et al., "Advances in Engineering Venous Valves: The Pursuit of a Definite Solution for Chronic Venous Disease," Tissue engineering. Part B, Reviews, 2021, vol. 27(3), pp. 253-265.

Final Office Action dated Mar. 3, 2016 issued in U.S. Appl. No. 13/125,522.

Final Office Action dated May 24, 2019 issued in U.S. Appl. No. 14/436,581.

Final Office Action dated Nov. 15, 2017 issued in U.S. Appl. No. 14/639,676.

Final Office Action dated Sep. 24, 2018, from U.S. Appl. No. 15/148,685.

Final Office Action dated Sep. 30, 2015, from U.S. Appl. No. 14/026,577.

Final Office Action from related Japanese Patent Application No. JP 2010-531281, dated Mar. 11, 2014, (5 pages).

Final Office Action from related U.S. Appl. No. 11/625,099, dated Apr. 20, 2010.

Final Office Action from related U.S. Appl. No. 12/568,069, dated Sep. 18, 2012.

Final Office Action from related U.S. Appl. No. 13/125,522, dated May 23, 2013.

Final Office Action from related U.S. Appl. No. 13/125,522, dated Oct. 29, 2014.

Final Office Action from related U.S. Appl. No. 13/450,793, dated Nov. 22, 2013.

Final Office Action from related U.S. Appl. No. 13/574,994, dated Aug. 26, 2014.

Foster, et al., "Advances in ultrasound biomicroscopy" Ultrasound in Medicine & Biology, vol. 26, No. 1, Jan. 2000, pp. 1-27.

Fujita, K., et al., "Confocal multipoint multiphoton excitation microscope with microlens and pinhole arrays," Opt. Comm. 174, 7-12 (Jan. 15, 2000).

Furstenberg, et. al., "Chemical Imaging using Infrared Photo-thermal Microspectroscopy," In Proceedings of SPIE Defense, Security, and Sensing (eds Druy, M.A. & Crocombe, R. A.) 837411 (SPIE, 2012).

Gaihre et al., "Gelatin-coated magnetic iron oxide nanoparticles as carrier system: Drug loading and in vitro drug release study," Int. J. Pharm. 365, (2009) pp. 180-189.

Gao, et al., "A review of snapshot multidimensional optical imaging: measuring photon tags in parallel" Phys Rep. 616, Feb. 29, 2016, pp. 1-37. doi:10.1016/j.physrep.2015.12.004.

Gao, et al., "Artificial micromotors in the mouse's stomach: A step toward in vivo use of synthetic motors," ACS Nano 9, (2015) pp. 117-123.

Gao, et al., "Single-shot compressed ultrafast photography at one hundred billion frames per second," Nature 516(7529) 74-77 (Dec. 4, 2014).

Gibson, et al., "Recent advances in diffuse optical imaging" Physics in Medicine and Biology 50, 2005, pp. RI-R43, Institute of Physics Publishing, UK.

(56) References Cited

OTHER PUBLICATIONS

Gong, L. et al., "Breaking the diffraction limit by saturation in stimulated-Raman-scattering microscopy: a theoretical study," Phys. Rev. A 90, 13818 (2014).

Griffiths, P., "Fourier transform infrared spectrometry," Science 21, 297-302 (1983).

Guggenheim, et al., "Ultrasensitive planoconcave optical microresonators for ultrasound sensing", Nat. Photon. 11, 714-721 (2017).

Guittet C, et al., "In vivo high-frequency ultrasonic characterization of human dermis" IEEE Transactions on Bio-medical Engineering. Jun. 1999;46(6):740-746. doi:10.1109/10.764950.

Guo, et al., "Calibration-free absolute quantification of optical absorption coefficients using acoustic spectra in three-dimensional photoacoustic microscopy of biological tissue" Opt Lett. 2010 ; 35(12): 2067-2069. doi:10.1364/OL.35.002067.

Guo, et al., "CsxWO3 nanorods coated with polyelectrolyte multilayers as a multifunctional nanomaterial for bimodal imaging-guided photothermal/photodynamic cancer treatment," Adv. Mater. 29, 1604157 (2017).

Guo, Z., et al., "On the Speckle-free Nature of Photoacoustic Tomography," Medical Physics, 2009, vol. 36(9), pp. 4084-4088.

Haas, J. et al., "Advances in Mid-Infrared Spectroscopy for Chemical Analysis," Annu. Rev. Anal. Chem. 9 (2016) pp. 45-68.

Hai, et al., "High-throughput, label-free, single-cell photoacoustic microscopy of intratumoral metabolic heterogeneity," Nature Biomedical Engineering 3(5) 381-391 (May 2019).

Hai, et al., "Near-infrared optical-resolution photoacoustic microscopy", Opt. Lett. 39, 5192-5195 (Sep. 1, 2014).

Han, et al., "Optoacoustic image reconstruction and system analysis for finite-aperture detectors under the wavelet-packet framework," J. Biomed. Opt., vol. 21, No. 1, Jan. 2016, pp. 016002-1-016002-9.

Han, Y. et al., "Three-dimensional optoacoustic reconstruction using fast sparse representation," Opt. Lett., vol. 42, No. 5, (2017) pp. 979-982.

Hebden et al., "Enhanced time-resolved imaging with a diffusion model of photon transport" Optics Letters, vol. 19, No. 5, 1994, pp. 311-313.

Hee, et al., "Femtosecond transillumination tomography in thick tissues" Optics Letters, vol. 18, No. 13, 1993, pp. 1107-1109.

Hillman, et al., "Laminar optical tomography: demonstration of millimeter-scale depth-resolved imaging in turbid media," Optics Letters, vol. 29, No. 14, Jul. 15, 2004, pp. 1650-1652.

Hindelang, et al., "Enabling Precision Monitoring of Psoriasis Treatment by Optoacoustic Mesoscopy," Science Translational Medicine, 2022, vol. 14(644).

Hoelen, et al., "Three Dimensional Photoacoustic Imaging of Blood Vessels in Tissue" Optics Letters, 1998, pp. 648-650, vol. 23, No. 8, Optical Society of America, USA.

Hong, et al., "Simple Method to Produce Janus Colloidal Particles in Large Quantity" Langmuir 22, (2006) pp. 9495-9499.

Hu, C., et al., "Soft Micro- and Nanorobotics," Annu. Rev. Control. Robot. Auton. Syst. 1, (2018) pp. 53-75.

Hu P et al., "Location-Dependent Spatiotemporal Antialiasing in Photoacoustic Computed Tomography," IEEE Transactions on Medical Imaging, Apr. 2023, vol. 42(4), pp. 1210-1224.

Hu, S., et al., "Label-free Photoacoustic Ophthalmic Angiography" Optics Letters, 35(1), Jan. 1, 2010, pp. 1-3.

Hu, S. et al., "Three-dimensional optical-resolution photoacoustic microscopy," Journal of Visualized Experiments 51 (2011).

Hu, W., et al., "Small-scale soft-bodied robot with multimodal locomotion," Nature 554, 81-85, (2018).

Huang, et al., "Aberration correction for transcranial photoacoustic tomography of primates employing adjunct image data," Journal of Biomedical Optics, vol. 17, No. 6, Jun. 2012, pp. 066016-1 to 066016-8.

Huang, et al., "Full-wave iterative image reconstruction in photoacoustic tomography with acoustically inhomogeneous media," IEEE Trans. Med. Imaging, vol. 32, No. 6, Jun. 2013, pp. 1097-1110.

Huang, et al., "Optical Coherence Tomography," Science, New Series, vol. 254, No. 5035, Nov. 22, 1991, pp. 1178-1181.

Huber, et al., "Three-Dimensional and C-Mode 6 OCT Imaging with a Compact, Frequency Swept Laser Source at 1300 nn" Optics Express, vol. 13, No. 26, Dec. 26, 2005, pp. 10523-10526.

Imai, T. et al., "High-throughput ultraviolet photoacoustic microscopy with multifocal excitation," Journal of Biomedical Optics 23(3), 036007 (Mar. 15, 2018).

Ing, R. K., Quieffin, N., Catheline, S., Fink, M., "In solid localization of finger impacts using acoustic time-reversal process," Appl. Phys. Lett. 87, 204104 (Nov. 14, 2005).

International Preliminary Report on Patentability dated Feb. 25, 2021, issued in Application No. PCT/US2019/046574.

International Preliminary Report on Patentability dated Jan. 6, 2022 in PCT Application No. PCT/US2020/070174.

International Preliminary Report on Patentability dated Mar. 18, 2021, issued in Application No. PCT/US2019/049594.

International Preliminary Report on Patentability dated May 19, 2022, in PCT Application No. PCT/US2020/059214.

International Preliminary Report on Patentability dated Nov. 12, 2019 issued in PCT/US2018/032007.

International Preliminary Report on Patentability dated Sep. 2, 2021, issued in Application No. PCT/US2020/019368.

International Search Report and Written Opinion dated Apr. 22, 2009, from Application No. PCT/US2008/081167 (7 pages).

International Search Report and Written Opinion dated Aug. 31, 2020, issued in Application No. PCT/US2020/019368.

International Search Report and Written Opinion dated Aug. 9, 2018 issued in Application No. PCT/US2018/032007.

International Search Report and Written Opinion dated Dec. 2, 2019, issued in Application No. PCT/US2019/046574.

International Search Report and Written Opinion dated Dec. 23, 2019, issued in Application No. PCT/US2019/049594.

International Search Report and Written Opinion dated Mar. 2, 2021 issued in PCT/US2020/059214.

International Search Report and Written Opinion dated May 9, 2024 in PCT Application No. PCT/US2024/011281.

International Search Report and Written Opinion dated Oct. 14, 2020, issued in Application No. PCT/US2020/070174.

International Search Report and Written Opinion from Application Serial No. PCTIUS2012/068403, dated Mar. 19, 2013 (10 pages).

International Search Report and Written Opinion from Application Serial No. PCT/US2010/020488, dated Aug. 31, 2010 (10 pages).

International Search Report and Written Opinion from Application Serial No. PCT/US2011/031823, dated Dec. 26, 2011 (8 pages).

International Search Report of International Application No. PCT/US2014/066437, Feb. 26, 2015, 3 pages.

Jaipan, P., et al., "Gelatin-based Hydrogels for Biomedical Applications," MRS Communications, 2017, vol. 7, pp. 416-426.https://doi.org/10.1557/mrc.2017.92.

Ji, M. et al., "Detection of human brain tumor infiltration with quantitative stimulated Raman scattering microscopy," Sci. Transl. Med 7, 309ra163 (2015).

Ji, T. et al. "Preparation, Characterization, and Application of Au-Shell/Polystyrene Beads and Au-hell/Magnetic Beads" Adv. Mater. 13(16), Aug. 2001, pp. 1253-1256.

Karamata, et al., "Multiple Scattering in Optical Coherence Tomography I Investigation and Modeling" Journal of Optical Society of America, vol. 22, No. 7 (2005) pp. 1369-1379.

Karamata, et al., "Multiple scattering in optical coherence tomography. II. Experimental and theoretical investigation of cross talk in wide-field optical coherence tomography" J. Opt. Soc. Am. A/vol. 22, No. 7/Jul. 2005, pp. 1380-1388.

Karshalev, E. et al., "Micromotor Pills as a Dynamic Oral Delivery Platform" American Chemical Society Nano, 2018, vol. 12, No. 8, pp. 8397-8405 DOI: 10.1021/acsnano.8b03760.

Keys, A., et al., "The Oxygen Saturation of the Venous Blood in Normal Human Subjects," American Journal of Physiology-Legacy Content, 1938, vol. 124(1), pp. 13-21.

Kim, C. et al., "In vivo molecular photoacoustic tomography of melanomas targeted by bio-conjugated gold nanocages" ACS Nano, 2010; 4(8), pp. 4559-4564. doi:10.1021/nn100736c.

Kinnunen, M., et al., "Effect of the Size and Shape of a Red Blood Cell on Elastic Light Scattering Properties at the Single-cell Level," Biomedical Optics Express, 2011, vol. 2(7), pp. 1-12.

(56)　　　　　References Cited

OTHER PUBLICATIONS

Kirch, J., et al., "Optical tweezers reveal relationship between microstructure and nanoparticle penetration of pulmonary mucus," Proc. Natl. Acad. Sci. 109, (2012) pp. 18355-18360.
Knoll, B. & Keilmann, F., "Near-field probing of vibrational absorption for chemical microscopy," Nature 399, 134-137 (1999).
Kole, M. R., et al., "Discrete frequency infrared microspectroscopy and imaging with a tunable quantum cascade laser," Anal. Chem. 84, 10366-10372 (2012).
Kolkman, et al., "In Vivo Photoacoustic Imaging of Blood Vessels Using an Extreme-Narrow Aperture Sensor" IEEE Journal of Selected Topics in Quantum Electronics, vol. 9, No. 2, Mar./Apr. 2003, pp. 343-346.
Kothapalli, S., et al., "Simultaneous Transrectal Ultrasound and Photoacoustic Human Prostate Imaging," Science Translational Medicine, 2019, vol. 11 (507), pp. 1-12.
Koziolek, et al., "Navigating the human gastrointestinal tract for oral drug delivery: Uncharted waters and new frontiers," Adv. Drug Delivery Rev. 101, (2016) pp. 75-88.
Kruger, et al., "Breast Cancer in Vivo: Contrast Enhancement with Thermoacoustic CT at 434 MHz-Feasibility Study," Radiology, 216(1): 279-283 (2000).
Kruger et al., "Photoacoustic Ultrasound (PAUS)-Reconstruction Tomography" Med. Phys., Oct. 1995, vol. 22 (10) Am. Assoc. Phys. Med., USA, pp. 1605-1609.
Kruger et al., "Thermoacoustic computed tomography using a conventional linear transducer array," Medical Physics, 30(5): 856-860 (2003).
Kruger, et al., "Thermoacoustic computed tomography-technical considerations" Medical Physics, 26(9): 1832-1837 (1999).
Kruger, et al., "Thermoacoustic CT: imaging principles," Proc. SPIE 3916, (2000) pp. 150-160.
Kruger, et al., "Thermoacoustic Molecular Imaging of Small Animals," Molecular Imaging, 2(2): 113-123 (2003).
Ku and Wang, "Scanning microwave-induced thermoacoustic tomography: Signal, resolution, and contrast," Medical Physics, 28(1): 4-10 (2001).
Ku and Wang, "Scanning thermoacoustic tomography in biological tissue." Medical physics 27.5 (2000): 1195-1202.
Ku and Wang, "Deeply penetrating photoacoustic tomography in biological tissues enhanced with an optical contrast agent," Optics Letters, 30(5): 507-509 (2005).
Ku, et al., "Imaging of tumor angiogenesis in rat brains in vivo by photoacoustic tomography," Applied Optics, 44(5): 770-775 (2005).
Ku, G. et al., "Multiple-bandwidth photoacoustic tomography," Physics in Medicine & Biology, 49(7): 1329-1338 (2004).
Ku G, et al., "Thermoacoustic and Photoacoustic Tomography of Thick Biological Tissues Toward Breast Imaging," Technology in Cancer Research & Treatment, 4(5): 559-566 (2005).
Kunitz, M., "Crystalline desoxyribonuclease; isolation and general properties; spectrophotometric method for the measurement of desoxyribonuclease activity," The Journal General Physiology, vol. 33, Mar. 20, 1950, pp. 349-362. URL: http://doi.org./10.1085/jgp.33.4.349.
Kuppusami, S. et al., "Parylene Coatings in Medical Devices and Implants: A Review" Universal Journal of Biomedical Engineering, 2015, vol. 3, No. 2, pp. 9-14 DOI: 10.13189/ujbe.2015.030201.
Lai, P. et al., "Dependence of optical scattering from Intralipid in gelatin-gel based tissue-mimicking phantoms on mixing temperature and time" Journal of Biomedical Optics, vol. 19, No. 3, Mar. 2014, pp. 035002-1-035002-6.
Lai, P. et al., "Photoacoustically guided wavefront shaping for enhanced optical focusing in scattering media," Nature Photonics 9 126-132 (Jan. 19, 2015).
Lai P., et al., "Time-reversed Ultrasonically Encoded Optical Focusing in Biological Tissue," Journal of Biomedical Optics, 2012, vol. 17 (3), pp. 1-4.
Lai, S. et al., "Mucus-penetrating nanoparticles for drug and gene delivery to mucosal tissues," Adv. Drug Deliv. Rev. 61(2), Feb. 27, 2009, pp. 158-171. doi:10.1016/j.addr.2008.11.002.

Larina, et al., Real-time optoacoustic monitoring of temperature in tissues: Journal of Physics D: Applied Physics, vol. 38, (2005) pp. 2633•—2639.
Lasch, et al., "FT-IR spectroscopic investigations of single cells on the subcellular level," Vibr. Spectrosc. 28, 147-157 (2002).
Laser Institute of America, "American National Standard for the safe use of lasers," American National Standard Institute (ANSI Z136.1-2007 Revision of ANSI Z136.1-2000).
Leal, et al., "Physicochemical properties of mucus and their impact on transmucosal drug delivery," Int. J. Pharm. 532, (2017) pp. 555-572.
Lee, Y., et al., "Automatic Dynamic Range Adjustment for Ultrasound B-mode Imaging," Ultrasonics, 2015, vol. 56, pp. 435-443.
Leitgeb, et al., "Performance of fourier domain vs. time domain optical coherence tomography," Optical Express, vol. 11, No. 8, Apr. 21, 2003, pp. 889-894.
Leitgeb, R., et al., "Doppler Optical Coherence Tomography," Progress in Retinal and Eye Research, 2014, vol. 41, pp. 26-43.
Lewis, E. N. et al., "Fourier transform spectroscopic imaging using an infrared focal-Plane array detector," Anal. Chem. 67, 3377-3381 (1995).
Li, et al., "An Enteric Micromotor Can Selectively Position and Spontaneously Propel in the Gastrointestinal Tract," ACS Nano. 10(10), Oct. 25, 2016, pp. 9536-9542. doi:10.1021/acsnano.6b04795.
Li, et al., "Autonomous Collision-Free Navigation of Microvehicles in Complex and Dynamically Changing Environments" ACS Nano, 11, (2017) pp. 9268-9275.
Li, et al., "Snapshot photoacoustic topography through an ergodic relay for high-throughput imaging of optical absorption," Nature Photonics 14(3) (2020) pp. 164-170. URL:https://doi.org/10.1038/s41566-019-0576-2.
Li, et al., "Optical Coherence Computed Tomography," Applied Physics Letters, vol. 91, American Institute of Physics, 2007, pp. 141107-1-141107-3.
Li., et al., Single-impulse Panoramic Photoacoustic Computed Tomography of Small-animal Whole-body Dynamics at High Spatiotemporal Resolution, Nature Biomedical Engineering. 1(5) May 2017, pp. 1-11. doi: 10.1038/s41551-017-0071.
Li, G. et al., "Reflection-mode Multifocal Optical-resolution Photoacoustic Microscopy," Journal of Biomedical Optics, Mar. 2013, vol. 18, No. 3, 030501 (4 pages).
Li, J. et al., "Micromotors Spontaneously Neutralize Gastric Acid for pH-Responsive Payload Release" Angewandte Chemie International Edition, vol. 56, No. 8, 2017, pp. 2156-2161. DOI: 10.1002/anie.201611774.
Li, J. et al., "Micro/Nanorobots for Biomedicine: Delivery, Surgery, Sensing, and Detoxification" Sci Robot, 2(4), Mar. 15, 2017, pp. 1-20. doi:10.1126/scirobotics.aam6431.
Li, L . . . , et al., "Simultaneous Molecular and Hypoxia Imaging of Brain Tumors in Vivo Using Spectroscopic Photoacoustic Tomography," Proceedings of the IEEE, 96(3): 481-489 (2008).
Li, L., et al., "Small near-infrared photochromic protein for photoacoustic multi-contrast imaging and detection of protein interactions in vivo," Nature Communications 9(1) 2734 (Jul. 16, 2018).
Li, Y. et al., "Multifocal photoacoustic microscopy through an ergodic relay (Conference Presentation)", Proc. SPIE 10878, Photons Plus Ultrasound: Imaging and Sensing 2019, 108781C, presented Feb. 4, 2019, published Mar. 4, 2019, https://doi.org/10.1117/12.2513502.
Li, Y. et al., "Multifocal Photoacoustic Microscopy Using a Single-element Ultrasonic Transducer Through an Ergodic Relay", Light: Science & Applications, Jul. 31, 2020, vol. 9, No. 135, pp. 1-7.
Li Z., et al., Broadband Gradient Impedance Matching Using an Acoustic Metamaterial for Ultrasonic Transducers, Scientific Reports, 2017, vol. 7(42863), pp. 1-9.
Li, Z., et al., "Super—resolution far-field infrared imaging by photothermal heterodyne imaging," The Journal of Physical Chemistry B, vol. 121 (2017) pp. 8838-8846.
Li, Z., et al., "Super-resolution imaging with mid-IR photothermal microscopy on the single particle level," In Proceedings of SPIE Physical Chemistry of Interfaces and Nano-materials XIV, vol. 9549, Aug. 20, 2015, pp. 954912-1-954912-8.

(56) References Cited

OTHER PUBLICATIONS

Liang, et al., "Single-shot real-time femtosecond imaging of temporal focusing," Light-Science & Applications 7(1) 42 (Aug. 8, 2018).

Liang, et al., "Single-shot real-time video recording of a photonic Mach cone induced by a scattered light pulse," Science Advances 3(1) e1601814 (Jan. 20, 2017).

Liang, et al., "Single-shot ultrafast optical imaging," Optica 5(9) 1113-1127 (Sep. 2018).

Lin, L., et al., "Single-breath-hold Photoacoustic Computed Tomography of the Breast," Nature communications, 2018, vol. 9(1), pp. 1-9.

Lin, L., et al., "The Emerging Role of Photoacoustic Imaging in Clinical Oncology," Nature reviews. Clinical oncology, 2022, vol. 19(6), pp. 365-384.

Liu, et al., "Label-free cell nuclear imaging by Grüneisen relaxation photoacoustic microscopy" Opt Lett. Feb. 15, 2018; 43(4), (2018) pp. 947-950.

Liu, et al., "Optical focusing deep inside dynamic scattering media with near-infrared time-reversed ultrasonically encoded (TRUE) light," Nature Communications 6 5409 (Jan. 5, 2015).

Logothetis, N., "What we can do and what we cannot do with fMRI," Nature, 2008, vol. 453(7197), pp. 869-878.

Lovell, et al., "Porphysome nanovesicles generated by porphyrin bilayers for use as multimodal biophotonic contrast agents," Nature Materials 10(4) 324-32 (Mar. 20, 2011).

Lu, F., et al., "Tip-enhanced infrared nanospectroscopy via molecular expansion force detection," Nat. Photon. 8, 307-312 (2014).

Lu, F.-K. et al., "Label-free DNA imaging in vivo with stimulated Raman scattering microscopy," Proc. Natl Acad Sci. USA 112, 11624-11629 (2015).

Lurie, F., et al., "Mechanism of Venous Valve Closure and Role of the Valve in Circulation: a New Concept," Journal of vascular surgery, 2003, vol. 38(5), pp. 955-961.

Ma, et al., "Time-reversed adapted-perturbation (TRAP) optical focusing onto dynamic objects inside scattering media," Nature Photonics 8(12) 931-936 (Nov. 2, 2014).

Manohar, et al., "Initial results of in vivo non-invasive cancer imaging in the human breast using near-infrared photoacoustics," Optics Express, 15(19): 12277-12285 (2007).

Maslov, et al., "In vivo dark-field reflection-mode photoacoustic microscopy," Optics Letters 30(6), Mar. 15, 2005, pp. 625-627.

Maslov, et al., "Optical-resolution photoacoustic microscropy for in vivo imaging of single capillaries," Optical Letters, 33(9): 929-931 (2008).

Maslov, et al., "Photoacoustic Imaging of biological tissue with Intensity-Modulated Continuous-Wave Laser" Journal of Biomedical Optics, 2008, pp. 024006 1-5, vol. 13(2), SPIE, USA.

Matsumoto, et al., "Label-free photoacoustic imaging of human palmar vessels: a structural morphological analysis," Sci. Rep., vol. 8, No. 1, (2018) p. 786.

Matthews, et al., "Parameterized Joint Reconstruction of the Initial Pressure and Sound Speed Distributions for Photoacoustic Computed Tomography," Siam J. Imaging Sci., vol. 11, No. 2, (2018) pp. 1560-1588.

Medina-Sanchez, et al., "Medical microbots need better imaging and control," Nature 545, (2017) pp. 406-408.

Michaelian, Kirk H. "Photoacoustic IR spectroscopy: instrumentation, applications and data analysis" John Wiley & Sons; Dec. 1, 2010. Preface Only.

Miller, et al., "Synchrotron-based biological microspectroscopy: From the mid-infrared through the far-infrared regimes," Journal of Biological Physics 29, 219-230 (2003).

Mishra et al., "Development and comparison of the DTM, the DOM and the FVM formulations for the short-pulse laser transport through a participating medium" International Journal of Heat and Mass Transfer, vol. 49 (2006) pp. 1820-1832.

Mitsuhashi, et al., "A forward-adjoint operator pair based on the elastic wave equation for use in transcranial photoacoustic computed tomography," Siam J. Imaging Sci., vol. 10, No. 4, 2017, pp. 2022-2048.

Mitsuhashi, et al., "Investigation of the far-field approximation for modeling a transducer's spatial impulse response in photoacoustic computed tomography," Photoacoustics, vol. 2, No. 1, 2014, pp. 21-32.

Montaldo, et al., "Building three-dimensional images using time-reversal chaotic cavity", IEEE Trans. Ultrason. Ferroelectr. Freq. Control 52, pp. 1489-1497 (2005).

Montaldo, et al., "Coherent Plane-Wave Compounding for Very High Frame Rate Ultrasonography and Transient Elastography," IEEE Trans. Ultrason. Ferroelectr. Freq. Control, vol. 56, No. 3, Mar. 2009, pp. 489-506.

Morgner et al., "Spectroscopic optical coherence tomography," Optics Letters, vol. 25, No. 2, Jan. 15, 2000, pp. 111-113.

Murray, C., et al., "The Physiological Principle of Minimum Work: I. The Vascular System and the Cost of Blood Volume," Proceedings of the National Academy of Sciences of the United States of America, 1926, vol. 12(3),pp. 207-214.

Murray et al., "High-Sensitivity Laser-Based Acoustic Microscopy Using a Modulated Excitation Source," Applied Physics Letters, vol. 85, No. 14, American Institute of Physics, USA., Oct. 4, 2004, pp. 2974-2976.

Na, S., et al., "Cross-ray Ultrasound Tomography and Photoacoustic Tomography of Cerebral Hemodynamics in Rodents," Advanced science, 2022, vol. 9(25).

Na, S., et al., "Massively Parallel Functional Photoacoustic Computed Tomography of the Human Brain," Nature Biomedical Engineering 2021, vol. 6(5), pp. 584-592.

Nakajima, et al., "Three-dimensional analysis and classification of arteries in the skin and subcutaneous adipofascial tissue by computer graphics imaging," Plastic and Reconstructive Surgery, 102(3): 748-760 (1998).

Nasiriavanaki, et al., "High-resolution photoacoustic tomography of resting-state functional connectivity in the mouse brain," Proceedings of the National Academy of Sciences 111(1) 21-26 (Jan. 7, 2014).

Nasse, M. J. et al., "High-resolution Fourier-transform infrared chemical imaging with multiple synchrotron beams," Nat. Methods 8, 413-416 (2011).

Nelson et al., "Imaging Glioblastoma Multiforme," The Cancer Journal vol. 9, No. 2, Mar./Apr. 2003, pp. 134-145.

Niederhauser et al., "Combined Ultrasound and Optoacoustic System for Real-Time High-Contrast Vascular imaging in Vivo," IEEE Transactions on MedicalImaging, 24(4): 436-440 (2005).

Notice of Allowance dated Dec. 12, 2018 issued in U.S. Appl. No. 14/639,676.

Notice of Allowance dated Dec. 5, 2014 issued in U.S. Appl. No. 13/369,558.

Notice of Allowance dated Feb. 2, 2021 issued in U.S. Appl. No. 16/372,597.

Notice of Allowance dated Jan. 26, 2021 issued in U.S. Appl. No. 14/436,581.

Notice of Allowance dated Jan. 5, 2016, from U.S. Appl. No. 14/026,577.

Notice of Allowance dated Jan. 5, 2022 issued in U.S. Appl. No. 16/540,936.

Notice of Allowance dated Jul. 29, 2014 issued in U.S. Appl. No. 13/369,558.

Notice of Allowance dated Jun. 23, 2021 issued in U.S. Appl. No. 15/037,468.

Notice of Allowance dated Mar. 23, 2020 issued in U.S. Appl. No. 15/037,468.

Notice of Allowance dated May 16, 2019, from U.S. Appl. No. 15/148,685.

Notice of Allowance dated Nov. 17, 2015 from U.S. Appl. No. 13/574,994.

Notice of Allowance dated Oct. 28, 2020 issued in U.S. Appl. No. 15/037,468.

Notice of Allowance dated Sep. 19, 2016 issued in U.S. Appl. No. 13/125,522.

(56)                    References Cited

OTHER PUBLICATIONS

Notice of Allowance from related U.S. Appl. No. 12/254,643, dated Nov. 22, 2010.
Notice of Allowance from related U.S. Appl. No. 12/568,069, dated Feb. 22, 2013.
Notice of Allowance from related U.S. Appl. No. 12/739,589, dated Feb. 5, 2013.
Nowak, D et al., "Nanoscale chemical imaging by photoinduced force microscopy," Sci. Adv. 2, Mar. 25, 2016, e1501571, pp. 1-9.
Ntziachristos, V., "Going deeper than microscopy: the optical imaging frontier in biology" Nature Methods vol. 7, No. 8, Aug. 2010, pp. 603-614.
Office Action dated Apr. 21, 2017 issued in U.S. Appl. No. 14/639,676.
Office Action dated Apr. 3, 2020 issued in U.S. Appl. No. 14/436,581.
Office Action dated Aug. 19, 2019 issued in U.S. Appl. No. 16/372,597.
Office Action dated Aug. 26, 2015 issued in U.S. Appl. No. 13/125,522.
Office Action dated Dec. 13, 2019 issued in U.S. Appl. No. 15/037,468.
Office Action dated Feb. 28, 2020 issued in U.S. Appl. No. 16/372,597.
Office Action dated Jan. 20, 2015, from U.S. Appl. No. 14/026,577.
Office Action dated Jun. 20, 2014 issued in U.S. Appl. No. 13/369,558.
Office Action dated May 31, 2018 issued in U.S. Appl. No. 14/639,676.
Office Action dated Nov. 13, 2017, from U.S. Appl. No. 15/148,685.
Office Action dated Oct. 3, 2018 issued in U.S. Appl. No. 14/436,581.
Office Action dated Oct. 8, 2020 issued in U.S. Appl. No. 16/372,597.
Office Action from related U.S. Appl. No. 12/254,643, dated Aug. 6, 2010.
Office Action from related U.S. Appl. No. 11/625,099, dated Nov. 1, 2010.
Office Action from related U.S. Appl. No. 12/568,069, dated Dec. 21, 2012.
Office Action from related U.S. Appl. No. 12/568,069, dated Mar. 29, 2012.
Office Action from related U.S. Appl. No. 12/739,589, dated Jul. 19, 2012.
Office Action from related U.S. Appl. No. 13/125,522, dated Jul. 17, 2014.
Office Action from related U.S. Appl. No. 13/125,522, dated Jan. 22, 2013.
Office Action from related U.S. Appl. No. 13/143,832, dated Apr. 18, 2014.
Office Action from related U.S. Appl. No. 13/450,793, dated Aug. 1, 2014.
Office Action from related U.S. Appl. No. 13/450,793, dated Mar. 24, 2014.
Office Action from related U.S. Appl. No. 13/450,793, dated Jun. 5, 2013.
Office Action from related U.S. Appl. No. 13/574,994, dated Mar. 17, 2014.
Office Action from related U.S. Appl. No. 13/637,897, dated Aug. 1, 2014.
Office Action from related U.S. Appl. No. 14/164,117, dated Dec. 11, 2015.
Ogunlade, et al., "In vivo three-dimensional photoacoustic imaging of the renal vasculature in preclinical rodent models," Am. J. Physiol.-Ren. Physiol., vol. 314, No. 6, (2018) pp. F1145-F1153.
Oraevsky et al., "Laser Optoacoustic Tomography of Layered Tissues: Signal Processing" Proceedings of SPIE, 2979: 59-70 (1997).
Oraevsky et al.,, "Laser opto-acoustic imaging of the breast: Detection of cancer angiogenesis" Proceedings of SPIE, 3597: 352-363 (1999).
Oraevsky et al., "Optoacoustic Tomography," Biomedical Photonics Handbook, 2003, chapter 34: pp. 931-964, CRC Press LLC, USA.
Oraevsky et al., "Ultimate Sensitivity of Time-Resolved Opto-Acoustic Detection," Biomedical Optoacoustics, 2000, pp. 228-239, vol. 3916, SPIE, USA.

Parseval equality, Encyclopedia of Mathematics, retrieved on Oct. 3, 2024, 4 pages, Retrieved from Internet: URL: http://encyclopediaofmath.org/index.php?title=Parseval_equality&oldid=54876.
Partial European Search Report issued for European Application No. 17159220.7, dated Aug. 23, 2017 (9 pages).
Patel, et al., "Pulsed optoacoustic spectroscopy of condensed matter," Rev. Mod. Phys., vol. 53 (1981) pp. 517-550.
Paxton, et al., "Catalytic nanomotors: Autonomous movement of striped nanorods," J. Am. Chem. Soc. 126, 13424-13431 (2004).
Petrila, T., et al., "Basics of Fluid Mechanics and Introduction to Computational Fluid Dynamics," Springer Science & Business Media, 2004, vol. 3, pp. 1-512.
Petrov, et al., "Optoacoustic, Noninvasive, Real-Time, Continuous Monitoring of Cerebral Blood Oxygenation: An In Vivo Study in Sheep" Anesthesiology, vol. 102, No. 1, Jan. 2005, pp. 69-75.
Potter, et al., "Capillary diameter and geometry in cardiac and skeletal muscle studied by means of corrosion casts" Microvascular Research, 25(1): 68-84 (1983).
Pramanik, M., "Improving tangential resolution with a modified delayand-sum reconstruction algorithm in photoacoustic and thermoacoustic tomography," Josa A, vol. 31, No. 3, (2014) pp. 621-627.
Prati, et al., "New advances in the application of FTIR microscopy and spectroscopy for the characterization of artistic materials," Accounts of Chemical Research, vol. 43, (2010) pp. 792-801.
Prevedel, et al., "Simultaneous whole-animal 3D imaging of neuronal activity using light-field microscopy," Nat. Methods 11, 727-730 (Jul. 2014).
Quickenden, et al., "The ultraviolet absorption spectrum of liquid water," J Chem. Phys. 72, 4416-4428 (1980).
Qureshi, M., et al., "Quantitative Blood Flow Estimation in Vivo by Optical Speckle Image Velocimetry," 2021, Optica, vol. 8, p. 1326-1326.
R. A. Kruger, et al., "Dedicated 3D photoacoustic breast imaging," Med. Phys., vol. 40, No. 11, 2013, pp. 113301-1-113301-8.
Rajan, V., et al., "Review of Methodological Developments in Laser Doppler Flowmetry," Lasers in Medical Science, 2008, vol. 24(2), pp. 269-283.
Razansky, et al., "Multispectral opto-acoustic tomography of deep-seated fluorescent proteins in vivo," Nature Photonics 3, (2009) pp. 412-417.
Robert et al., "Fabrication of Focused Poly (Vinylidene Fluoride-Trifluoroethylene) P(VDF-TrFE) Copolymer 40-50 MHz Ultrasound Transducers on Curved Surfaces," Journal of Applied Physics, vol. 96, No. 1. Jul. 1, 2004, pp. 252-256.
Rockley, M.G., "Fourier-transformed infrared photoacoustic spectroscopy of polystyrene film," Chem. Phys. Lett. 68, 455-456 (1979).
Rosenblum, et al., "Progress and challenges towards targeted delivery of cancer therapeutics" Nat. Commun. 9, (2018) 1410, pp. 1-12.
Saager et al., "Direct characterization and removal of interfering absorption trends in two-layer turbid media" J. Opt. Soc. Am. A, vol. 22, No. 9, Sep. 2005, pp. 1874-1882.
Sakadzic, et al., "Correlation transfer and diffusion of ultrasound-modulated multiply scattered light," Physical Review Letters 96(16) 163902-(1-4) (Apr. 28, 2006).
Sanchez, et al., "Chemically powered micro- and nanomotors," Angew. Chem. Int. Ed. 54, (2015) pp. 1414-1444.
Savateeva, et al., "Noninvasive detection and staging or oral cancer in vivo with confocal opto-acoustic tomography" Biomedical Optoacoustics, vol. 3916, International Society for Optics and Photonics 2000, pp. 55-66.
Schambach, et al., "Application of micro-CT in small animal imaging" Methods, vol. 50, No. 1, Jan. 2010, pp. 2-13.
Schmidt, et al., "A 32-Channel Time Resolved Instrument for Medical Optical Tomography" Review of Scientific Instruments, vol. 71, No. 1, Jan. 2000, pp. 256-265.
Schoeder, et al., "Optoacoustic image reconstruction: the full inverse problem with variable bases," Proc. R. Soc. A, vol. 474, No. 2219, (2018) pp. 1-20.

(56)         References Cited

OTHER PUBLICATIONS

Scholte, et al., "On spatial sampling and aliasing in acoustic imaging" 12th Intern. congress on sound and vibration, Lisbon, Portugal (2005) pp. 1-8.

Schroeter, et al., "Spontaneous slow hemodynamic oscillations are impaired in cerebral microangiopathy," Journal of Cerebral Blood Flow & Metabolism (2005) 25, pp. 1675-1684.

Servant, et al., "Controlled In Vivo Swimming of a Swarm of Bacteria-Like Microrobotic Flagella" Advanced Materials 27, (2015) pp. 2981-2988.

Sethuraman et al., "Development of a combined intravascular ultrasound and photoacoustic imaging system" Proceedings of SPIE, 6086: 60860F.1-60860F.10 (2006).

Sethuraman et al., "Intravascular photoacoustic imaging of atherosclerotic plaques: Ex vivo study using a rabbit model of atherosclerosis" Proceedings of SPIE, 6437: 643729.1-643729.9 (2007).

Sezer, et al., "Review of magnesium-based biomaterials and their applications," J. Magnesium Alloys 6, (2018) pp. 23-43.

Shah, J. et al, "Photoacoustic imaging and temperature measurement for photothermal cancer therapy," Journal of Biomedical Optics, vol. 13, No. 3, (May/Jun. 2008) pp. 034024-1-034024-9.

Shannon, "Communication in the Presence of Noise," in Proceedings of the IRE, vol. 37, No. 1, pp. 10-21, Jan. 1949.

Sheth, et al., "Columnar Specificity of Microvascular Oxygenation and Volume Responses: Implications for Functional Brain Mapping," The Journal of Neuroscience, vol. 24, No. 3, Jan. 21, 2004, pp. 634-641.

Shi, J. et al., "High-resolution, high-contrast mid-infrared imaging of fresh biological samples with ultraviolet-localized photoacoustic microscopy," Nature Photonics, May 13, 2019, vol. 13, No. 9, pp. 609-615.

Shmueli, et al., "Low Frequency Fluctuations in the Cardiac Rate as a Source of Variance in the Resting-State fMRI BOLD Signal," Neuroimage, vol. 38, No. 2, Nov. 1, 2007, pp. 306-320.

Silva, et al., "Toward Label-Free Super-Resolution Microscopy," ACS Photon. 3, 79-86 (2016).

Sim, et al., "In vivo Microscopic Photoacoustic Spectroscopy for Non-Invasive Glucose Monitoring Invulnerable to Skin Secretion Products," Sci. Rep. 8, 1059 (2018).

Siphanto et al., "Imaging of Small Vessels Using Photoacoustics: an in Vivo Study," Lasers in Surgery and Medicince, vol. 35, Wiley-Liss, Inc., Netherlands, Dec. 20, 2004, pp. 354-362.

Sitti, M., "Miniature soft robots-road to the clinic," Nat. Rev. Mater, 3, (2018) pp. 74-75.

Smith, et al., "Beyond C, H, O, and Ni analysis of the elemental composition of U.S. FDA approved drug architectures," J. Med. Chem. 57, pp. 9764-9773 (2014).

Sommer, A. J., et al., "Attenuated total internal reflection infrared mapping microspectroscopy using an imaging microscope," Appl. Spectrosc. 55, 252-256 (2001).

Song, et al., "Section-illumination photoacoustic microscopy for dynamic 3D imaging of microcirculation in vivo" Optics Letters, 35(9): 1482-1484 (2010).

Song, et al., "Fast 3-D dark-field reflection-mode photoacoustic microscopy in vivo with a 30-MHz ultrasound linear array" Journal of Biomedical Optics, 13(5): 054028.1-054028.5 (2008).

Song, et al., "Multi-focal optical-resolution photoacoustic microscopy in vivo." NIH Public Access Author Manuscript, May 13, 2011. pp. 1-7.

Soppimath, et al., "Microspheres as floating drug-delivery systems to increase gastric retention of drugs" Drug Metab. Rev. 33, (2001) pp. 149-160.

Steinbrink, et al., "Illuminating the BOLD signal: combined fMRI-fNIRS studies" Magnetic Resonance Imaging, vol. 24, No. 4, May 2006, pp. 495-505.

Stern, MD., "In vivo evaluation of microcirculation by coherent light scattering," Nature, 254(5495): 56-58 (1975).

Szabo, T., et al., "Diagnostic Ultrasound Imaging: Inside Out (Biomedical Engineering)" Research Gate, 2014, pp. 1-5.

Tam, A. C., "Applications of photoacoustic sensing techniques," Reviews of Modern Physics, vol. 58, No. 2, Apr. 1986, pp. 381-431.

Tanter, M., et al., "Ultrafast Imaging in Biomedical Ultrasound," IEEE, 2014, vol. 61 (1), pp. 102-119.

Tay, et al., "Magnetic Particle Imaging Guided Heating In Vivo using Gradient Fields for Arbitrary Localization of Magnetic Hyperthermia Therapy" ACS Nano. 12(4), Apr. 24, 2018, pp. 3699-3713. doi:10.1021/acsnano.8b00893.

Tearney, et al., "Scanning single-mode fiber optic catheter-endos cope for optical coherence tomography" Optics Letters, 21(7): 543-545 (1996).

The International Search Report and the Written Opinion of the International Searching Authority, Sep. 22, 2011 , from related application No. PCT/US2011/022253, 6 pgs.

The International Search Report and the Written Opinion of the International Searching Authority, or the Declaration, for PCT/US2009/061435, dated Mar. 29, 2010, 6 pages.

The International Search Report and Written Opinion dated Mar. 27, 2014 issued in Application No. PCT/US2013/065594.

Townsend, D., et al., "PET/CT today and tomorrow," Journal of nuclear medicine, 2004, vol. 45, pp. 4S-14S.

Tran, et al., "In vivo endoscopic optical coherence tomography by use of a rotational microelectromechanical system probe" Optics Letters, 29(11): 1236-1238 (2004).

Treeby B. E., et al., "Photoacoustic Tomography in Absorbing Acoustic Media Using Time Reversal," Inverse Problems, Sep. 24, 2010, vol. 26(11), 2010.

Treeby, et al., "Advanced photoacoustic image reconstruction using the k-Wave toolbox," in Photons Plus Ultrasound: Imaging and Sensing 2016, 2016, vol. 9708, p. 97082P.

Treeby, et al., "k-Wave: MATLAB toolbox for the simulation and reconstruction of photoacoustic wave fields," J. Biomed. Opt., vol. 15, No. 2, Mar./Apr. 2010, pp. 021314.

Tu, et al., "Self-propelled supramolecular nanomotors with temperature-responsive speed regulation," Nat. Chem. 9, 480 (2016).

Tzoumas, et al., "Eigenspectra optoacoustic tomography achieves quantitative blood oxygenation imaging deep in tissues," Nat. Commun., vol. 7, 2016, pp. 1-10.

U.S. Advisory Action dated Dec. 8, 2023 in U.S. Appl. No. 17/302,041.

U.S Corrected Notice of Allowance dated Apr. 27, 2022 in U.S. Appl. No. 16/540,936.

U.S. Corrected Notice of Allowance dated Jun. 2, 2022 in U.S. Appl. No. 16/806,796.

U.S. Corrected Notice of Allowance dated Nov. 14, 2022 in U.S. Appl. No. 16/540,936.

U.S. Corrected Notice of Allowance dated Sep. 19, 2023, in U.S. Appl. No. 17/090,752.

U.S. Ex Parte Quayle Action dated Dec. 13, 2021 in U.S. Appl. No. 16/611,939.

U.S. Final office Action dated Jan. 27, 2023 in U.S. Appl. No. 16/798,204.

U.S. Final office Action dated Jun. 20, 2023 in U.S. Appl. No. 17/302,313.

U.S. Final office Action dated Jun. 26, 2023 in U.S. Appl. No. 17/090,752.

U.S. Final Office Action dated May 24, 2024 in U.S. Appl. No. 16/946,496.

U.S. Final Office Action dated Sep. 25, 2023, in U.S. Appl. No. 17/302,041.

U.S. Non Final Office Action dated Aug. 26, 2022 in U.S. Appl. No. 17/302,313.

U.S. Non-Final Office Action dated Aug. 14, 2023, in U.S. Appl. No. 16/798,204.

U.S. Non-Final office Action dated Dec. 21, 2022 in U.S. Appl. No. 17/090,752.

U.S. Non-Final office Action dated Jan. 23, 2023 in U.S. Appl. No. 17/302,313.

U.S. Non-Final Office Action dated Jul. 26, 2024 in U.S. Appl. No. 16/798,204.

U.S. Non-Final Office Action dated Mar. 20, 2023 in U.S. Appl. No. 17/302,041.

(56)          References Cited

OTHER PUBLICATIONS

U.S. Non-Final Office Action dated Mar. 27, 2024 in U.S. Appl. No. 17/302,041.
U.S. Non-Final Office Action dated May 2, 2022 in U.S. Appl. No. 16/798,204.
U.S. Non-Final Office Action dated Oct. 20, 2023, in U.S. Appl. No. 16/946,496.
U.S. Non-Final Office Action dated Sep. 25, 2024 in U.S. Appl. No. 18/336,834.
U.S. Notice of Allowance dated Apr. 18, 2024 in U.S. Appl. No. 17/090,752.
U.S Notice of Allowance dated Apr. 19, 2022 in U.S. Appl. No. 16/540,936.
U.S. Notice of Allowance dated Apr. 25, 2024 in U.S. Appl. No. 17/090,752.
U.S. Notice of Allowance dated Aug. 5, 2022 in U.S. Appl. No. 16/540,936.
U.S. Notice of Allowance dated Dec. 22, 2022 in U.S. Appl. No. 16/611,939.
U.S. Notice of Allowance dated Feb. 23, 2022 in U.S. Appl. No. 16/806,796.
U.S. Notice of Allowance dated Jan. 10, 2024 in U.S. Appl. No. 17/090,752.
U.S. Notice of Allowance dated Jan. 26, 2023 in U.S. Appl. No. 16/560,680.
U.S. Notice of Allowance dated Mar. 13, 2024 in U.S. Appl. No. 17/302,313.
U.S. Notice of Allowance dated Nov. 29, 2023 in U.S. Appl. No. 17/302,313.
U.S. Notice of Allowance dated Oct. 19, 2022 in U.S. Appl. No. 16/560,680.
U.S. Notice of Allowance dated Sep. 7, 2022 in U.S. Appl. No. 16/611,939.
U.S. Notice of Allowance dated Sep. 7, 2023, in U.S. Appl. No. 17/090,752.
U.S. Notice of Allowance dated Sep. 13, 2023 in U.S. Appl. No. 17/302,313.
U.S. Office Action dated Apr. 7, 2022, in U.S. Appl. No. 16/560,680.
U.S. Appl. No. 18/658,435, inventors Hu P, et al., filed May 8, 2024.
U.S. Appl. No. 18/658,823, inventors Hu P, et al., filed May 8, 2024.
U.S. Requirement for Restriction dated Oct. 29, 2021 in U.S. Appl. No. 16/560,680.
U.S Restriction requirement dated Aug. 9, 2023 in U.S. Appl. No. 16/946,496.
U.S. Restriction Requirement dated Dec. 15, 2022 in U.S. Appl. No. 17/302,041.
U.S. Restriction Requirement dated Sep. 16, 2024 in U.S. Appl. No. 17/820,496.
Van Essen, et al., "An Integrated Software Suite for Surface-based Analyses of Cerebral Cortex" Journal of the American Medical Informatics Association, vol. 8, No. 5, Sep./Oct. 2001, pp. 443-459.
Velasco, E., "Ultrafast Camera Takes 1 Trillion Frames Per Second of Transparent Objects and Phenomena" [Webpage] Caltech, California Institute of Technology, Jan. 17, 2020, pp. 1-2. URL:https://www.eurekalert.org/pub_releases/2020-01/ciot-uct012120.php.
Viator et al., "Design testing of an endoscopic photoacoustic probe for determination of treatment depth after photodynamic therapy" Proceedings of SPIE in Biomedical Optoacoustics II, 4256: 16-27 (2001).
Vilela, et al., "Medical imaging for the tracking of micromotors," ACS Nano 12, (2018) pp. 1220-1227.
Wang, B. et al., "Recent progress on micro- and nano-robots: towards in vivo tracking and localization" Quantitative Imaging in Medicine and Surgery, 2018, vol. 8, No. 5, pp. 461-479. DOI: 10.21037/qims.2018.06.07.
Wang, et al., "Ballistic 2-D Imaging Through Scattering Walls Using an Ultrafast Optical Kerr Gale," Science, vol. 253, Aug. 16, 1991, pp. 769-771.

Wang et al., "Biomedical optics: principles and imaging," Section 12.5; Photoacoustic Tomography, John Wiley & Sons (2012) pp. 288-290.
Wang, et al., "Biomedical Optics, Principles and Imaging," Wiley-Interscience, A John Wiley & Sons, Inc., (2007) p. 7.
Wang, et al., "Fabrication of micro/nanoscale motors" Chem. Rev. 115, (2015) pp. 8704-8735.
Wang, et al., "Intravascular Photoacoustic Imaging" IEEE J Quantum Electronics, 16(3): 588-599 (2010).
Wang, et al., "MCML—Monte Carlo modeling of light transport in multi-layered tissues" Computer Methods and Programs in Biomedicine, vol. 47, No. 2, Jul. 1995, pp. 131-146.
Wang, et al., "Nano/microscale motors: biomedical opportunities and challenges," ACS Nano 6, (2012) pp. 5745-5751.
Wang et al., "Noninvasive photoacoustic angiography of animal brains in vivo with near-infrared light and an optical contrast agent" Optics Letters, 29(7): 730-732 (2004).
Wang et al., "Three-dimensional laser-induced photoacoustic tomography of mouse brain with the skin and skull intact," Optics Letters, 28(19): 1739-1741 (2003).
Wang, K. et al., "Investigation of iterative image reconstruction in three-dimensional optoacoustic tomography," Phys. Med. Biol., vol. 57, No. 17, 2012, p. 5399-5423.
Wang, L., et al., "Biomedical optics: principles and imaging," 2012, 368 pages.
Wang, L. et al., "Grueneisen relaxation photoacoustic microscopy," Physical Review Letters 113 174301 (Oct. 24, 2014).
Wang, L., et al., "Single-cell label-free photoacoustic flowoxigraphy in vivo," Proceedings of the National Academy of Sciences 110(15) 5759-5764 (Apr. 9, 2013).
Wang, L., et al., "Photoacoustic Tomography: in Vivo Imaging From Organelles to Organs," Science, 2012, vol. 335(6075), pp. 1458-1462.
Wang, L., et al., "Photoacoustic Tomography: Ultrasonically Breaking Through the Optical Diffusion Limit," Optics in the Life Sciences, 2011.
Wang, L., et al., "Tutorial on Photoacoustic Microscopy and Computed Tomography," IEEE Journal of Selected Topics in Quantum Electronics, 2008, vol. 14(1), pp. 171-179.
Wang, L., et al., "Ultrasonically encoded photoacoustic flowgraphy in biological tissue," Physical Review Letters 111(20), 204301 (Nov. 15, 2013).
Wang, L. V & Yao, J., "A practical guide to photoacoustic tomography in the life sciences," Nat. Methods 13, 627-638 (Jul. 28, 2016).
Wang, L. V.; "Mechanisms of ultrasonic modulation of multiply scattered coherent light: an analytic model," Physical Review Letters 87(4) 043903-(1-4) (Jul. 23, 2001).
Wang, L. V., "Multiscale photoacoustic microscopy and computed tomography," Nat. Photon. 3, 503-509 (Aug. 29, 2009).
Wang, L. V.; "Prospects of photoacoustic tomography," Medical Physics 35(12), Nov. 19, 2008, pp. 5758-5767.
Wang, X. D., et al., "Noninvasive laser-induced photoacoustic tomography for structural and functional in vivo imaging of the brain," Nature Biotechnology 21(7) 803-806 (Jul. 2003).
Wetzel, et al., "Imaging molecular chemistry with infrared microscopy," Science, New Series, vol. 285, No. 5431, Aug. 20, 1999, pp. 1224-1225.
White D.N., et al., "Effect of Skull in Degrading the Display of Echoencephalographic Band C Scans," The Journal of the Acoustical Society of America, Nov. 1968, vol. 44(5), pp. 1339-1345.
Wiedeman, M., et al., "Dimensions of Blood Vessels From Distributing Artery to Collecting Vein," Circulation research, 1963, vol. 12(4), pp. 375-378.
Won, R., et al., "Mapping Blood Flow," Nature Photonics, 2011, p. 393-393.
Wong, et al., "Label-free automated three-dimensional imaging of whole organs by microtomy-assisted photoacoustic microscopy," Nature Communications 8(1) 1386 (2017), pp. 1-8.
Wong, T. et al., "Fast label-free multilayered histology-like imaging of human breast cancer by photoacoustic microscopy," Sci. Adv. 3, 1602168 (May 17, 2017).

(56)        References Cited

OTHER PUBLICATIONS

Wu, D., et al., "In vivo Mapping of Macroscopic Neuronal Projections in the Mouse Hippocampus using High-resolution Diffusion MRI," Neuroimage 125, Jan. 15, 2016, pp. 84-93.

Wu, Z., et al., "A microrobotic system guided by photoacoustic computed tomography for targeted navigation in intestines in vivo," Science Robotics 4(32) eaax0613 (Jul. 24, 2019).

Xia, J., et al., "Photoacoustic tomography: principles and advances," Electromagn. Waves 147, 1 (2014; available in PMC Jan. 30, 2015).

Xia, J., et al., "Wide-field two-dimensional multifocal optical-resolution photoacoustic-computed microscopy," Opt. Lett. 38(24), Dec. 15, 2013, pp. 5236-5239.

Xu, et al., "Exact frequency-domain reconstruction for thermoacoustic tomography-II: Cylindrical geometry," IEEE Trans. Med. Imaging, vol. 21, No. 7, (2002) pp. 829-833.

Xu, et al., "Photoacoustic Imaging in Biomedicine," Review of Scientific Instruments, American Institute of Physics, vol. 77 (2006) pp. 041101 1-22.

Xu, et al., "Rhesus monkey brain imaging through intact skull with thermoacoustic tomography," IEEE Trans. Ultrason. Ferroelectr. Freq. Control, vol. 53, No. 3, Mar. 2006, pp. 542-548.

Xu, et al., "Time reversal and its application to tomography with diffracting sources," Physical Review Letters 92(3) 033902-(1-4) (Jan. 23, 2004).

Xu, et al., "Time-domain reconstruction for thermoacoustic tomography in a spherical geometry," IEEE Transactions on Medical Imaging 21(7) 814-822 (Jul. 2002).

Xu M, et al., "Universal back-projection algorithm for photoacoustic computed tomography," Physical Review E 71 (1) 016706-(1-7) (Jan. 19, 2005).

Xu, S., et al., "Thermal expansion of confined water," Langmuir 25, 5076-5083 (2009).

Xu, X. et al., "Time Reversal Ultrasound Modulated Optical Tomography Using a BSO Phase Conjugate Mirror," Society of Photo-Optical Instrumentation Engineers (SPIE) Conference (Feb. 12, 2009), 1 page.

Xu, X. et al., "Time-reversed ultrasonically encoded optical focusing into scattering media," Nature Photonics 5(3) 154-157 (Jan. 16, 2011).

Yadlowsky, et al., "Multiple scattering in optical coherence microscopy" Applied Optics, vol. 34, No. 25 (1995) pp. 5699-5707. doi.org/10.1364/AO.34.005699.

Yan, et al., "Multifunctional biohybrid magnetite microrobots for imaging-guided therapy" Yan et al., Sci. Robot. 2, eaaq1155, Nov. 22, 2017, pp. 1-14.

Yang, et al., "Novel biomedical imaging that combines intravascular ultrasound (IVUS) and optical coherence tomography (OCT)" IEEE International Ultrasonics Symposium, Beijing, China, Nov. 2-5, 2008, pp. 1769-1772.

Yang, et al., "The grand challenges of science robotics," Science Robotics 3, Jan. 31, 2018, eaar7650, pp. 1-14.

Yang, et al., "Time-reversed ultrasonically encoded optical focusing using two ultrasonic transducers for improved ultrasonic axial resolution" Journal of Biomedical Optics 18(11), 110502 (Nov. 2013) pp. 110502-1-110502-4.

Yang, J. et al. Focusing light inside live tissue using reversibly switchable bacterial phy-tochrome as a genetically encoded photochromic guide star. Science Advances 5. eprint: https : / / advances . sciencemag . org / content / 5 / 12 / eaay1211 . full . pdf. https : / /advances.sciencemag.org/content/5/12/eaay1211 (2019).

Yang, J., et al., "Motionless volumetric photoacoustic microscopy with spatially invariant resolution," Nature Communications 8(1) 780 (Oct. 3, 2017).

Yang, J. M. et al., "Simultaneous functional photoacoustic and ultrasonic endoscopy of internal organs in vivo," Nature Medicine 18(8) 1297-1303 (Aug. 2012).

Yang, "Optical coherence and Doppler tomography for monitoring tissue changes induced by laser thermal therapy—An in vivo feasibility study" Review of Scientific Instruments, vol. 74, No. 1, Jan. 2003, p. 437-440.

Yao, D. et al., "Optimal ultraviolet wavelength for in vivo photoacoustic imaging of cell nuclei," Journal of Biomedical Optics, May 4, 2012, vol. 17, No. 5, p. 056004.

Yao, et al., "Absolute photoacoustic thermometry in deep tissue," Opt. Lett. 38, 5228-5231 (2013).

Yao, et al., "In vivo label-free photoacoustic microscopy of cell nuclei by excitation of DNA and RNA," Opt. Lett. 35, 4139-4141 (2010).

Yao, et al., "Monte Carlo simulation of an optical coherence tomography signal in homogeneous turbid media" Phys. Med. Biol. 44(9), Jul. 8, 1999, pp. 2307-2320.

Yao, et al., "Photoimprint photoacoustic microscopy for three-dimensional label-free sub-diffraction imaging," Physical Review Letters 112(1) 014302 (Jan. 10, 2014).

Yao, J. et al., "Double-illumination Photoacoustic Microscopy", Optics Letters, Feb. 15, 2012, vol. 37, No. 4, pp. 659-661.

Yao, J., et al., "In vivo Photoacoustic Tomography of Total Blood Flow and Potential Imaging of Cancer Angiogenesis and Hypermetabolism," Technology in Cancer Research and Treatment, 2012, vol. 11(4), pp. 301-307.

Yao, J., et al., "Photoacoustic brain imaging: from microscopic to macroscopic scales," Neurophotonics, 2014, vol. 1(1), 13 Pages.

Yao, J., et al., "Transverse Flow Imaging Based on Photoacoustic Doppler Bandwidth Broadening," Journal of Biomedical Optics, 2010, vol. 15(2), 5 Pages.

Yao, J., "Label-free Oxygen-metabolic Photoacoustic Microscopy in Vivo," Journal of biomedical optics, 2011, vol. 16(7).

Yao, L. et al., "High-speed label-free functional photoacoustic microscopy of mouse brain in action," Nat. Methods 12(5), 407-410 (May 12, 2015).

Yao, L. et al., "Multiscale photoacoustic tomography using reversibly switchable bacterial phytochrome as near-infrared photochromic probe," Nature Methods 13(1) 67-73 (Jan. 2016).

Yao, L. et al., "Photoacoustic microscopy: superdepth, superresolution, and superb contrast", IEEE Pulse 6, 34-7 (May 13, 2015).

Yaqoob, et al., "Methods and application areas of endoscopic optical coherence tomography" Journal of Biomedical Optics, 11(6): 063001. 1-063001.19 (2006).

Yavuz, M. S., et al., "Gold nanocages covered by smart polymers for controlled release with near-infrared light," Nature Materials 8(12) 935-939 (Nov. 1, 2009).

Yin, et al., "Agarose particle-templated porous bacterial cellulose and its application in cartilage growth in vitro" Acta Biomater. Jan. 12, 2015, pp. 129-138. doi:10.1016/j.actbio.2014.10.019.

Yodh et al., "Functional Imaging with Diffusing Light" Biomedical Photonics Handbook, 2003, Ch. 21 , pp. 45, CRC Press, Boca Raton.

Yodh, et al. "Spectroscopy and Imaging with Diffusing Light" Physics Today 48(3), Mar. 1995, pp. 34-40.

Zangabad, R., et al., "Photoacoustic Flow Velocity Imaging Based on Complex Field Decorrelation," Photoacoustic, 2021,8 pages.

Zeff, et al., "Retinotopic mapping of adult human visual cortex with high-density diffuse optical tomography" PNAS, vol. 104, No. 29, Jul. 17, 2007, pp. 12169-12174.

Zemp, et al., "Realtime photoacoustic microscopy in vivo with a 30MHZ ultrasonic array transducer" Optics Express, 16(11): 7915-7928 (2008).

Zeniieh, D., et al., Parylene-C as High Performance Encapsulation Material for Implantable Sensors, Procedia Engineering, 2014, vol. 87, pp. 1398-1401. https://doi.org/10.1016/j.proeng.2014.11.704.

Zhang, C., et al., "Coherent Raman scattering microscopy in biology and medicine," Annu. Rev. Biomed. Eng. 17, 415-445 (2015).

Zhang, D. et al., "Depth-resolved mid-infrared photothermal imaging of living cells and organisms with submicrometer spatial resolution," Sci. Adv. 2, el600521 (2016).

Zhang, et al., "Intrinsic Functional Relations Between Human Cerebral Cortex and Thalamus" Journal of Neurophysiology, vol. 100, No. 4, Oct. 2008, pp. 1740-1748.

Zhang, H. F. et al., "Functional photoacoustic microscopy for high-resolution and noninvasive in vivo imaging," Nature Biotechnology 24(7) 848-851 (Jul. 2006).

(56) References Cited

OTHER PUBLICATIONS

Zhang, H. F. et al., "In vivo imaging of subcutaneous structures using functional photoacoustic microscopy," Nature Protocols 2(4) 797-804 (Apr. 5, 2007).

Zhang, Y., et al., "Photoacoustic Vector Tomography for Deep Haemodynamic Imaging," Nature biomedical engineering, 2023, pp. 1-29.

Zhang, Y., et al., "Transcranial Photoacoustic Computed Tomography of Human Brain Function," Arxiv, 2022, pp. 1-12.

Zhang, Y., et al., Ultrafast Ultrasound Imaging With Cascaded Dual-polarity Waves, IEEE, 2018, vol. 37(4), pp. 906-917.

Zharov, et al., "In vivo photoacoustic flow cytometry for monitor of circulating single cancer cells and contrast agents," Optics Letters, 31(24): 3623-3625 (2006).

Zhou, et al., "Tutorial on photoacoustic tomography," J. Biomed. Opt., vol. 21, No. 6, Jun. 2016, pp. 061007-1-061007-14.

Zhu et al., "Light Emitting Diodes based Photoacoustic Imaging and Potential Clinical Applications", Scientific Reports, 2018, vol. 8(1):9885, pp. 1-12.

Zou, et al., "BOLD responses to visual stimulation in survivors of childhood cancer" NeuroImage, vol. 24, No. 1, Jan. 1, 2005, pp. 61-69.

English Machine Translation of JP 2010-40161 A. (Year: 2019).

EP Office Action dated May 26, 2025, in Application No. EP19857631. 6.

Office Action (Non-Final Rejection) dated Apr. 24, 2025 for U.S. Appl. No. 17/820,496 (pp. 1-9).

Office Action (Non-Final Rejection) dated May 5, 2025 for U.S. Appl. No. 18/336,834 (pp. 1-34).

Office Action (Notice of Allowance and Fees Due (PTOL-85)) dated May 20, 2025 for U.S. Appl. No. 17/302,041 (pp. 1-5).

Rosenthal A., et al., "Acoustic Inversion in Optoacoustic Tomography: A Review," Current Medical Imaging Reviews, 2013, vol. 9 (4), pp. 318-336.

U.S. Appl. No. 18/450,597, inventors Hu P, et al., filed Aug. 16, 2023.

U.S. Appl. No. 16/540,936, inventors Wang et al., filed Aug. 14, 2019.

U.S. Appl. No. 16/560,680, inventors Wang et al., filed Sep. 4, 2019.

U.S. Appl. No. 16/611,939, inventors Wang et al., filed Nov. 8, 2019.

U.S. Appl. No. 16/798,204, inventors Wang et al., filed Feb. 21, 2020.

U.S. Appl. No. 16/806,796, inventors Wang et al., filed Mar. 2, 2020.

U.S. Appl. No. 16/946,496, inventors Gao et al., filed Jun. 24, 2020.

U.S. Appl. No. 17/090,752, inventors Wang et al., filed Nov. 5, 2020.

U.S. Appl. No. 17/302,041, inventors Wang et al., filed Apr. 22, 2021.

U.S. Appl. No. 17/302,313, inventors Wang et al., filed Apr. 29, 2021.

U.S. Appl. No. 62/718,777, inventors Wang et al., filed Aug. 14, 2018.

U.S. Corrected Notice of Allowance dated Oct. 26, 2022 in U.S. Appl. No. 16/560,680.

U.S. Final Office Action dated Feb. 20, 2025 in U.S. Appl. No. 18/336,834.

U.S. Final Office Action dated Mar. 28, 2025 in U.S. Appl. No. 16/798,204.

U.S. Non-Final Office Action dated Dec. 17, 2024 in U.S. Appl. No. 16/946,496.

U.S. Non-Final Office Action dated Mar. 14, 2025 in U.S. Appl. No. 18/450,597.

U.S. Notice of Allowance dated Feb. 14, 2025 in U.S. Appl. No. 17/302,041.

U.S. Appl. No. 18/336,834, inventors Zhang et al., filed Jun. 16, 2023.

U.S. Appl. No. 18/336,863, inventors Garrett D C, et al., filed Jun. 16, 2023.

U.S. Appl. No. 18/410,842, inventor Wang L, et al., filed Jan. 11, 2024.

Office action dated Jul. 10, 2025 for U.S. Appl. No. 16/946,496 (pp. 1-22).

Office Action (Final Rejection) dated Jul. 10, 2025 for U.S. Appl. No. 16/946,496 (pp. 1-21).

J. Arrowood et al, "Gibbs Phenomenon Suppression Using Fir Time-Varying Filter Banks", The Digital Signal Processing workshop, pp. 2.1.1-2.1.2, Sep. 1992 (Year: 1992).

M. Jaeger et al, "Fourier reconstruction in optoacoustic imaging using truncated regularized inverse k-space interpolation", Inverse Problems, vol. 23, pp. S51-S63, Mar. 2007 (Year: 2007).

M. Roumeliotis et al, "Analysis of a photoacoustic imaging system by the crosstalk matrix and singular value decomposition", Optics Express, vol. 18, No. 11, pp. 11406-11417, May 2010 (Year: 2010).

M. Roumeliotis et al, "Singular value decomposition analysis of a photoacoustic imaging system and 3D imaging at 0.7 FPS", Optics Express, vol. 19, No. 14, pp. 13405-13417, Apr. 2011 (Year: 2011).

B. Treeby, "Acoustic attenuation compensation in photoacoustic tomography using time-variant filtering", Journal of Biomedical Optics, vol. 18, No. 3, pp. 1-11, Mar. 2013 (Year: 2013).

K. Wang et al, "Fast spatiotemporal image reconstruction based on low-rank matrix estimation for dynamic photoacoustic computed tomography", Journal of Biomedical Optics, vol. 19, No. 5, pp. 1-11, May 2014 (Year: 2014).

H. Huang et al, "An adaptive filtered back-projection for photoacoustic image reconstruction", Medical Physics, vol. 42, No. 5, pp. 2169-2178, May 2015 (Year: 2015).

E. Hill et al, "Identification and removal of laser-induced noise in photoacoustic imaging using singular value decomposition", Biomedical Optics Express, vol. 8, No. 1, pp. 68-77, Jan. 2017 (Year: 2017).

G. Zhang et al, "High Signal-to-Noise Ratio Contrast-Enhanced Photoacoustic Imaging using Acoustic Sub-Aperture Processing and Spatiotemporal Filtering", 2019 IEEE International Ultrasonics Symposium (IUS), pp. 494-497, Oct. 2019 (Year: 2019).

Office Action (Final Rejection) dated Aug. 27, 2025 for U.S. Appl. No. 18/450,597 (pp. 1-17).

* cited by examiner

1028

652

654

TRANSMISSION MODE-PHOTOACOUSTIC TOMOGRAPHY OF THE HUMAN BRAIN THROUGH AN ACOUSTIC WINDOW

CROSS-REFERENCES TO RELATED APPLICATIONS

This application claims benefit of and priority to U.S. Provisional Patent Application No. 63/458,853, titled "Transmission Mode-Photoacoustic Tomography of the Human Brain Through an Acoustic Window," and filed on Apr. 12, 2023, which is incorporated by reference herein in its entirety and for all purposes.

FEDERALLY SPONSORED RESEARCH OR DEVELOPMENT

This invention was made with government support under Grant No(s). EB029823 & CA220436 & NS102213 awarded by the National Institutes of Health. The government has certain rights in the invention."

FIELD

Certain aspects generally pertain to photoacoustic imaging and, more specifically, to transmission-mode photoacoustic tomography imaging of the brain.

BACKGROUND

Several imaging modalities that have been proposed for brain imaging have significant limitations. For example, magnetic resonance imaging (MRI) machines are expensive, bulky, closed, loud, and slow. Further, MRI is contraindicated in claustrophobic individuals and individuals with ferromagnetic implants. As another example, positron emission tomography (PET) may be used to image neuro-metabolism in the human brain, however, it suffers from poor spatial resolution and uses harmful radioactive tracers. In yet another example, electroencephalography (EEG) can measure the electrical activity in the brain at a high temporal resolution but lacks spatial resolution. Similarly, function near-infrared spectroscopy (fNIRS) can image brain function with high temporal resolutions but suffers from poor spatial resolution. Functional ultrasound (fUS) has been used for imaging by delivering acoustic waves into the neonatal brain through the fontanelles, however, imaging cerebral vasculature in the skull of an adult human requires the use of contrast agents.

Background and contextual descriptions contained herein are provided solely for the purpose of generally presenting the context of the disclosure. Much of this disclosure presents work of the inventors, and simply because such work is described in the background section or presented as context elsewhere herein does not mean that such work is admitted prior art.

SUMMARY

Certain embodiments pertain to photoacoustic imaging methods. In some embodiments, a photoacoustic imaging method includes delivering diffuse light in transmission mode through a skull to a region being imaged in a brain and using an ultrasonic transducer device to detect acoustic waves transmitted from the region through an acoustic window in the skull. The acoustic waves are generated by the photoacoustic effect from the diffuse light delivered to the region. The photoacoustic imaging method also includes reconstructing a plurality of photoacoustic images of the region based on the acoustic waves detected.

In some embodiments, a photoacoustic imaging method includes obtaining photoacoustic data recorded by one or more data acquisition devices. The photoacoustic data is from acoustic signals of acoustic waves received through an acoustic window in a skull and detected by an ultrasonic transducer device. The acoustic waves are generated via the photoacoustic effect from light delivered to a region being imaged in a brain. The light is delivered to the brain in transmission mode through the skull to the brain. The photoacoustic imaging methods also includes reconstructing a plurality of photoacoustic images of the region based on the acoustic waves detected.

Certain embodiments pertain to photoacoustic imaging systems. In some embodiments, a photoacoustic imaging system includes a light delivery module configured to deliver diffuse light in transmission mode through a skull to a region being imaged in a brain. The photoacoustic imaging system also includes an acoustic detection module configured to detect acoustic waves through an acoustic window in the skull. The acoustic waves are generated by a photoacoustic effect from the diffuse light delivered to the region being imaged. The photoacoustic imaging system also includes a data acquisition module configured to receive acoustic signals from the acoustic detection system.

These and other features and embodiments will be described in more detail with reference to the drawings.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Figure 1:
FIG. 1 depicts a schematic diagram illustrating a transmission-mode photoacoustic tomography of the brain through an acoustic window (TPT) technique, according to embodiments.
Figure 1:
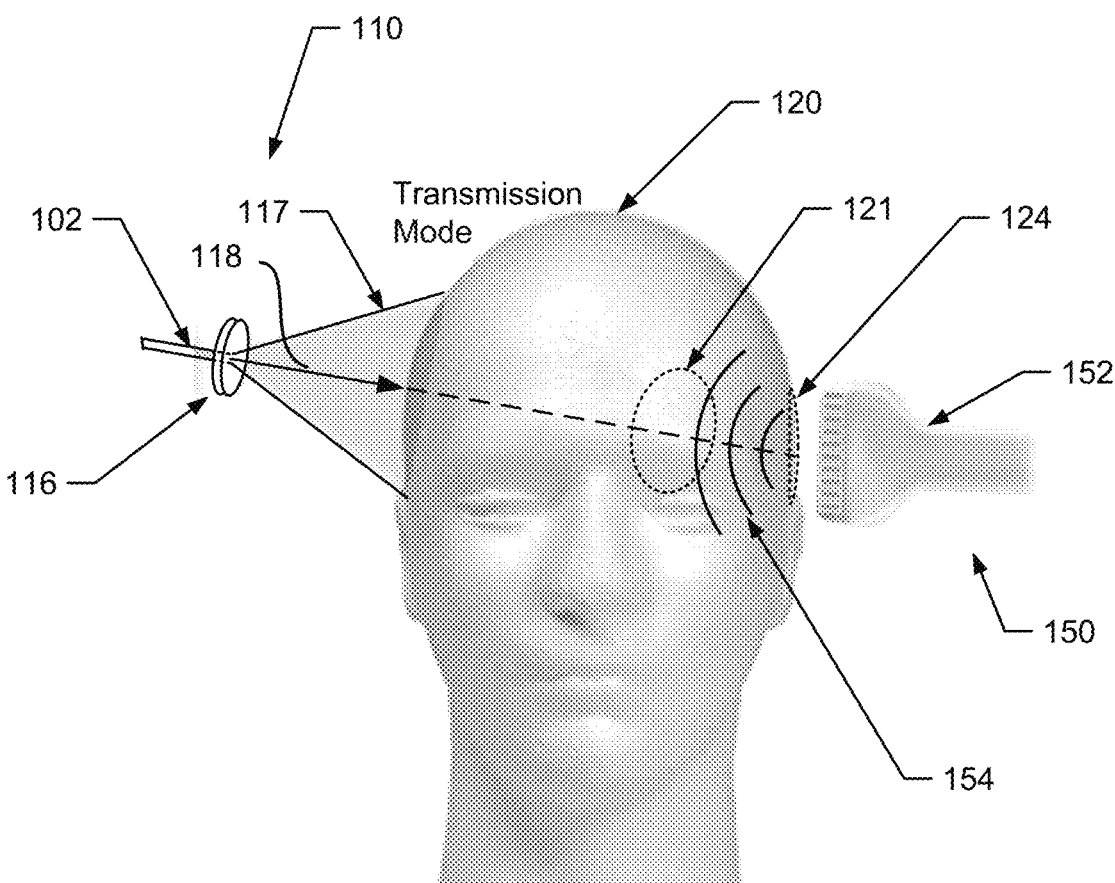

The figures and components therein may not be drawn to scale.

DETAILED DESCRIPTION

Different aspects are described below with reference to the accompanying drawings. In the following description, numerous specific details are set forth in order to provide a thorough understanding of the presented embodiments. The disclosed embodiments may be practiced without one or more of these specific details. In other instances, well-known operations have not been described in detail to avoid unnecessarily obscuring the disclosed embodiments. While the disclosed embodiments will be described in conjunction with the specific embodiments, it will be understood that it is not intended to limit the disclosed embodiments.

I. Introduction

Photoacoustic computed tomography (PACT) is a medical imaging technique that combines the rich molecular specificity of optical absorption contrast with the low tissue scattering property of ultrasound. In PACT, light from a pulsed laser is allowed to diffuse into a tissue where it gets absorbed and converted into acoustic waves via the photoacoustic effect. The acoustic waves, which experience much lower scattering than light in tissue, can be recorded and used to reconstruct high-resolution images of the tissue.

Conventional PACT techniques have been shown to be capable of imaging the human breast and human extremities. There are, however, significant obstacles that prevent conventional PACT techniques from reaching their full potential in imaging the brain. One key obstacle is the skull. The skull not only attenuates light passing through to the brain, but it also distorts and dampens the generated photoacoustic waves.

Disclosed herein are techniques for performing transmission-mode photoacoustic tomography of the brain through an acoustic window (TPT). These TPT techniques involve delivering diffuse light in transmission-mode through the skull to a region being imaged in the brain and detecting the resulting acoustic signals through an acoustic window. Receiving acoustic signals through an acoustic window serves to minimize the skull-induced attenuations and aberrations, thus allowing for reconstruction of minimally distorted images of the brain through the skull. TPT techniques deliver the diffuse light in transmission-mode (i.e., transmission of light through the skull and tissues of the brain) to the region of interest being imaged. In the context of human brain photoacoustic imaging, transmission mode has several advantages over reflection mode. For example, transmission mode is not affected by the scalp reflection which can be two orders of magnitude stronger than cortical signals. As another example, the acoustic waves generated on one side of the brain experience near-normal incidence on the other side, which results in a reduced skull aberration. As another example, the efficiency of light delivery is much higher in transmission mode since light is directly delivered to the skin without attenuation from any ultrasound coupling medium in reflection mode (e.g., water). In yet another example, transmission mode allows for imaging of a large region through a small acoustic window (e.g., temporal bone) which is not possible in reflection mode. TPT techniques have tremendous potential for becoming clinically relevant human brain imaging techniques.

TPT techniques are a useful tool for structural and functional human brain imaging that may be valuable for researchers and clinicians alike. TPT techniques involve delivering light to the imaging region of interest in the brain and detecting the resulting acoustic signals through an acoustic window. For healthy adults, the temporal region (transtemporal window) can serve as an acoustic window, while for hemicraniectomy patients, the skull-less side can be utilized. In neonates, fontanelles may serve as an acoustic window. Other potential acoustic windows include the submandibular, transorbital, suboccipital and other high acoustic transmittance regions in the head. Receiving the acoustic waves through an acoustic window minimizes the skull-induced attenuations and aberrations, thus allowing us to reconstruct minimally distorted images of the human brain through the skull.

Certain embodiments pertain to a TPT technique that can perform transcranial imaging of the human brain. The TPT technique involves light delivery to the brain through an articulated arm, an optical fiber bundle, free space, or any other mechanism. Further, it includes acoustic wave detection through an acoustic window to the brain. Some examples of acoustic windows are the skull-less side for hemicraniectomy patients, and the temporal region, the submandibular region, the transorbital region, and the suboccipital region for healthy adults.

As used herein, an "acoustic window" refers to a region of the skull where the bone is relatively thinner than in other regions of the skull or where there is an opening in the skull (e.g., gap, bone flap, fissure, etc.) that, e.g., allows for adequate transmission of acoustic waves with minimal distortion for image reconstruction. For example, an acoustic window may be a region of the skull having an average or mean thickness of bone tissue in a range of 0 mm to 4 mm. Some examples of acoustic windows include a temporal region of the skull (e.g., temporal region of an adult human), a hemicraniectomy region or other gap in the skull, a fontanelle (e.g., fontanelle of a human infant), a submandibular region, a transorbital region, a suboccipital region, and a transfrontal region, and a transoccipital region. Another example of an acoustic window is a skull-implant, in which part of the skull bone is replaced with an artificial skull with better acoustic properties. A temporal region (also referred to as a "transtemporal region" or "transtemporal window") generally refers to a region of the skull adjacent the temporal lobes. A hemicraniectomy region refers to a region of the skull removed in a hemicraniectomy operation. For example, in healthy adults, a temporal region may serve as an acoustic window, while for hemicraniectomy patients, the skull-less side may be used. As another example, in neonates, fontanelles may serve as an acoustic window. Some other examples of acoustic windows that can be used include submandibular, transorbital, suboccipital and other high acoustic transmittance regions in the head. Receiving acoustic waves through an acoustic window in the skull may serve to minimize skull-induced attenuations and aberrations, which advantageously allows for reconstruction of minimally distorted images of the brain through the skull.

An "optical window" generally refers to a region of the skull where the bone is relatively thinner than in other regions of the skull or where there is an opening in the skull. In certain implementations that involve, e.g., hemicraniectomy patients, through-fontanelle illumination in neonates, and patients during open-brain surgery, diffuse light may be delivered to the brain through an optical window such that light reaches the brain without encountering the skull bone. In these cases, the use of the optical window allows for delivery of light to the target with minimal light attenuation, thus resulting in strong photoacoustic signals.

II. Transmission-Mode Photoacoustic Tomography of the Brain Through an Acoustic Window (TPT) Systems According to various embodiments, a TPT system includes three main components: (i) a light delivery module for delivering diffuse light in transmission-mode through the skull to the brain, (ii) an acoustic detection module with an ultrasonic transducer device for detecting acoustic waves through an acoustic window, and (iii) a data acquisition module for recording acoustic signals from the ultrasonic transducer device. In some embodiments, the light delivery module includes a diffuser for diffusing a laser beam from one or more laser sources, which may be separate from, or part of, the TPT system.

FIG. 1 depicts a schematic illustration of a transmission-mode photoacoustic tomography of the brain through an acoustic window (TPT) technique, according to embodiments. The illustrated example includes components of a TPT system 100 at an instant in time during operation. TPT system 100 includes a light delivery module 110 with a diffuser 116 and an acoustic detection module 150 with an ultrasonic transducer device 152 (also referred to herein as an "ultrasonic transducer probe"). Diffuser 116 is configured to diffuse a laser beam 102 from an external laser source (e.g., optically communicated via optical fiber or one or more mirrors) to generate diffuse light 117, which is substantially conical in shape. Light delivery module 110 delivers the diffuse light 117 in transmission mode through a skull 120 to a volumetric region of interest 121 in the brain. For simplicity, the volumetric region of interest 221 is depicted as an ellipsoid volumetric shape. It would be understood that the other volumetric shapes may be illuminated.

In FIG. 1, diffuser 116 is shown with free space (i.e., no intervening scattering matter) between an outer surface of skull 120 and an outer surface of the diffuser 116. In other implementations, the diffuser 116 may be located at other distances from, or in contact with, the skull 120. During operation, the tissues in the volumetric region of interest 121 absorb and convert diffuse light 117 into acoustic waves 154 via the photoacoustic effect. Ultrasonic transducer device 152 is located in close proximity to an acoustic window 124 (e.g., a temporal region) in the skull 120 to detect acoustic waves 154 through the acoustic window 124. For an ultrasonic transducer device that is a small handheld array, the ultrasonic transducer device may be placed within 1 inch of the acoustic window according to one implementation. For an ultrasonic transducer device that is a larger hemispherical array with a large field-of-view, the distance between the acoustic window and the array can be much larger, such as 15 cm. In other implementations, ultrasonic transducer device 152 may be placed in contact with, in closer proximity to, or at a further distance from skull 120. In implementations where there is a distance between the contact surface of ultrasonic transducer device 152 and the outer surface of skull 120, an acoustic medium such as an acoustic gel or water may be located therebetween. In FIG. 1, light is delivered to a first side of the skull 120 and acoustic window 124 is on a second side of the skull 120 opposite the first side. Diffuser 116 has a central axis 118. The cone of diffuse light 117 is shown with a central axis 118 coinciding with a central axis of the diffuser 116. In this example, diffuser 116 is positioned during operation such that central axis 118 intersects acoustic window 124.

TPT system 100 also includes a data acquisition module (e.g., data acquisition module 280 in FIG. 1) that can record the acoustic signals from ultrasonic transducer device 152. The data from the recorded acoustic signals may be used to reconstruct (e.g., using a universal back projection procedure) one or more photoacoustic images such as, e.g., a series of two-dimensional slices and/or a volumetric photoacoustic image.

Figure 2:
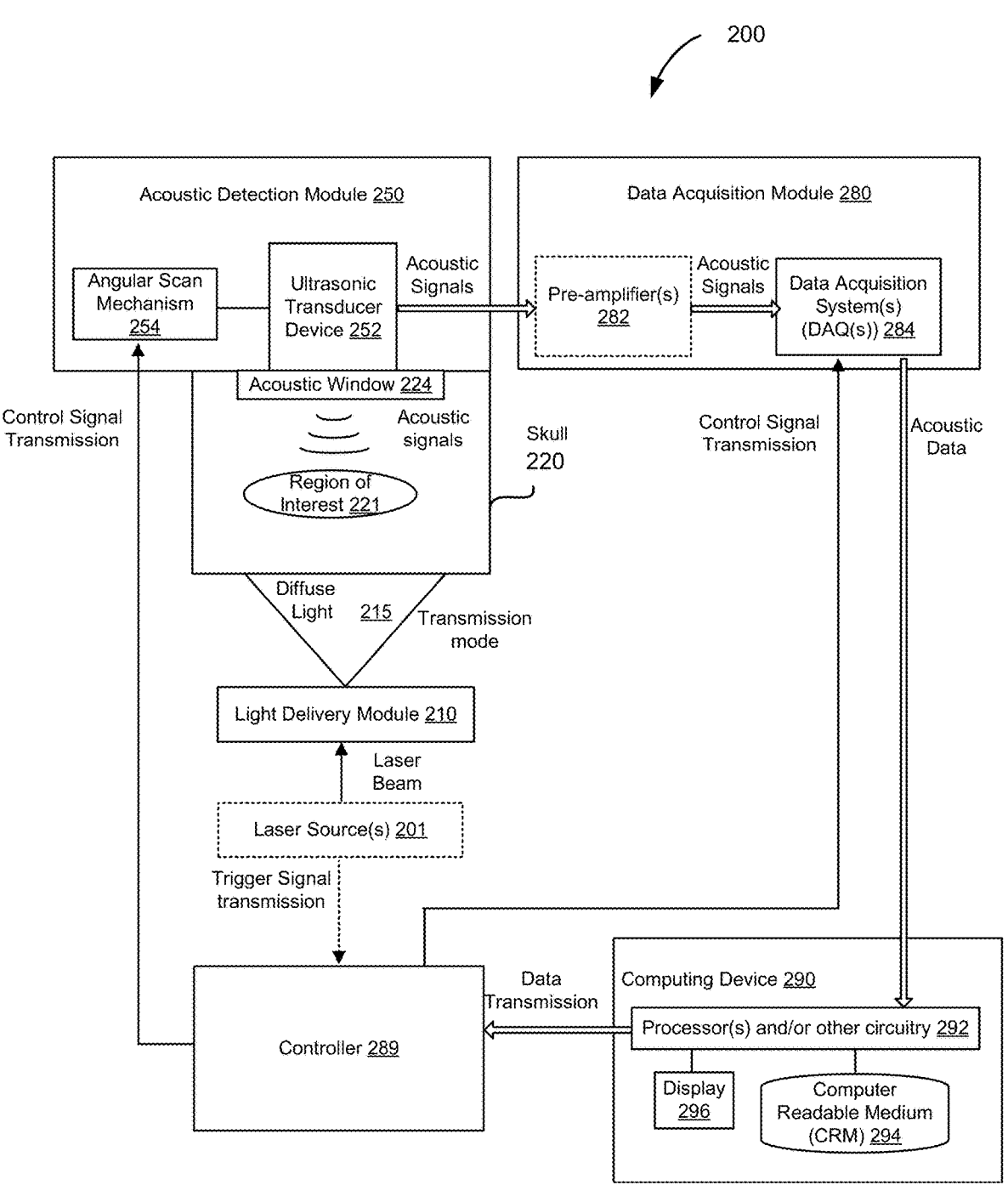
FIG. 2 depicts a block diagram of components of a TPT system, according to various embodiments.

FIG. 2 depicts a block diagram of a TPT system 200, according to various implementations. TPT system 200 includes a light delivery module 210 for delivering diffuse light 215 in transmission-mode through a skull 220 to a volumetric region of interest 221 being imaged in the brain. The light delivery module 210 is in optical communication with (e.g., via one or more mirrors) one or more optional (denoted by dashed line) laser sources 201 to receive a laser beam. Light delivery module 210 may include a diffuser configured to diffuse the laser beam. At the instant in time shown in FIG. 2, skull 220 is present to receive diffuse light 215 during data acquisition. It would be understood that at other times skull 220 may not be present.

In various implementations, the light delivery module includes a diffuser configured to receive a laser beam via one or more optical components (e.g., mirror(s), optical fiber(s) such as, e.g., a fiber bundle, optical connector(s), beam splitter(s), relay(s), lens(es), beam combiner(s), filter(s), beam steering device(s), relay(s), etc.) from one or more laser sources or from one or more high power light emitting diodes (LEDs). The laser source(s) may be part of the light delivery system or separate from the light delivery system. Although many examples herein employ a laser beam from one or more laser sources, in other implementations, a light beam from one or more other light sources (e.g., LEDs) may be used.

In various implementations, the diffuser may diffuse or scatter the laser beam or other light beam to evenly distribute the light to generate diffuse light at or below, e.g., the American National Standards Institute (ANSI) safety limit or other safety limit. Some examples of suitable diffusers include a ground glass diffuser, an engineered diffuser, etc. Although the light delivery module of several examples herein employs a diffuser, in alternative implementations, a concave lens may also be used to expand the light.

In various aspects, the laser source(s) (e.g., a pulsed laser) is/are configured to generate pulsed or modulated illumination such as, e.g., pulsed or modulated light. In one example, a laser source may be a pulsed laser that can generate a 1064-nm laser beam. As another example, a laser source may be a pulsed laser that can generate pulses having a wavelength in a range from about 700 nm to about 1000 nm. As another example, a laser source may be a pulsed laser that can generate pulses having wavelength in a range from about 600 nm to about 1100 nm. In yet another example, a laser source may be a pulsed laser that can generate pulses with wavelength greater than 760 nm. In yet another example, a laser source may be a pulsed laser that can generate pulses with wavelength greater than 1000 nm. A commercially-available example of a suitable pulsed laser is the PRO-350-10, Quanta-Ray® laser with a 10-Hz pulse repetition rate and 8 ns-12 ns pulse width sold by Spectra-Physics®. The low optical attenuation of 1064 nm light or other near infrared light can be used to deeply penetrate to, e.g., a depth of 4 cm, into biological tissues. Imaging of biological tissues using near infrared light is discussed in Smith, A. M., Mancini, M. C. & Nie, S., "Bioimaging: second window for in vivo imaging," *Nat. Nanotechnol.* 4, 710-711 (2009), which is hereby incorporated by reference in its entirety. Alternatively, a laser source may be a continuous wave laser source that is chopped, modulated and/or gated.

In implementations that include a laser source in the form of a pulsed laser, the pulse repetition rate may be about 10-Hz in some cases, about 20-Hz in other cases, about 50-Hz in other cases, and about 100-Hz in other cases. In another case, the pulse repetition rate is in a range from about 10-Hz to about 100-Hz.

In one aspect, the one or more laser sources may include a tunable narrow-band pulsed laser such as, e.g., one of a quantum cascade laser, an interband cascade laser, an optical parametric oscillator, or other pulsed laser that can be tuned to different narrow bands (e.g., a near-infrared band). In another aspect, the one or more laser sources may include a pulsed laser of a single wavelength or approximately a single wavelength.

In one aspect, the one or more laser sources may include multiple lasers of the same type. In another aspect, the one or more laser sources may include a combination of different types of lasers. For example, an optical parametric oscillator combined with an Nd:YAG laser may be used in one implementation.

Returning to FIG. 2, TPT system 200 includes an acoustic detection module 250 having an ultrasonic transducer device 252 for sampling induced acoustic signals through an acoustic window 220 in skull 220. In one implementation, ultrasonic transducer device 252 is in contact with, or in close proximity to, skull 220 during acoustic signal acquisition, which can advantageously minimize acoustic distortion. Acoustic detection module 250 also includes an angular scan mechanism 254 coupled to ultrasonic transducer device 252 for rotating ultrasonic transducer device 252 while the ultrasonic transducer device 252 detects acoustic signals at a plurality of different planes in the three-dimensional imaging field-of-view.

In various implementations, the acoustic detection module includes an ultrasonic transducer device with one or more transducer elements (sometimes referred to herein as "transducers") operable to detect acoustic signals over time. The one or more transducer elements may be in various arrangements such as, e.g., a single-element transducer, one or more linear arrays, one or more arc-shaped arrays, a two-dimensional (2D) matrix array, a hemispherical array, etc. Each transducer element has an aperture (e.g., a flat-rectangular aperture) with an aperture size (e.g., height of about 2 mm, about 5 mm, in a range of 2 mm to 10 mm, etc. and a width of about 2 mm, about 0.65 mm, in a range of 1.20 mm-1.50 mm, etc.). The inter-element spacing may be less than or equal to about 1.0 mm in one aspect, less than or equal to 0.7 mm in one aspect, less than or equal to 1.5 mm in one aspect, or less than or equal to 2.0 mm in one aspect. In one aspect, the inter-element spacing is in a range of 0 mm to about 5 mm. An example of a suitable ultrasonic device is an ATL P4-2 phased linear array ultrasound probe with 64 transducer elements, 2 cm aperture size, and 2.5 MHz center frequency.

In some aspects, an ultrasonic transducer device may have one or more unfocused transducer elements. In one case, each of the unfocused transducer elements has a central frequency in a range of 0.50 MHz to 2.25 MHz and a one-way bandwidth of more than 50%. In another aspect, each of the unfocused transducer elements has a central frequency in a range of 2.25 MHz to 10 MHz and a one-way bandwidth of more than 50%. In some aspects, the ultrasonic transducer device may include one or more unfocused transducer elements that have diffraction angle, e.g., of about 10 degrees, in a range of about 5 degrees to about 30 degrees, of about 20 degrees, in a range of about 5 degrees to about 30 degrees, etc.

In certain implementations, during operation the ultrasonic transducer device is placed in contact with, or in close proximity to, the skull or to the brain which may advantageously reduce acoustic distortion. For example, the ultrasonic transducer device may be placed in close proximity (e.g., within 0.1 cm, within 0.2 cm, within 0.3, cm, within 0.4 cm, etc.) to an outer surface (e.g., at the scalp) of the skull. In one example, the ultrasonic transducer device may be placed directly on the brain, e.g., during brain surgery. Placing the ultrasonic transducer device in contact with, or in close proximity to, the skull or brain may avoid the need to use water or other acoustic medium (e.g., acoustic gel) that might absorb and reduce the acoustic signals transmitted.

In various implementations, the acoustic detection module includes an angular scan mechanism coupled to the ultrasonic transducer device to be able to rotate ultrasonic transducer device while the ultrasonic transducer device detects acoustic signals over time at a plurality of different planes in a three-dimensional imaging field-of-view. The angular scan mechanism may rotate along one or two rotational axes. In some cases, the angular scan mechanism may hold the ultrasonic transducer device at each of multiple positions for a period of time, e.g., about 10 seconds, about 15 seconds, about 20 seconds, in a range of about 10 seconds to about 20 seconds, etc. In one implementation, the angular scan mechanism can rotate the ultrasonic transducer device (also referred to herein as an "ultrasonic transducer probe" or "probe") about the azimuthal axis (that goes across the transducer elements of the probe) at the imaging end of the probe between angles of +30 and −30 degrees.

Returning to FIG. 2, TPT system 200 also includes a data acquisition module 280 with one or more optional (denoted by dashed line) pre-amplifiers 282 for amplifying acoustic signals (sometimes referred to herein as "photoacoustic signals") communicated from ultrasonic transducer device 252. Data acquisition module 280 also includes one or more data acquisition systems (DAQs) 284 for processing (e.g., digitizing and/or recording) acoustic signals received from the optional pre-amplifier(s) 282 or directly from ultrasonic transducer device 252 in implementations without pre-amplifier(s) 282. In one aspect, DAQ(s) 284 include at least one digitizer to digitize the acoustic signals.

In certain implementations, DAQ(s) 284 may be configured to record an acoustic signal after each laser light pulse excitation. In some cases, acoustic signals are recorded within a time period after each laser pulse excitation such as, e.g., within 100 μs, after each laser pulse.

In various embodiments, a TPT system includes a data acquisition module with one or more DAQ(s) configured to record acoustic signals from the ultrasonic transducer device. In some cases, the data acquisition module may also include one or more pre-amplifiers for amplifying the acoustic signals from the ultrasonic transducer device. An example of a suitable DAQ is a 128-channel system (e.g., SonixDAQ made by Ultrasonix Medical ULC with 40 MHz sampling rate, 12-bit dynamic range, and programmable amplification up to 51 dB), which may be configured to be in electrical communication with four 128-channel pre-amplifiers. The acoustic signals may be sampled at various frequencies. In one example, the sampling frequency is in a range from about 4 MHz to about 100-Hz. In another example, the sampling frequency is 40 MHz.

According to one aspect, the one or more DAQs and one or more pre-amplifiers of a TPT system provide one-to-one mapped associations with the transducers in the ultrasonic transducer device. These one-to-one mapped associations allow for fully parallelized data acquisition of all ultrasonic transducer channels and avoids the need for multiplexing after each laser pulse excitation or other modulated or pulsed excitation illumination. With one-to-one mapped associations between pre-amplifiers and transducer elements, each transducer element is in electrical communication with one dedicated pre-amplifier channel (also referred to as "preamp channel"). The one dedicated pre-amplifier channel is configured to amplify only acoustic signals detected by the one associated/mapped ultrasound transducer. These one-to-one mapped associations between the transducers and the pre-amplifier channels allow for parallelized pre-amplification of the acoustic signals detected by the plurality of transducers in the ultrasound transducer device. With one-to-one mapped analog-to-digital sampling, each pre-amplifier is operatively coupled to a corresponding dedicated data channel of an analog-to-digital sampling device in a DAQ to enable parallelized analog-to-digital sampling of the plurality of pre-amplified PA signals. The pre-amplified PA signals produced by each individual preamp channel are received by a single dedicated data channel of the at least one analog-to-digital sampling devices. Any suitable number of pre-amplifier devices and/or DAQ devices may be used to provide the one-to-one mapping.

Each of the one or more pre-amplifiers of a TPT system may be set to a pre-amplifier gain that may be determined by one or more factors. For example, the pre-amplifier gain may be determined based on one or more of a minimum signal-to-noise ratio and one or more operating parameters of the data acquisition and processing system components such as analog-to-digital sampling devices (digitizers) of the DAQs, signal amplifiers, buffers, and the computing device. In one aspect, the pre-amplifier gain is in a range that is high enough to enable transmission of the acoustic signals with minimal signal contamination, but below a gain that may saturate the dynamic ranges of the DAQs used to digitize the acoustic signals amplified by the pre-amplifier(s). In certain aspects, the gain of the plurality of pre-amplifier channels may be at least about 5 dB, at least about 7 dB, at least about 9 dB, at least about 11 dB, at least about 13 dB, at least about 15 dB, at least about 17 dB, at least about 19 dB, at least about 21 dB, at least about 23 dB, at least about 25 dB, or at least about 30 dB.

Returning to FIG. 2, TPT system 200 also includes a computing device 290. Some examples of suitable computing devices that can be used included a personal computer, an embedded computer, a single board computer (e.g., Raspberry Pi or similar), a portable computation device (e.g., tablet), a controller, or any other computation device or system of devices capable of performing the functions described herein. Computing device 290 includes one or more processors and/or other circuitry 292 in electrical communication with DAQ(s) 284 to receive photoacoustic data. The one or more processors (e.g., GPU) and/or other circuitry 292 are configured to perform operations such as image reconstruction, image analysis, and/or generating control instructions. Computing device 290 also includes a display 286 and a computer readable media (CRM) 294, both in electrical communication with the one or more processors and/or other circuitry 292. During operation, digitized radio frequency data from the DAQ(s) 284 may be first stored in an onboard buffer, and then transferred to computing device 290, e.g., through a universal serial bus 2.0.

Computing device 290 includes instructions residing on CRM 294 that can be executed to perform functions of TPT system 200 such as image reconstruction, image analysis, and generating control instructions and/or sending control signal transmissions. CRM 294 may be a non-transitory computer readable media. In certain implementations, the processors and/or other circuitry 292 may execute instructions to perform one or more of: 1) communicating control instructions or control signals to one or more components of TPT system 100, 2) perform reconstruction operations to reconstruct one or more two-dimensional or three-dimensional volumetric images of a field-of view using the photoacoustic data, and/or 3) analyze the one or more reconstructed images, e.g., to evaluate a brain function. For example, the processors and/or other circuitry 292 and/or one or more external processors may execute instructions that communicate control signals to the angular scan mechanism 254 to rotate the ultrasonic transducer device 252 about one or more rotational axes and send control signals to DAQ(s) 284 to simultaneously record acoustic signals received by ultrasonic transducer device 252.

TPT system 200 also includes a controller 289 in electronic communication with the DAQ(s) 284 and angular scan mechanism 254 to send control signals. The control signals may be based on control instructions communicated by the computing device 290. Controller 289 may include one or more processors. Controller 289 is in electrical communication with angular scan mechanism 254, computing device 290, and optionally laser source(s) 201. In certain implementations, controller 289 synchronizes functions of one or more components of TPT system 200. For example, controller 289 may synchronize the acoustic signal acquisition, light beam pulses, and/or rotation of ultrasonic transducer device 252 by sending control signals to DAQ(s) 284 and angular scan mechanism 254 in response to receiving trigger signals from laser source(s) 201. In another implementation, controller 289 synchronizes the acoustic signal acquisition, light beam pulses, and/or rotation of ultrasonic transducer device 252 by sending control signals to DAQ(s) 284, angular scan mechanism 254, and optional laser source (s) 201. Although not shown, controller 289 may also be in electronic communication with pre-amplifier(s) 282 to send control signal(s), e.g., to adjust amplification. Computing device 290 is in electrical communication with the controller 289 to transmit control instructions.

The electrical communication between system components of TPT system 200 may be in wired and/or wireless form. One or more of the electrical communications between components of the TPT system 200 may be able to provide power in addition to communicate signals.

Although certain components are illustrated in FIG. 2 as being included in TPT system 200, it should also be appreciated that in other implementations one or more of the illustrated components may be omitted. For example, in an alternate implementation, controller 289 may be omitted and control signals are sent directly from computing device 290. As another example, controller 289 and computing device 290 may be omitted in an alternate implementation. In this example, the data acquisition module may include one or more processors that perform various functions of TPT system 200 such as image processing and control of system components.

In some implementations, a TPT system (e.g., TPT system 200 in FIG. 2) may include one or more communication interfaces (e.g., a universal serial bus (USB) interface). Communication interfaces can be used, for example, to connect various peripherals and input/output (I/O) devices such as a wired keyboard or mouse or to connect a dongle for use in wirelessly connecting various wireless-enabled peripherals. Such additional interfaces also can include serial interfaces such as, for example, an interface to connect to a ribbon cable. It should also be appreciated that the various system components can be electrically coupled to communicate with various components over one or more of a variety of suitable interfaces and cables such as, for example, USB interfaces and cables, ribbon cables, Ethernet cables, among other suitable interfaces and cables.

Figure 3:
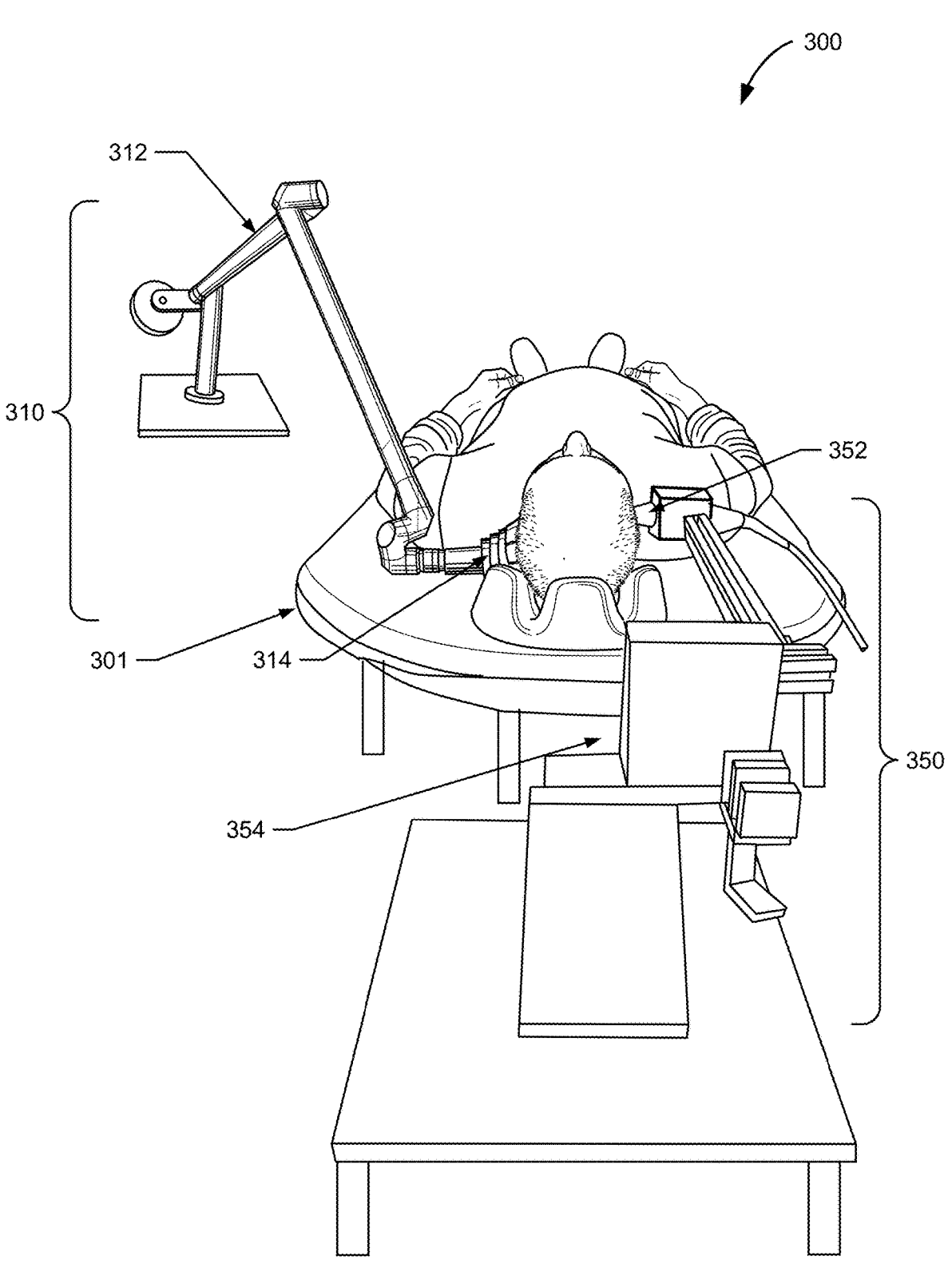
FIG. 3 depicts a drawing of a perspective view of a TPT system of an in-vivo imaging configuration, according to an embodiment.

FIG. 3 depicts a drawing of a perspective view of a TPT system 300 of an in-vivo imaging configuration, according to an embodiment. At the instant in time depicted, a human subject being imaged is lying on an examination table 301 during acoustic signal acquisition. In other implementations, the human subject may be sitting in a chair, standing, etc.

TPT system 300 includes a light delivery module 310 for delivering diffuse light in transmission-mode through a skull of the human subject to a volumetric region in the brain. Light delivery module 310 includes a laser articulating arm 312 and a diffuser and photon recycling device 314 coupled to an end of the laser articulating arm 312. The laser articulating arm 312 includes one or more mirrors for reflecting a laser beam from a laser source to a diffuser of the diffuser and photon recycling device 314. The diffuser may spread the light of the laser beam to generate diffuse light below or at an ANSI safety limit or other safety limit. The laser articulating arm 312 includes a series of linear portions with a joint between adjacent linear portions that allow for two degrees of rotational movement at each joint. A proximal end of the laser articulating arm 312 includes an aperture for receiving the laser beam and the distal end of the laser articulating arm 312 has an opening in optical communication with the diffuser.

The diffuser and photon recycling device 314 also includes a photon recycling element for receiving light reflected from the skull and reflecting the light back to the skull, which advantageously may increase photons delivered to the volumetric region of interest. The diffuser and photon recycling device 314 includes a truncated cone shaped housing with a photon recycling element on an inner surface and a diffuser in optical communication with the laser source via the at least one mirror in the joints of the light articulating arm 312. During data acquisition, the truncated cone shaped housing is placed in contact with the skull such that its conical end may be substantially surrounding and containing a portion of the skull. In one implementation, diffuser and photon recycling device 314 may also be positioned such that a central axis of the diffuser intersects the acoustic window.

TPT system 300 also includes an acoustic detection module 350 having an ultrasonic transducer device 352 for sampling acoustic signals from a three-dimensional field-of-view through an acoustic window in the skull. Ultrasonic transducer device 352 may be placed in contact with, or in close proximity to, the skull during acoustic signal acquisition. Acoustic detection module 350 also includes an angular scan mechanism 354 coupled to ultrasonic transducer device 352 for rotating ultrasonic transducer device 352 during operation to be able detect acoustic signals at a plurality of different planes. In this example, the ultrasonic transducer device 352 is a linear array ultrasound probe (e.g., ATL P4-2 phased linear array ultrasound probe). TPT system 300 may also include a data acquisition module (e.g., data acquisition module 280 in FIG. 2) with one or more data acquisition systems for recording acoustic signals from ultrasonic transducer device 352.

In an alternate implementation, TPT system 300 may also include a controller (e.g., controller 289 in FIG. 2) for sending control signals to system components, and/or a computing device (e.g., computing device 290 in FIG. 2) for performing functions of TPT system 300 such as image reconstruction and/or image analysis.

Figure 4A:
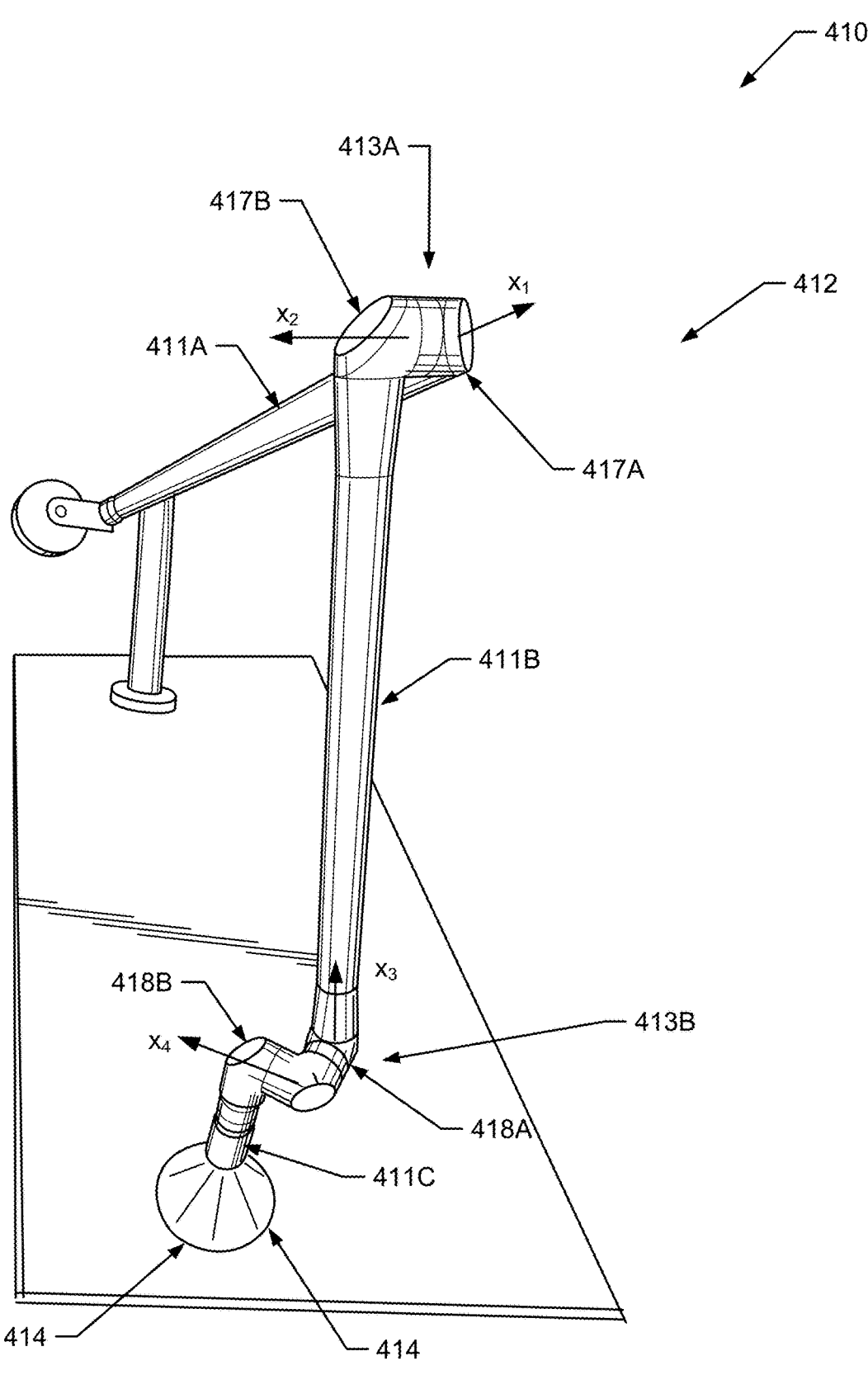
FIG. 4A depicts a drawing of a perspective view of a light delivery module with a laser articulating arm and a diffuser and photon recycling device coupled to a distal end of the laser articulating arm, according to an embodiment.
Figure 5A:
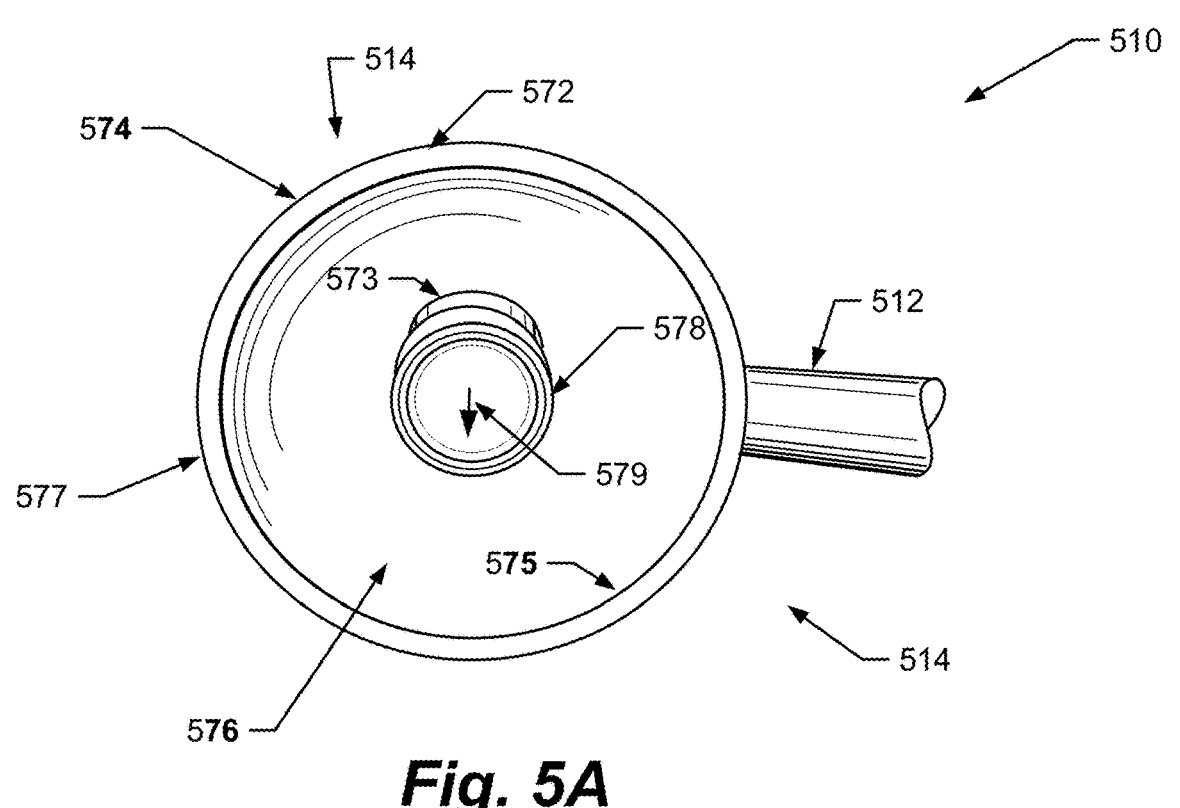
FIGS. 5A and 5B depict drawings of perspective and side views respectively of a portion of a light delivery module, according to an embodiment.
Figure 5B:
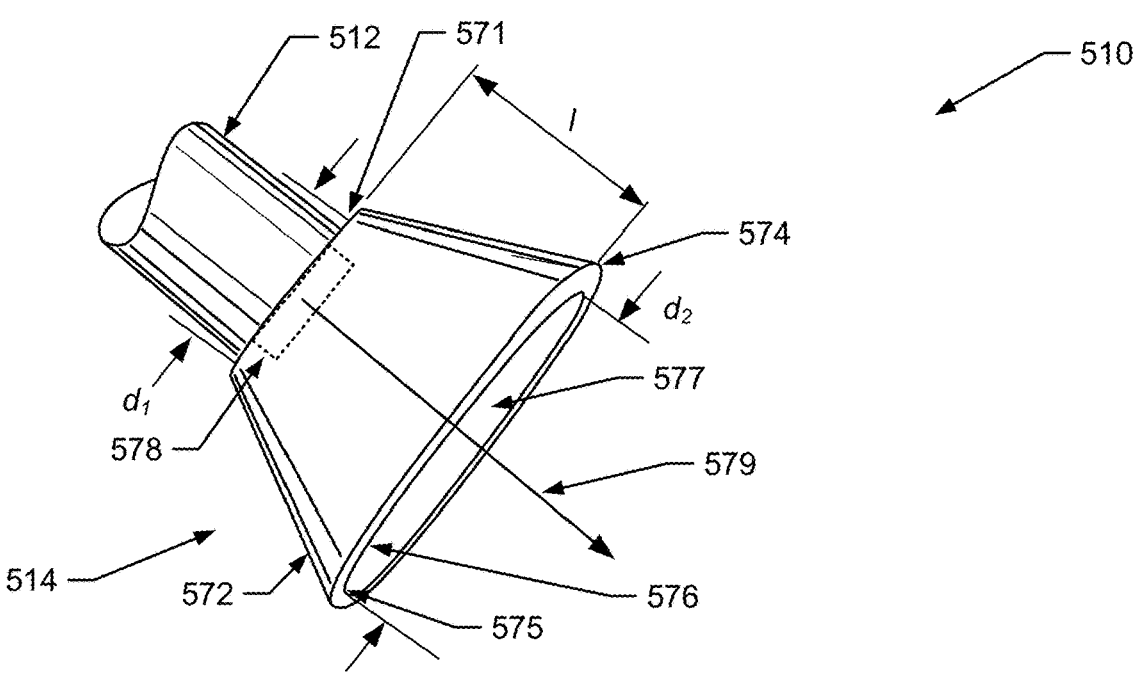
Figure 7:
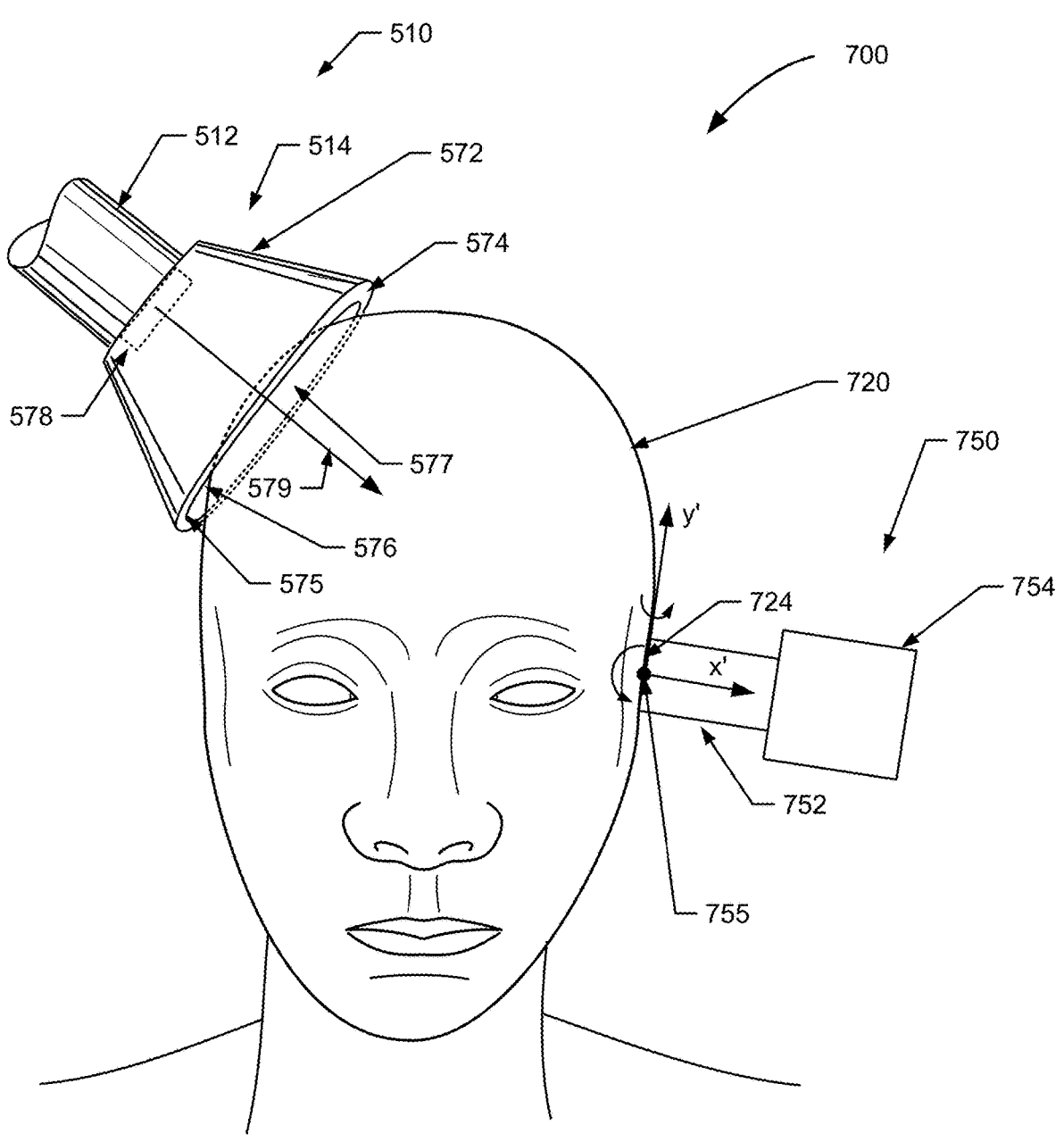
FIG. 7 depicts components of light delivery module in FIGS. 5A and 5B and components of an acoustic detection module, according to an embodiment.

Some of the elements of laser articulating arm 412 in FIG. 4A are similar or analogous to elements of laser articulating arm 312 shown in FIG. 3. For the sake of brevity, the discussion of such similar or analogous elements with regard to FIG. 3 may be assumed to be equally applicable, unless indicated otherwise, to the similar or analogous counterparts of those elements in FIG. 4A. Also, some of the elements of diffuser and photon recycling device 514 in FIGS. 5A and 5B are similar or analogous to elements of diffuser and photon recycling device 314 shown in FIG. 3. For the sake of brevity, the discussion of such similar or analogous elements with regard to FIG. 3 may be assumed to be equally applicable, unless indicated otherwise, to the similar or analogous counterparts of those elements in FIGS. 5A and 5B. In addition, some of the elements of acoustic detection module 750 in FIG. 7 are similar or analogous to elements of acoustic detection module 350 shown in FIG. 3. For the sake of brevity, the discussion of such similar or analogous elements with regard to FIG. 3 may be assumed to be equally applicable, unless indicated otherwise, to the similar or analogous counterparts of those elements in FIG. 7.

A. Light Delivery Module

In various embodiments, a TPT system includes a light delivery module that can deliver diffuse light in transmission-mode through the skull to a volumetric region of the brain. In various embodiments, a light delivery module includes a laser articulating arm and a diffuser and photon recycling device coupled to an end of the laser articulating arm. In an alternative embodiment, a light delivery module includes a fiber bundle coupled at one end to a laser source. In another alternative embodiment, a light delivery module involves a free-space approach where a laser source is directed to provide a laser beam through free space to a diffuser.

Laser Articulating Arm and Diffuser and Photon Recycling Device Example

In various embodiments, a TPT system includes a light delivery module (e.g., light delivery module 410 in FIG. 4A) with a light articulating arm, a diffuser and photon recycling device coupled to a distal end of the light articulating arm, which enables safe, efficient, and flexible delivery of light at, or below, the American National Standards Institute (ANSI) safety limit or other safety limit. The diffuser and photon recycling device can be located directly on the scalp or the brain for direct delivery of diffuse light, which avoids the need for an acoustic coupling medium (e.g., water, acoustic gel, etc.) advantageously overcoming the issue of absorption of light (e.g., 1064 nm light) by the acoustic coupling medium. Also, the diffuser and photon recycling device can recycle photons reflected from the skull/brain which advantageously enhances light transmittance through the skull. By utilizing these features, the light delivery module of these embodiments may enable operation at the safety limit of light delivery resulting in improved performance and data quality as compared to reflection mode systems which involve large water propagation distances.

In FIG. 4A, a light delivery module 410 includes a light delivery module 410 with a laser articulating arm 412 and a diffuser and photon recycling device 414 coupled to a distal end of the laser articulating arm 412, according to an embodiment. The laser articulating arm 412 is optically coupled (e.g., through an aperture) at a proximal end to a laser source which enables efficient and flexible light delivery to tissue. The diffuser and photon recycling device 414 includes an engineered diffuser 478 (in FIG. 4B) to expand the laser beam to be within the ANSI safety limit or other safety limit (e.g., lower than ANSI safety limit). The diffuser and photon recycling device 414 includes a truncated cone shaped housing 472 that serves at least two purposes. Firstly, it shields and contains the light. Secondly, it performs photon recycling by reflecting the light that is diffusely or specularly reflected from the skin, thus increasing the light transmittance through the skull. This example design allows for direct delivery of light to the skin surface, thus avoiding the problem of water absorption of light at 1064 nm.

As shown in FIG. 4A, laser articulating arm 412 includes a first linear segment 411A, a second linear segment 411B, and a third linear segment 411C. The segments 411A, 411B, and 411C are coupled in series by a first joint 413A between first linear segment 411A and second linear segment 411B and a second joint 413B between second linear segment 411B and third linear segment 411C. The first joint 413A includes a first rotatable portion 417A rotatable about axis $x_1$ and a second rotatable portion 417B rotatable about an axis $x_2$. The second joint 413B includes a first rotatable portion 418A rotatable about axis $x_3$ and a second rotatable portion 418B rotatable about an axis $x_4$. The third linear segment 411C is coupled at an end to diffuser and photon recycling device 414. Each segment 411A, 411B, and 411C includes an internal cavity or space and an outer light insulated housing. Each of the joints 413A, 413B includes at least one mirror for reflecting the laser beam from one linear segment to the adjacent linear segment. The joints 413A, 413B also include a light insulated housing. First rotatable portion 417A of joint 413A includes a mirror for reflecting the laser beam from first linear segment 411A to second rotatable portion 417B. Second rotatable portion 417B of joint 413A includes a mirror for reflecting the laser beam from second rotatable portion 417B to second linear segment 411B. First portion 418A of joint 413B includes a mirror for reflecting the laser beam from second linear segment 411B to second rotatable portion 418B. Second portion 418B of joint 413B includes a mirror for reflecting the laser beam from first rotatable portion 418A to third linear segment 411C.

Figure 4B:
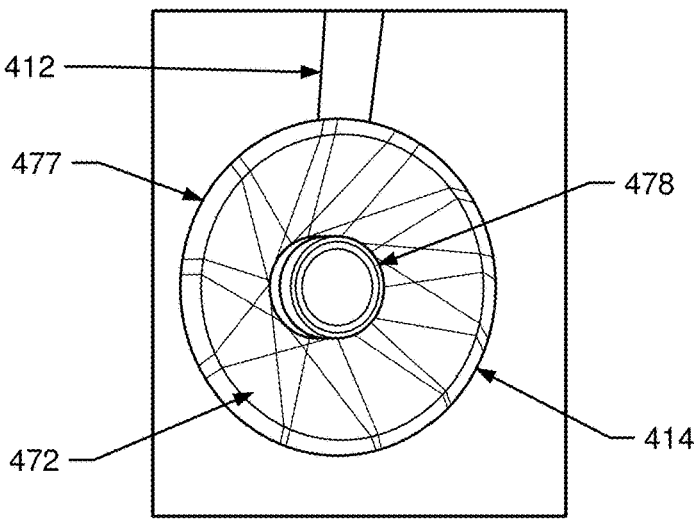
FIG. 4B is a photograph of the diffuser and photon recycling device in FIG. 4A.

FIG. 4B is a photograph the diffuser and photon recycling device 414 in FIG. 4A. The diffuser and photon recycling device 414 includes an engineered diffuser 478 to expand the laser beam to be within the ANSI safety limit or other safety limit (e.g., lower than ANSI safety limit). Diffuser and photon recycling device 414 also includes a photon recycling element 477 for photon recycling by reflecting the light that is diffusely or specularly reflected from the skin, thus advantageously increasing the light transmittance through the skull. Photon recycling element 477 includes a truncated cone shaped housing 472.

Figure 4C:
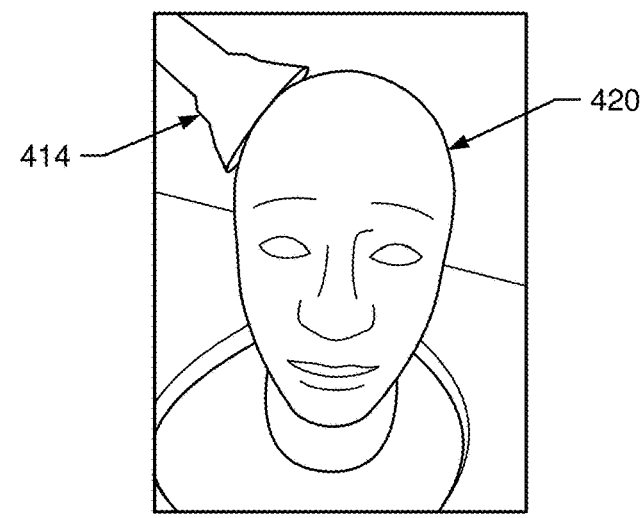
FIG. 4C is a photograph of the diffuser and photon recycling device in FIG. 4A shown being placed in direct contact with a human head model skull.

FIG. 4C is a photograph of the diffuser and photon recycling device 414 in FIG. 4A shown being placed in direct contact with a human head model skull 420 to allow for direct delivery of light of light to the skin surface.

Figure 4D:
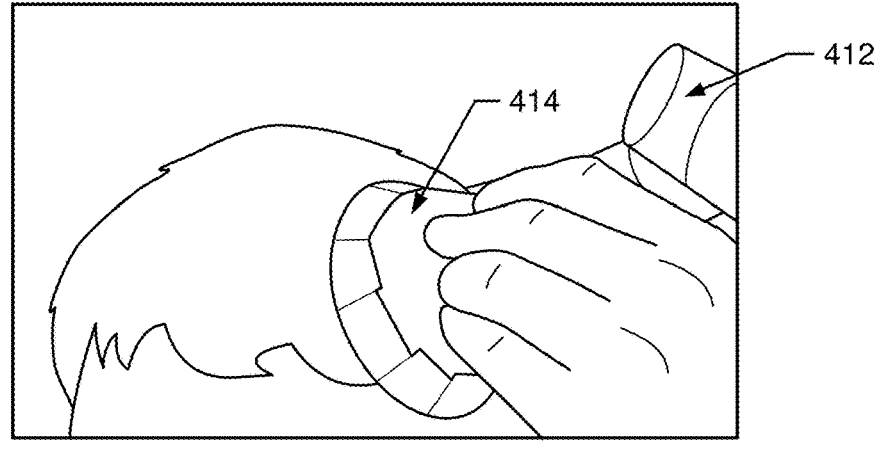
FIG. 4D is a photograph of the diffuser and photon recycling device in FIG. 4A being placed in direct contact with the skin of a human subject.

FIG. 4D is a photograph of the diffuser and photon recycling device 414 in FIG. 4A being placed in direct contact with the skin of a human subject to allow for direct delivery of light of light to the skin surface, which avoids the need for an acoustic coupling medium advantageously overcoming the issue of absorption of light (e.g., 1064 nm light) by the acoustic coupling medium. As shown, the diffuser and photon recycling device 414 is coupled to a distal end of laser articulating arm 412 to enable safe, efficient, and flexible delivery of light at, or below, the American National Standards Institute (ANSI) safety limit or other safety limit.

FIGS. 5A and 5B depict drawings of perspective and side views respectively of a portion of a light delivery module 510, according to an embodiment. Light delivery module 510 includes a diffuser and photon recycling device 514 coupled to a distal end of a laser articulating arm 512 for flexible delivery of light. Diffuser and photon recycling device 514 includes an engineered diffuser 578 to expand the laser beam to be within the ANSI safety limit or other safety limit (e.g., lower than ANSI safety limit). Diffuser and photon recycling device 514 also includes a photon recycling element 577 configured to receive light reflected from the skull and reflect the light back to the skull which advantageously increases photons delivered. Photon recycling element 577 includes a truncated cone shaped housing 572 with an inner reflective surface 576. The inner reflective surface 576 may include a reflective film or coating. Truncated cone shaped housing 572 has a circular input end 571 having a first diameter, $d_1$ at an inner surface and a circular output end 574 with a circular inner edge 575 having a second diameter, $d_2$. Truncated cone shaped housing 572 has a length, l. Circular input end 571 also includes an aperture 573. In one implementation, the dimensions of the truncated cone shaped housing 572 are sized to reflect light to a region at a plane at the circular inner edge 575 of truncated cone shaped housing 572. During operation, Diffuser and photon recycling device 414 may be positioned to locate truncated cone shaped housing 572 in contact with the skull and also substantially surrounding a portion of the skull. The truncated cone shaped housing 572 serves to both shield and contain light and also perform photon recycling by reflecting the light that is diffusely or specularly reflected from the skin, thus may increase light transmittance through the skull. Moreover, this truncated cone shaped housing 572 allows for direct delivery of light to the skin surface, and thus does not require an acoustic medium between the skin surface and the ultrasonic transducer device which avoids the issue of absorption of light by the acoustic medium.

Some of the elements of laser articulating arm 512 in FIGS. 5A and 5B are similar or analogous to elements of laser articulating arm 412 shown in FIG. 4A. For the sake of brevity, the prior discussion of such similar or analogous elements with regard to FIG. 4A may be assumed to be equally applicable, unless indicated otherwise in the following discussion, to the similar or analogous counterparts of those elements in FIGS. 5A and 5B that share the same last two digits in their respective callouts as in FIG. 4A.

In various embodiments, a light delivery module includes a laser articulating arm and a diffuser and photon recycling device coupled to a distal end of the laser articulating arm. In these examples, the light articulating arm includes a plurality of segments (e.g., linear segments or curved segments) connected in series with a joint between each set of adjacent segments in the series. Each joint includes at least one mirror for reflecting the laser beam from one segment to the adjacent segment. Each segment may have an inner space or volume along at least a portion of its length through which the laser beam can propagate. The segments and joints have an outer casing that is light sealed i.e., made of material that reflects and/or absorbs wavelength of the laser beam. Some examples of materials include aluminum, stainless steel, etc. In one implementation, a joint includes a first portion and a section coupled to ends of first and second adjacent segments respectfully. First portion is rotatable about a first rotational axis and second portion is rotatable about a second rotational axis. Light articulating arm includes a proximal end with an aperture for receiving the laser beam from the laser source and a distal end in optical communication with a diffuser (also referred to herein as an "engineered diffuser") of the diffuser and photon recycling device. The diffuser is designed to expand the laser beam to be within the ANSI safety limit or other safety limit. In some cases, the laser articulating arm includes one or more spring or weight counterbalances to allow the arm to be folded back into a resting position. In some cases, the laser articulating arm includes one or more focusing lenses located within the inner space or volume of at least one of the segments that may compensate for laser beam divergence. In these embodiments, the diffuser and photon recycling device includes a photon recycling element which includes a housing with an reflective inner surface configured to receive light reflected from the skull (or brain in the implementation occurring during brain surgery) and reflect the light back to the skull, which advantageously may increase photons delivered to the volumetric region of interest. The photon recycling element may include, for example, a reflective film or coating on the inner reflective surface of the housing. Some examples of materials for the reflective film or coating include a sliver coating, a white reflective coating, etc. In one implementation, the housing is truncated cone shaped with a length, a circular input end with a first diameter, and a circular output end with edge having a second diameter. In one implementation, the dimensions of the housing may be sized to reflect the light back to a particular area of the skull. The housing serves to both shield and contain light and also perform photon recycling by reflecting the light that is diffusely or specularly reflected from the skin, thus may increase light transmittance through the skull. Moreover, this light delivery module allows for direct delivery of light to the skin surface, thus avoiding the need for acoustic medium. During data acquisition, the housing is placed in contact with the skull such that its circular end may be substantially surrounding a portion of the skull. In one implementation, diffuser and photon recycling device may also be positioned such that a central axis of the diffuser intersects the acoustic window.

Fiber Bundle Example

In one embodiment, the light delivery module includes a fiber bundle coupled at one end with a laser source or other light source.

Free Space Example

In one embodiment, a light delivery module involves a free-space approach where a laser source is directed to provide a laser beam or other light beam through free space to a diffuser.

C. Data Acquisition Module

In various embodiments, a TPT system includes an acoustic detection module configured to detect acoustic signals through an acoustic window in a skull over a three dimensional (3-D) field-of-view. The acoustic detection module is configured to be able to be placed directly on, or in close proximity to, the skin of the skull. The acoustic detection module includes an ultrasonic transducer device for detecting acoustic signals. The ultrasonic transducer device may be a single-element transducer, one or more linear arrays, one or more arc-shaped arrays, a two-dimensional (2D) matrix array, a hemispherical array, or other type of ultrasound probe. For example, the ultrasonic transducer device may be a linear array of transducer elements (e.g., ATL P4-2 phased linear array ultrasound probe with 64 transducer elements, 2 cm aperture size, and 2.5 MHz center frequency).

In some embodiments, the acoustic detection module includes an angular scan mechanism coupled to the ultrasonic transducer device to rotate the device to achieve the 3-D field-of-view. The angular scan mechanism includes a motor with a rotation center. In one implementation, to be able to combine the two-dimensional images from the acoustic signals detected by the ultrasonic transducer device, the ultrasonic transducer device is mounted at the rotation center of the motor of the angular scan mechanism to ensure that the probe surface is aligned with the rotation axis. Employing the angular scan mechanism enables the use of a relatively small probe surface area while achieving a larger field-of-view. In one implementation, for example, an ultrasonic transducer device in the form of a linear array ultrasound probe with 64 transducer elements with a surface area of 2 cm×2 cm was able to achieve an image field of view of 10 cm×10 cm at a depth of 12 cm. These embodiments may enable the capture of high-quality data while advantageously using a smaller and more cost-effective probe than traditional methods.

Figure 6A:
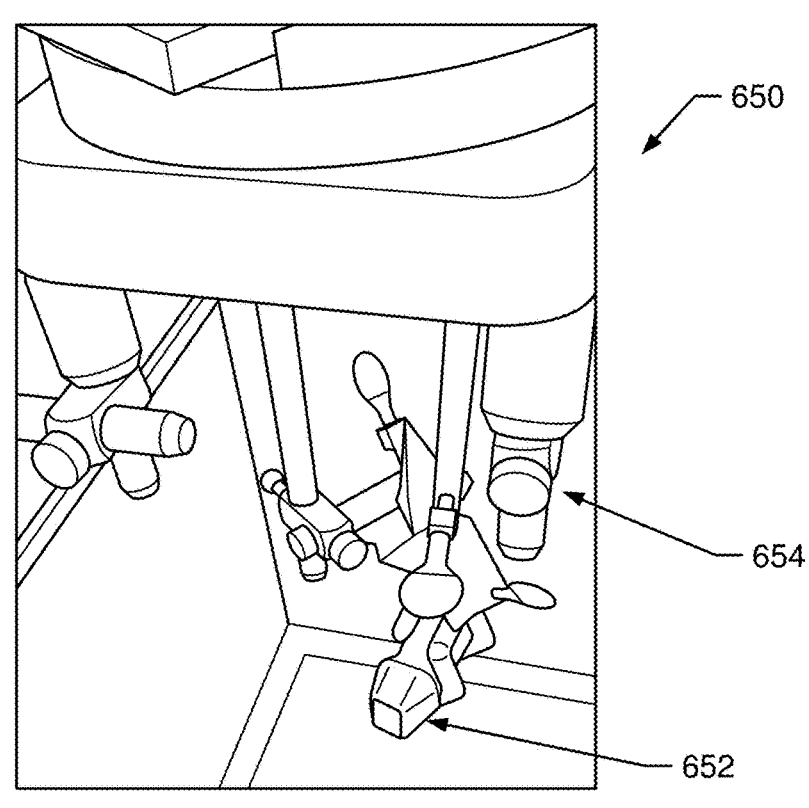
FIG. 6A is a photograph an acoustic detection module, according to an embodiment.

FIG. 6A is a photograph an acoustic detection module 650, according to an embodiment. Acoustic detection module 650 includes an angular scan mechanism 654 and an ultrasonic transducer device 652 mounted to angular scan mechanism 654. The angular scan mechanism 654 includes a motor that drives the rotation of the angular scan mechanism 654. During operation, the acoustic waves are detected by the ultrasonic transducer device 652 as the motor rotates the ultrasonic transducer device 652 in order to capture photoacoustic data that can be used to reconstruct one or more 3D images of a volumetric imaging field-of-view. In the illustrated embodiment, the ultrasonic transducer device 652 is a linear array of transducer elements (e.g., ATL P4-2 phased linear array ultrasound probe with 64 transducer elements, 2 cm aperture size, and 2.5 MHz center frequency). In other embodiments, other arrangements of one or more transducer elements may be used. In the embodiment shown in FIG. 6A, the angular scan mechanism 654 can rotate the ultrasonic transducer device 652 about the azimuthal axis at the imaging end of the probe between angles of +30 and −30 degrees.

Figure 6B:
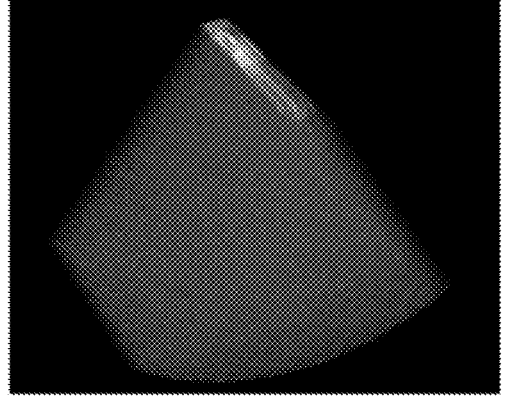
FIG. 6B is a 3D photoacoustic image captured by the acoustic detection module in FIG. 6A.

In one implementation, the acoustic detection module 650 shown in FIG. 6A may achieve an image field of view of 10 cm×10 cm at a depth of 12 cm. FIG. 6B is a 3D photoacoustic image captured by the acoustic detection module 650 in FIG. 6A. The field-of-view of the 3D image is 10 cm×10 cm×12 cm (azimuth×scan×depth).

Figure 6C:
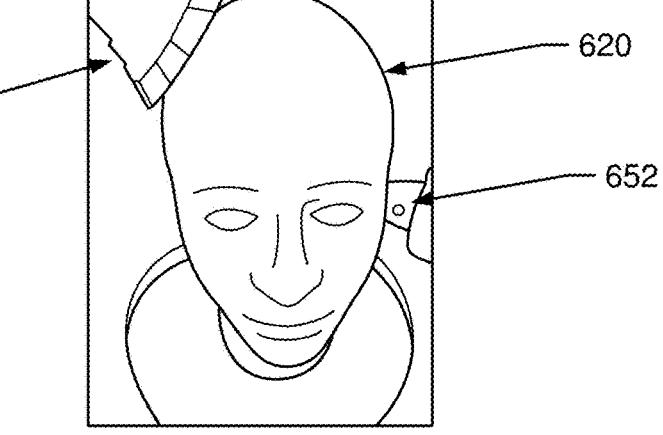
FIG. 6C is a photograph of the diffuser and photon recycling device from FIG. 4A being placed proximate, or in direct contact with, the skin surface of a human head model skull.

FIG. 6C is a photograph of the diffuser and photon recycling device 414 from FIG. 4A being placed proximate, or in direct contact with, the skin surface of a human head model skull 620 to demonstrate direct delivery of light of light to the skin surface and the acoustic detection module 650 from FIG. 6A proximate the skin surface of human head model skull 620 to demonstrate acoustic detection.

FIG. 7 depicts components of light delivery module 510 of FIGS. 5A and 5B and components of an acoustic detection module 750, according to an implementation. Light delivery module 510 is configured for direct delivery of light to the skin surface of a skull 720. Acoustic detection module 750 includes an ultrasonic transducer device 752 mounted to an angular scan mechanism 754. The ultrasonic transducer device 752 is a linear array of transducer elements (e.g., ATL P4-2 phased linear array ultrasound probe with 64 transducer elements, 2 cm aperture size, and 2.5 MHz center frequency). The angular scan mechanism 754 includes a motor with a rotation center 755. The ultrasonic transducer device 752 is mounted to angular scan mechanism 754 so that the surface of the ultrasonic transducer device 752 is at the rotation center 755 of the motor. The illustrated example includes a x'-axis and a y'-axis. The motor may rotate the ultrasonic transducer device 752 (i) about the y'-axis and/or (ii) about a z'-axis (not shown) that is orthogonal to a plane formed by x'-axis and y'-axis (i.e., normal to the page). For example, during an exemplary data acquisition process, the ultrasonic transducer device 752 is rotated by the motor of the angular scan mechanism 754 about the y'-axis and/or the z'-axis to capture acoustic signals over a volumetric field-of-view (azimuth×scan×depth).

In various embodiments, an acoustic detection module includes an angular scan mechanism and an ultrasonic transducer device mounted to the angular scan mechanism.

Some examples of angular scan mechanisms include mechanisms that can rotate the probe about any of the three axes drawn at the center of the ultrasonic transducer device. The angular scan mechanism includes a motor configured to rotate the ultrasonic transducer device about one or more two rotational axes. Various ranges of angles may be used. In one example, the motor rotates the ultrasonic transducer device 30 degrees. In another example, the motor rotates the ultrasonic transducer device 60 degrees. In another example, the motor rotates the ultrasonic transducer device 90 degrees.

III. TPT Imaging Methods

The TPT imaging methods described in this section can be used to obtain one or more two-dimensional images and/or one or more three-dimensional volumetric images. The operations of these TPT methods are performed by a TPT system (e.g., TPT system 100 in FIG. 1, TPT system 200 in FIG. 2, TPT system 300 in FIG. 3, or TPT system 700 in FIG. 7). The TPT system includes a light delivery module (e.g., light delivery module 510) for delivering diffuse light in transmission-mode through the skull to the brain and an acoustic detection module (e.g., acoustic detection module 750 in FIG. 7) with an ultrasonic transducer device for detecting acoustic waves through an acoustic window and an angular scan mechanism for rotating the ultrasonic transducer device.

FIG. 7 is a flowchart depicting a TPT imaging method, according to various implementations. At operation 810, using a light delivery module, diffuse light is delivered in transmission mode through a skull to the brain. For example, light delivery module may include a diffuser configured to diffuse or scatter a laser beam from a laser source or light sources to generate diffuse light at or below, e.g., the American National Standards Institute (ANSI) safety limit or other safety limit. In some cases, the light source may be controlled by a controller and/or other computing device. In one implementation, the light delivery module includes a photon recycling element (e.g., photon recycling element 577 in FIGS. 5A and 5B) that recycles light reflected from the skull back to the skull. The light delivered to the tissues in the brain are absorbed and converted into acoustic waves via the photoacoustic effect.

At operation 820, acoustic signals are detected through an acoustic window in the skull using an ultrasonic transducer device while the ultrasonic transducer device is being rotated about one or more rotational axes by the angular scan mechanism. In one implementation, during data acquisition the ultrasonic transducer device rotated through a plurality of rotational positions or scanned between two rotational positions. For example, the ultrasonic transducer device may be rotated between −30 and 30 degrees about a rotation axes. In another example, the ultrasonic transducer device may be rotated between −45 and 45 degrees about a first rotation axis and between −60 and 60 degrees about a second rotation axis. In some cases, the angular scan mechanism may be controlled by a controller and/or other computing device. In one implementation, the controller or other computing device synchronizes system functions by transmitting control signals to the light source(s) to trigger pulses, to the angular scan mechanism to trigger rotational movement, and/or to the data acquisition systems (DAQs) to trigger recording. In another implementation, to synchronize acoustic data acquisition and rotation of the ultrasonic transducer device with light pulses, an external trigger from the light source(s) triggers recording by the data acquisition systems (DAQs) and/or trigger movement of the angular scan mechanism. Some examples of sampling rates include 4 MHz, 8 MHz, 16 MHz, etc.

During an exemplary data acquisition phase, digitized photoacoustic data from the DAQs may be stored in an onboard buffer, and then transmitted to the computing device through e.g., a universal serial bus 2.0 or a universal serial bus 3.0. During the data acquisition phase, photoacoustic data is continuously recorded by the DAQa at a sampling frequency. In one aspect, the sampling frequency is 40 MHz. In another aspect, the sampling frequency may be in a range from 4 MHz to 100 MHz. The one or more data acquisition systems may be set to record photoacoustic data within a particular time period (e.g., 100 µs, 200 µs, or 300 µs) after each illumination e.g., laser pulse excitation. In certain implementations, a TPT system is equipped with a one-to-one mapped signal amplification and data acquisition (DAQ) systems or DAQ circuits to the transducer elements.

At operation 830, the TPT system performs image reconstruction to reconstruct one or more 2D photoacoustic images and/or one or more 3D volumetric photoacoustic images from the acoustic signals detected by the ultrasonic transducer device. In some cases, the recorded photoacoustic data may be retrieved from a computer readable media such as an onboard buffer. Image reconstruction may include, at least in part, implementing an inverse reconstruction algorithm. Some examples of inverse reconstruction algorithms that can be used include: (i) forward-model-based iterative methods, (ii) time-reversal methods, and (iii) universal backprojection (UBP) method. For example, a 3D back projection algorithm can be used to reconstruct a 3D volumetric image or a 2D back projection algorithm can be used to reconstruct a 2D image. An example of a universal backprojection process can be found in Xu, M. And Wang, L., "Universal back-projection algorithm for photoacoustic computed tomography," *Physical Review E* 71, 016706 (2005), which is hereby incorporated by reference in its entirety. Another example of a back-projection process can be found in Anastasio, M. A. et al., "Half-time image reconstruction in thermoacoustic tomography," *IEEE Trans., Med. Imaging* 24, pp 199-210 (2005), which is hereby incorporated by reference in its entirety. In another aspect, a dual-speed-of sound (dual-SOS) photoacoustic reconstruction process may be used. An example of a single-impulse panoramic photoacoustic computed tomography system that employs a dual-SOS photoacoustic reconstruction process is described in U.S patent application 2019/0307334, titled "SINGLE-IMPULSE PANORAMIC PHOTOACOUSTIC COMPUTED TOMOGRAPHY" and filed on May 29, 2019, which is hereby incorporated by reference in its entirety.

At optional operation 840, the TPT system analyzes brain function using the one or more photoacoustic images (e.g., photoacoustic images may be of a region of the cerebral cortex) For example, time traces obtained at each pixel in the photoacoustic images may be extracted. A general linear model (GLM) may be used to find the pixels whose values match the stimulus pattern being applied.

Figure 8:
FIG. 8 depicts a flowchart illustrating operations of a TPT method, according to various embodiments.
Figure 8:
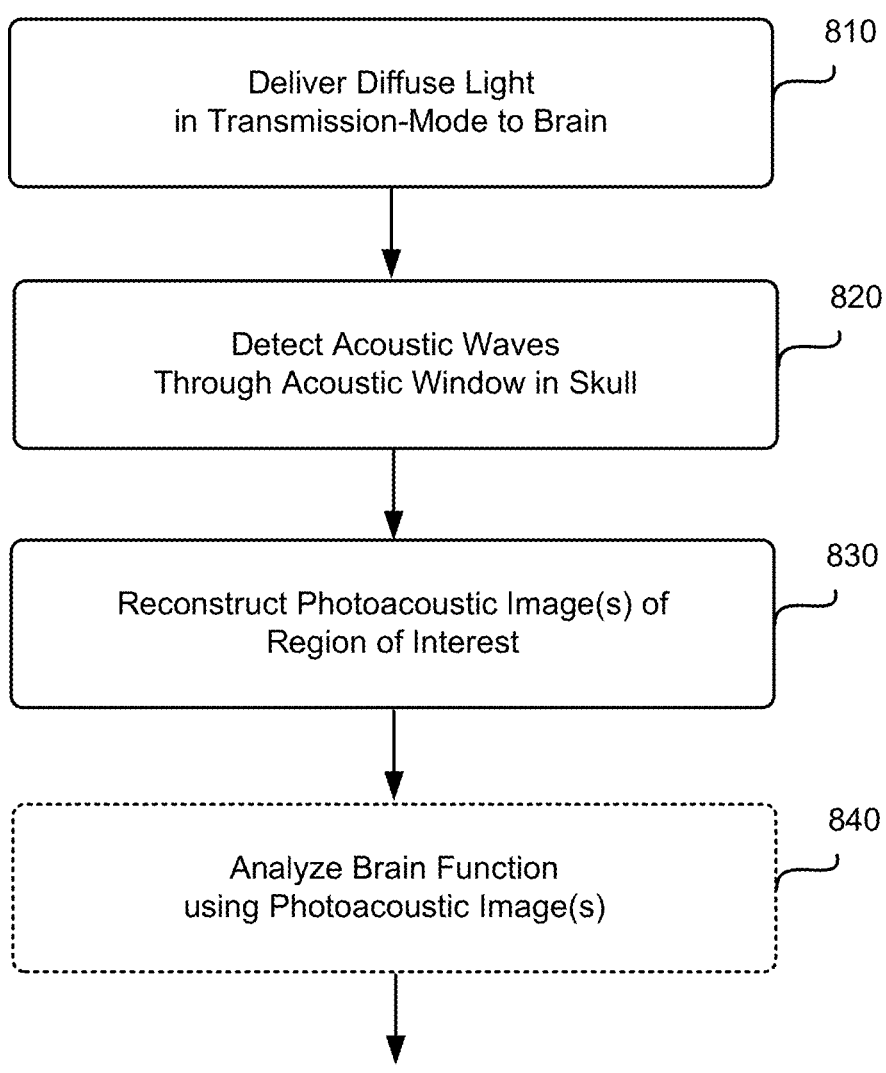
Figure 9:
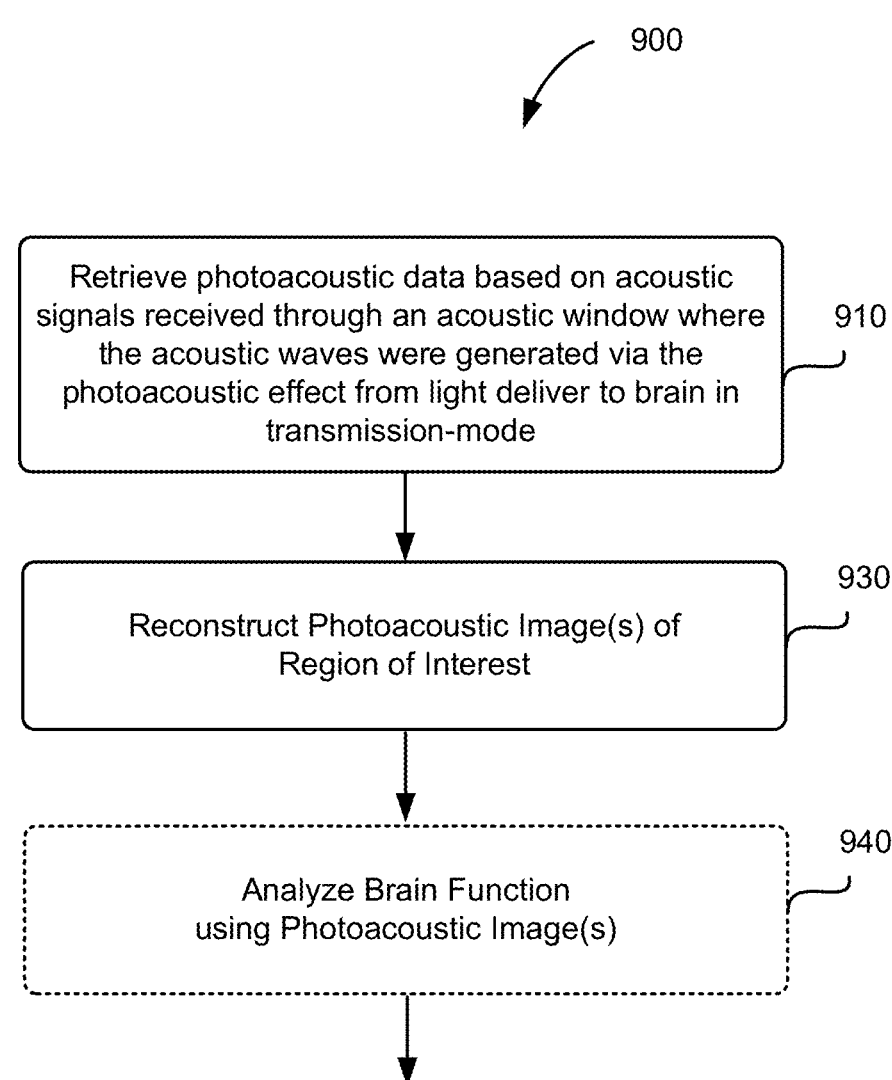
FIG. 9 depicts a flowchart illustrating operations of a TPT method, according to various embodiments.

FIG. 9 is a flowchart depicting a TPT imaging method, according to various implementations. At operation 910, recorded photoacoustic data is retrieved from a computer readable media such as an onboard buffer. The recorded photoacoustic data is generated by performing operations 810 and 820 shown in FIG. 8.

At operation 920, the TPT system performs image reconstruction to reconstruct one or more 2D photoacoustic images and/or one or more 3D volumetric photoacoustic images from the acoustic signals detected by the ultrasonic transducer device. In some cases, the recorded photoacoustic data may be retrieved from a computer readable media such as an onboard buffer. Image reconstruction may include, at least in part, implementing an inverse reconstruction algorithm. Some examples of inverse reconstruction algorithms that can be used include: (i) forward-model-based iterative methods, (ii) time-reversal methods, and (iii) universal backprojection (UBP) method. For example, a 3D back projection algorithm can be used to reconstruct a 3D volumetric image or a 2D back projection algorithm can be used to reconstruct a 2D image.

At optional operation 930, the TPT system analyzes brain function using the one or more photoacoustic images. For example, the one or more photoacoustic images may be of a region of the cerebral cortex.

IV. Demonstrations

A. Phantom Imaging

Three experiments for phantom imaging were performed to study image quality of 3D photoacoustic images of a point target matrix, with and without a skull, to verify that blood signals can be detected by the TPT system through the skull.

The experimental setups used the acoustic detection module 650 shown in FIG. 6A, the light delivery module 410 shown in FIG. 4A, and the data acquisition module 280 shown in FIG. 2. The acoustic detection module includes an ultrasonic transducer device 652 mounted to an angular scan mechanism 654. The ultrasonic transducer device 352 was a linear array ultrasound probe, e.g., ATL P4-2 phased linear array ultrasound probe. The laser source used was a Quantel Qsmart laser.

In the transcranial imaging experiments (A (ii) and A (iii)) below, light was delivered on one side of the skull using a laser articulated arm and the photoacoustic signals were received on the other side of the skull, through the temporal bone. The thinness of the temporal bone and the near-normal incidence of the acoustic waves at the skull reduced the skull-induced aberrations, thus allowing the TPT system to obtain minimally distorted photoacoustic images of a point source matrix through the skull.

(i) Point Source Matrix Imaging Without Skull

In a first experiment, the point source matrix was imaged without a skull. The point target matrix had a 1-inch pitch in a 15 cm×15 cm region. The light delivery module 410 was used to deliver diffuse light to the point source matrix and an ultrasonic transducer device 652 detected acoustic signals while being rotated by the angular scan mechanism 654. The point source matrix was placed at a distance of 15 cm from the ultrasonic transducer probe surface.

Figure 10A:
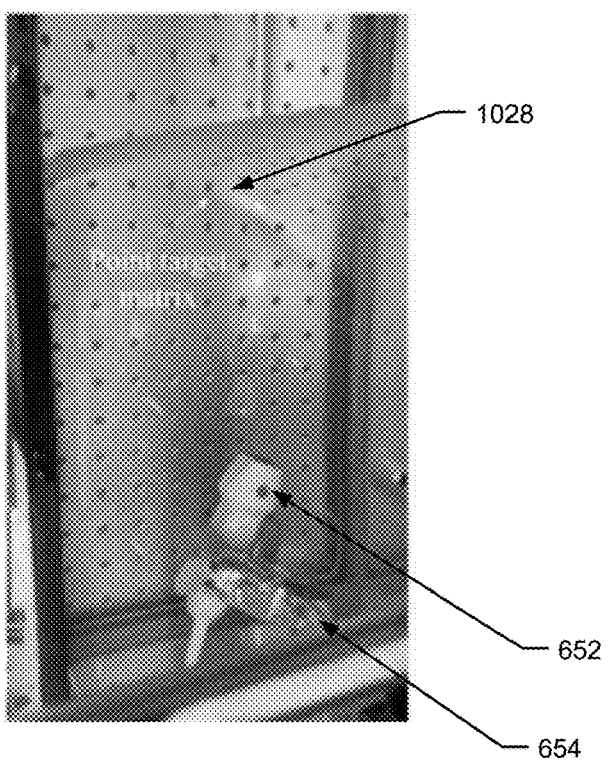
FIG. 10A depicts a photograph of an experimental setup for imaging a point source matrix without a skull, according to an embodiment.
Figure 10B:
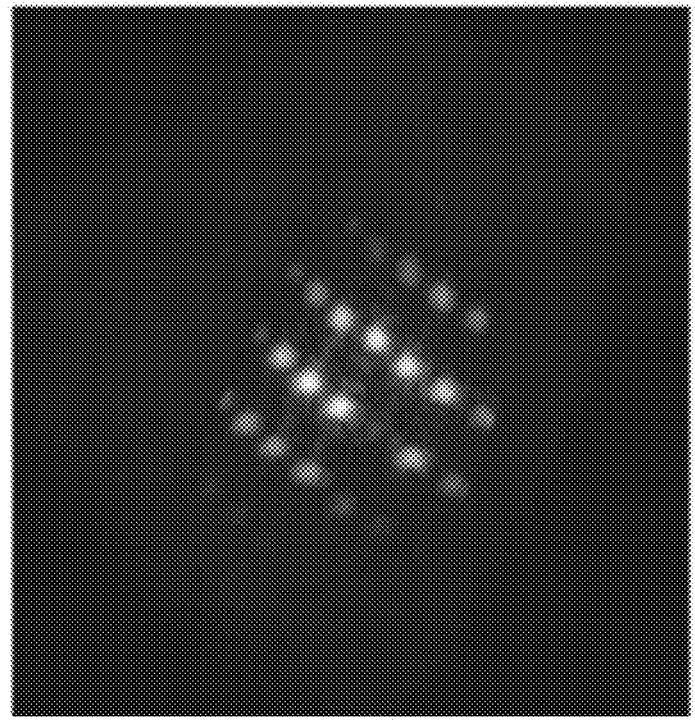
FIG. 10B depicts a 3D volumetric image of the point source matrix being imaged without a skull by the experimental setup in FIG. 10A.

FIG. 10A depicts the experimental setup for imaging a point source matrix without a skull, according to an embodiment. FIG. 10B depicts a reconstructed volumetric image of the point source matrix with a 10 cm×15 cm×15 cm field of view (azimuth×scan×depth).

(ii) Point Source Matrix Imaging Through Skull (Transcranial Imaging)

Figure 11A:
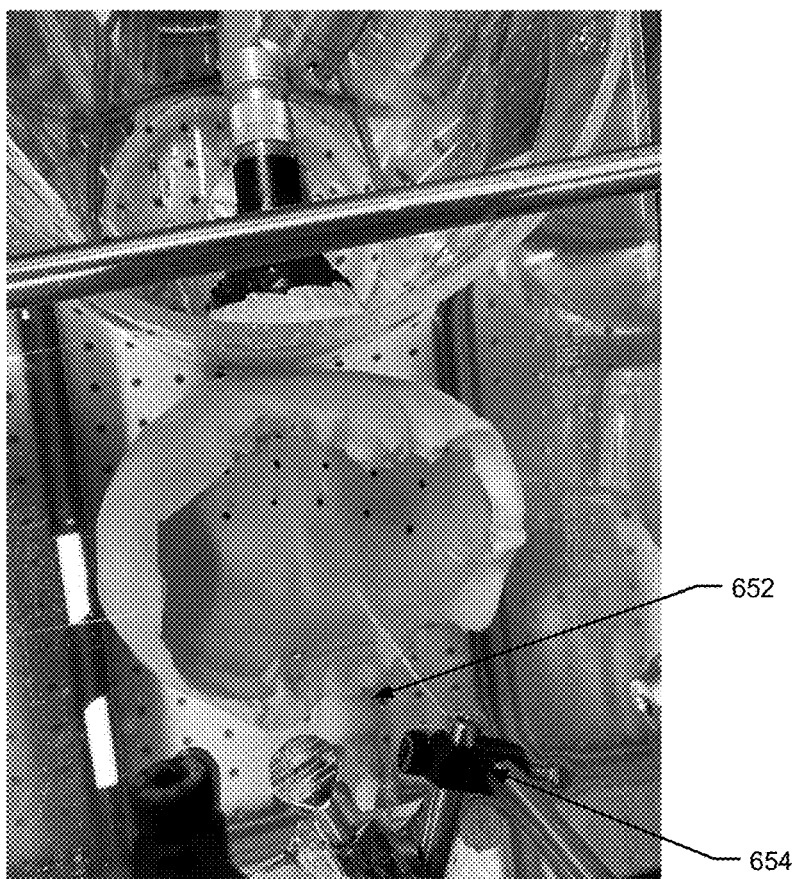
FIG. 11A depicts a photograph of an experimental setup for imaging a point source matrix through the skull, according to an embodiment.
Figure 11B:
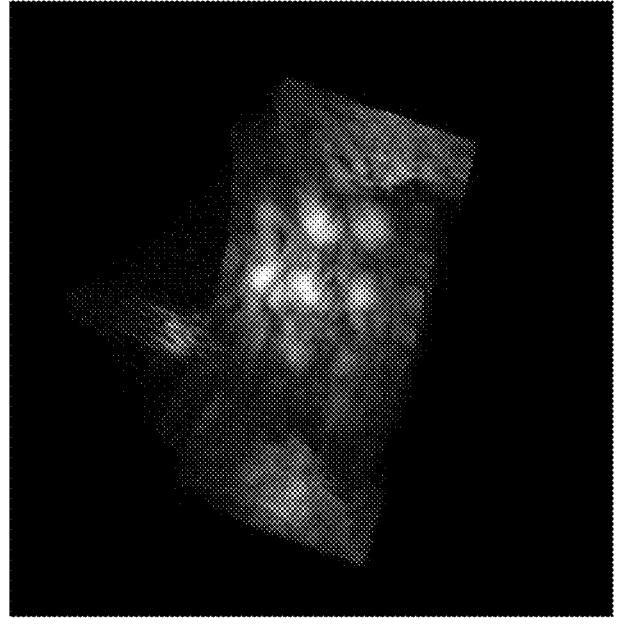
FIG. 11B depicts a 3D volumetric image of the point source matrix being imaged through the skull by the experimental setup in FIG. 11A.

In a second experiment, the point target matrix was imaged through the skull in a 6 cm×6 cm region. FIG. 11A depicts the experimental setup used to image a point source matrix through a skull (transcranial imaging), according to an embodiment. FIG. 11B depicts a 3D volumetric image of the point source matrix being imaged by the experimental setup in FIG. 11A.

The imaging setup closely mimicked the in vivo case, with the ultrasound transducer device 652 placed on the temporal bone and the light delivery module 410 on the other side of the skull. The point target matrix was placed near the inner surface of the skull.

FIG. 10B shows a reconstructed volumetric image of the point source matrix with a 10 cm×15 cm×15 cm field of view (azimuth×scan×depth). The results show that the system components of the experimental setup could clearly resolve the nine-point target matrix in the 6 cm×6 cm region. Results showed transcranial images with reduced skull-induced aberrations. This is because of the thinness of the temporal bone and the near-normal incidence of the acoustic waves at the skull.

(iii) Blood Tube Imaging Through Skull and Muscle (Transcranial Imaging)

Figure 12:
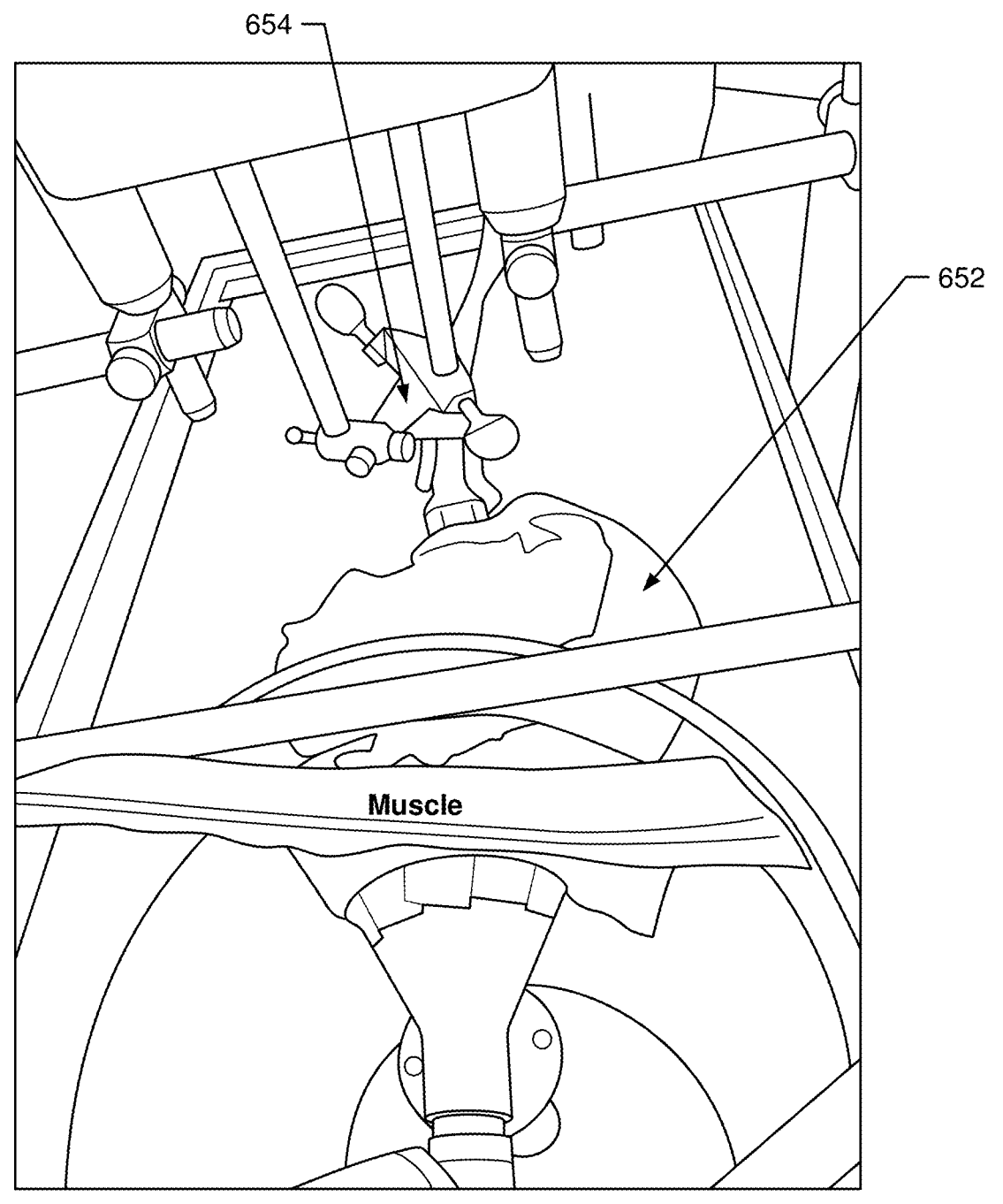
FIG. 12 depicts a photograph of an experimental setup for imaging a blood tube through the skull and 1 cm of muscle, according to an embodiment.
Figure 13A:
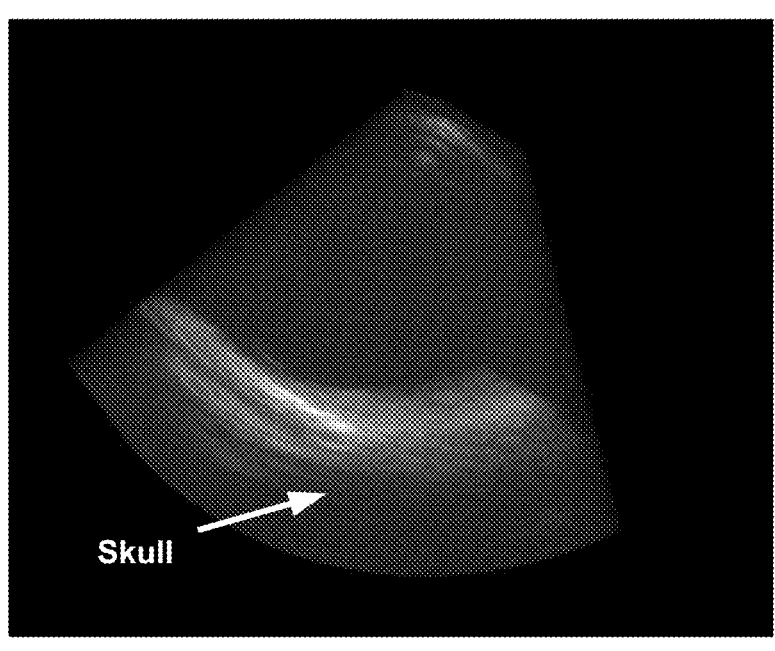
FIG. 13A-B depicts a 3D volumetric image of the target (without/with blood tube) being imaged through the skull and 1 cm of muscle by the experimental setup in FIG. 12A.
Figure 13B:
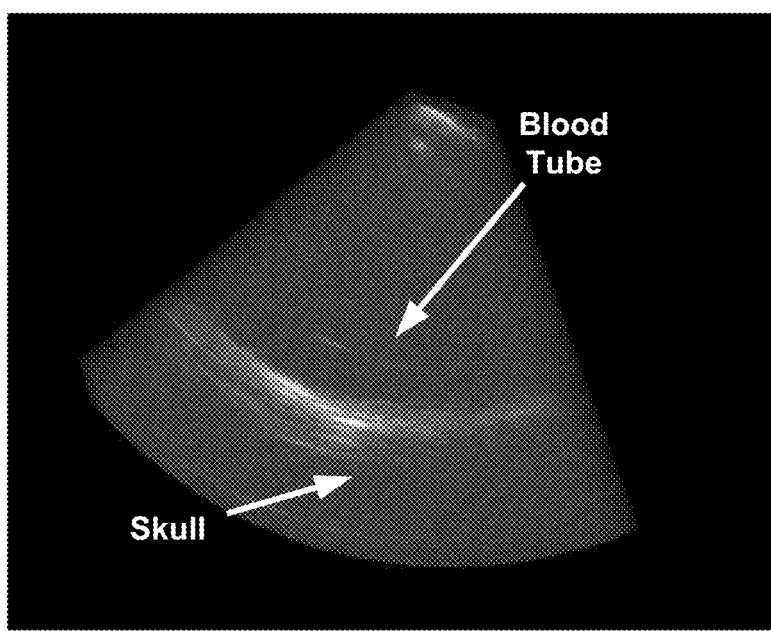

In a third experiment, blood tube signals were detected through the skull and 1 cm of muscle using a setup similar to the transcranial point source target matrix imaging described above. FIG. 12A depicts the experimental setup used for transcranial imaging of a blood tube through the skull and 1 cm of muscle, according to an embodiment. A 1.2 mm diameter blood tube phantom was used. A 1 cm thick slice of muscle was added on the outer surface of the skull, making the setup very close to the in vivo imaging case. Results show that the system can detect the blood tube signals even with light scattering and attenuation through the skull and 1 cm of muscle. These results were obtained without any averaging for each frame.

FIG. 12B depicts a reconstructed volumetric image of the skull only. FIG. 11C depicts a reconstructed volumetric image of the skull and 1 cm of muscle. A comparison of the images in FIGS. 11B and 11C, show that the system was able to detect the acoustic signals from the blood tube despite light attenuation through the skull and 1 cm of muscle, and acoustic attenuation through the temporal bone.

B. In-Vivo Demonstration

The TPT system 300 of the in-vivo imaging configuration shown in FIG. 3 was used to obtain photoacoustic images.

Figure 14A:
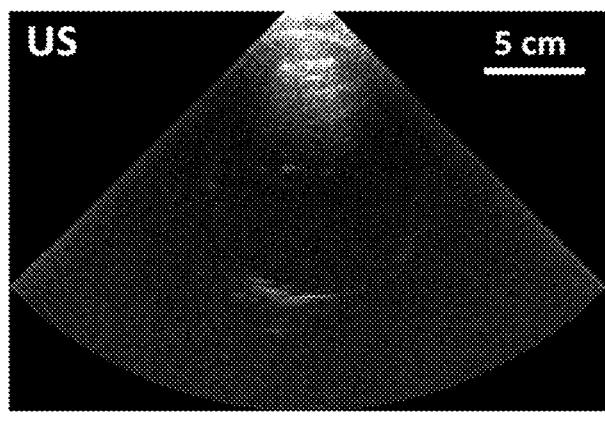
FIG. 14A depicts an ultrasound image of the brain.
Figure 14B:
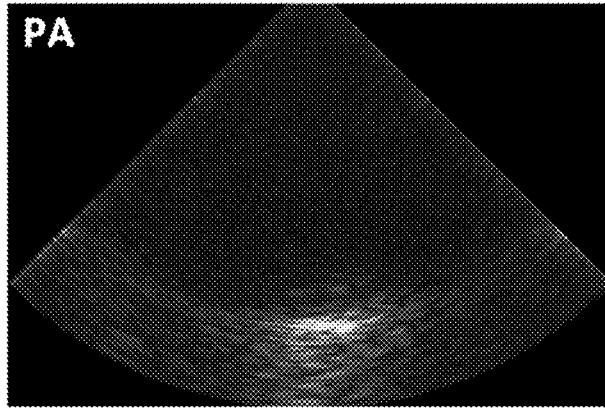
FIG. 14B depicts a photoacoustic image of the brain through the skull in-vivo obtained by the TPT system shown in FIG. 3, according to an embodiment.
Figure 14C:
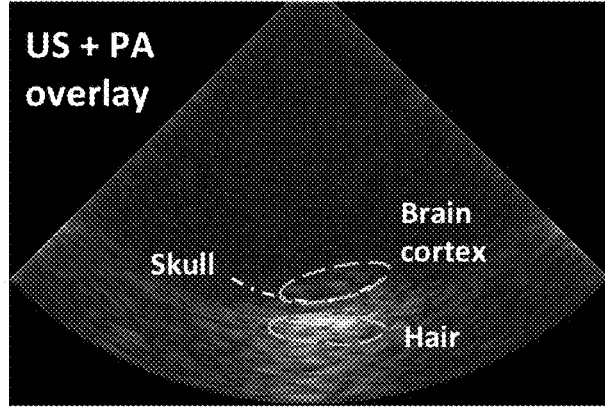
FIG. 14C depicts an overlay of the ultrasound image in FIG. 14A with the photoacoustic image in FIG. 14B, according to an embodiment.
Figure 14D:
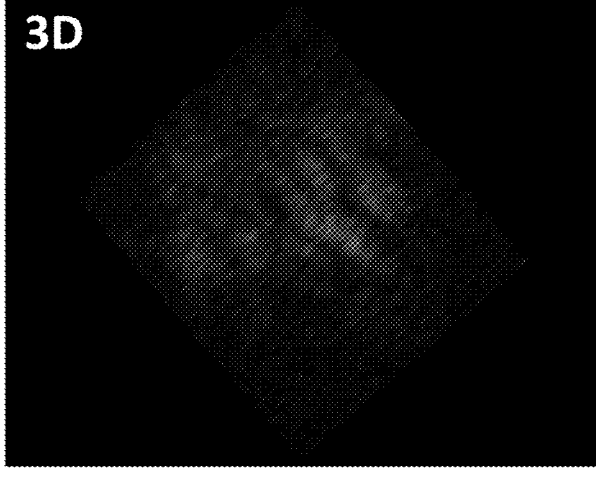
FIG. 14D depicts a 3D photoacoustic image obtained by the TPT system in FIG. 3, according to an embodiment.

FIG. 14A depicts an ultrasound image of the brain. FIG. 14B depicts a photoacoustic image of the brain through the skull in-vivo obtained by the TPT system 300. The skull boundary was extracted from the ultrasound image in FIG. 14A and overlaid with the PA image in FIG. 14B. FIG. 14C depicts the overlay of the ultrasound image in FIG. 14A with the photoacoustic image of the brain through the skull in-vivo in FIG. 14B. This overlay shows that there are features in the photoacoustic image that correspond to the brain cortex. This overlay also shows that the photoacoustic image of the brain obtained by the TPT system was able to image features of the brain cortex. FIG. 14D depicts a 3D photoacoustic image of a 10 cm×10 cm×2 cm field-of-view obtained by the TPT system 300. The 3D image in FIG. 14D shows a vasculature network within the brain.

C. Imaging Human Brain Function

The TPT system 300 of the in-vivo imaging configuration shown in FIG. 3 was used to obtain acoustic photoacoustic images. In this experiment, the human subject performed a tongue tapping task in 4 ON-OFF cycles over five minutes.

Figures 15A, 15B:
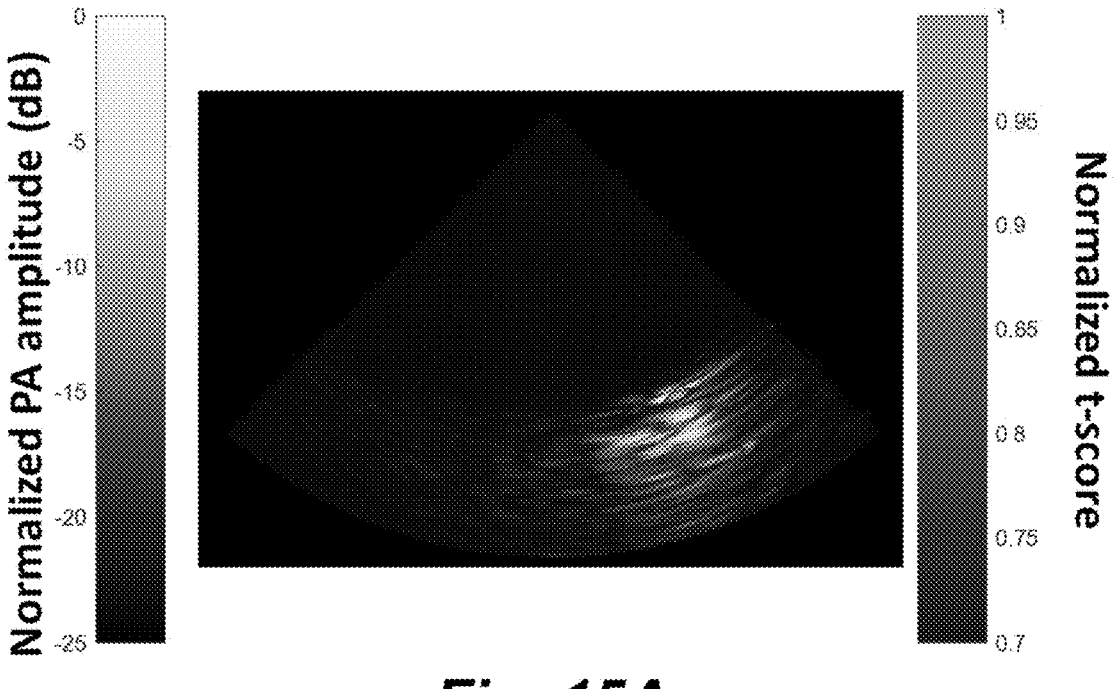
FIG. 15A is an example of a photoacoustic image overlaid with the detected function activity region obtained by the TPT system during the experiment, according to an embodiment.
FIG. 15B is a plot of the percentage change in amplitude over time of the temporal signal correlating to brain function, according to an embodiment.

FIG. 15A is an example of a photoacoustic image obtained by the TPT system 300 during the experiment. The percentage change in amplitude of photoacoustic images over time (temporal signal) was determined from the acoustic signals detected. FIG. 15B is a plot of the percentage change in amplitude over time of the temporal signal. The percentage change in amplitude correlated well with the stimulus pattern of the tongue tapping task. This result shows that the data from a temporal signal can be used to analyze brain function.

Many types of computing devices having any of various computer architectures may be employed as the disclosed systems for implementing algorithms. For example, the computing devices may include software components executing on one or more general purpose processors or specially designed processors such as Application Specific Integrated Circuits (ASICs) or programmable logic devices (e.g., Field Programmable Gate Arrays (FPGAs)). Further, the systems may be implemented on a single device or distributed across multiple devices. The functions of the computational elements may be merged into one another or further split into multiple sub-modules.

At one level a software element is implemented as a set of commands prepared by the programmer/developer. However, the module software that can be executed by the computer hardware is executable code committed to memory using "machine codes" selected from the specific machine language instruction set, or "native instructions," designed into the hardware processor. The machine language instruction set, or native instruction set, is known to, and essentially built into, the hardware processor(s). This is the "language" by which the system and application software communicates with the hardware processors. Each native instruction is a discrete code that is recognized by the processing architecture and that can specify particular registers for arithmetic, addressing, or control functions; particular memory locations or offsets; and particular addressing modes used to interpret operands. More complex operations are built up by combining these simple native instructions, which are executed sequentially, or as otherwise directed by control flow instructions.

The inter-relationship between the executable software instructions and the hardware processor is structural. In other words, the instructions per se are a series of symbols or numeric values. They do not intrinsically convey any information. It is the processor, which by design was pre-configured to interpret the symbols/numeric values, which imparts meaning to the instructions.

The algorithms used herein may be configured to execute on a single machine at a single location, on multiple machines at a single location, or on multiple machines at multiple locations. When multiple machines are employed, the individual machines may be tailored for their particular tasks. For example, operations requiring large blocks of code and/or significant processing capacity may be implemented on large and/or stationary machines.

In addition, certain embodiments relate to tangible and/or non-transitory computer readable media or computer program products that include program instructions and/or data (including data structures) for performing various computer-implemented operations. Examples of computer-readable media include, but are not limited to, memory devices, phase-change devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In some embodiments, code executed during generation or execution of various models on an appropriately programmed system can be embodied in the form of software elements which can be stored in a nonvolatile storage medium (such as optical disk, flash storage device, mobile hard disk, etc.), including a number of instructions for making a computing device (such as personal computers, servers, network equipment, etc.).

In various embodiments, the data or information employed in the disclosed methods and apparatus is provided in an electronic format. Such data or information may include design layouts, fixed parameter values, floated parameter values, feature profiles, metrology results, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

Modifications, additions, or omissions may be made to any of the above-described embodiments without departing from the scope of the disclosure. Any of the embodiments described above may include more, fewer, or other features without departing from the scope of the disclosure. Additionally, the steps of described features may be performed in any suitable order without departing from the scope of the disclosure. Also, one or more features from any embodiment may be combined with one or more features of any other embodiment without departing from the scope of the disclosure. The components of any embodiment may be integrated or separated according to particular needs without departing from the scope of the disclosure.

It should be understood that certain aspects described above can be implemented in the form of logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code using any suitable computer language and/or computational software such as, for example, Java, C, C#, C++ or Python, LabVIEW, Mathematica, or other suitable language/computational software, including low level code, including code written for field programmable gate arrays, for example in VHDL. The code may include software libraries for functions like data acquisition and control, motion control, image acquisition and display, etc. Some or all of the code may also run on a personal computer, single board computer, embedded controller, microcontroller, digital signal processor, field programmable gate array and/or any combination thereof or any similar computation device and/or logic device(s). The software code may be stored as a series of instructions, or commands on a CRM such as a random access memory (RAM), a read only memory (ROM), a magnetic media such as a hard-drive or a floppy disk, or an optical media such as a CD-ROM, or solid stage storage such as a solid state hard drive or removable flash memory device or any suitable storage device. Any such CRM may reside on or within a single computational apparatus, and may be present on or within different computational apparatuses within a system or network. Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

What is claimed is:

1. A photoacoustic imaging method, comprising:

delivering diffuse light in transmission mode through a skull to one side of a region being imaged in a brain;

using an ultrasonic transducer device to detect photoacoustic waves transmitted from an opposing side of the region, the photoacoustic waves received by the ultrasonic transducer device through an acoustic window in the skull, the photoacoustic waves generated based on the diffuse light delivered to the region; and reconstructing a plurality of photoacoustic images of the region based on the photoacoustic waves detected.

2. The photoacoustic imaging method of claim 1, wherein the photoacoustic images are reconstructed using universal back projection.

3. The photoacoustic imaging method of claim 1, wherein the diffuse light has a central axis that intersects the acoustic window.

4. The photoacoustic imaging method of claim 1, wherein the acoustic window is part of (i) a temporal region, (ii) a hemicraniectomy region, (iii) a fontanelle, (iv) a submandibular region, (v) a transorbital region, (vi) or a suboccipital region of the skull.

5. The photoacoustic imaging method of claim 1, further comprising constructing a three-dimensional volumetric image from the plurality of photoacoustic images.

6. The photoacoustic imaging method of claim 1, wherein the region being imaged is at least part of the cerebral cortex of the brain.

7. The photoacoustic imaging method of claim 1, wherein the photoacoustic images are taken over time.

8. The photoacoustic imaging method of claim 7, further comprising imaging a brain function based on the photoacoustic images taken over time.

9. The photoacoustic imaging method of claim 7, further comprising using a photon recycling element to receive light reflected from the skull and reflect the light received to the skull.

10. The photoacoustic imaging method of claim 7, further comprising using an angular scan mechanism to rotate the ultrasonic transducer device such that the plurality of photoacoustic images comprises two-dimensional images taken at different planes of rotation.

11. A photoacoustic imaging method, comprising:
obtaining photoacoustic data recorded by one or more data acquisition devices, wherein the photoacoustic data is based on photoacoustic signals of photoacoustic waves detected by an ultrasonic transducer device, the photoacoustic waves received through an acoustic window in a skull by the ultrasonic transducer device, the photoacoustic waves based on light delivered to a region being imaged in a brain, the light delivered to the brain in transmission mode through the skull to one side of the region in the brain, and the photoacoustic waves transmitted from an opposing side of the region; and
reconstructing a plurality of photoacoustic images of the region based on the photoacoustic waves detected.

12. The photoacoustic imaging method of claim 11, wherein the photoacoustic images are reconstructed using universal back projection.

13. The photoacoustic imaging method of claim 11, further comprising constructing a three dimensional volumetric image from the plurality of photoacoustic images.

14. The photoacoustic imaging method of claim 11, wherein the photoacoustic images are taken over time.

15. The photoacoustic imaging method of claim 14, further comprising imaging a brain function based on the photoacoustic images taken over time.

16. A photoacoustic imaging system, comprising:
a light delivery module comprising a diffuser configured to diffuse a laser beam to produce diffuse light, the light delivery module configured to deliver the diffuse light in transmission mode through a skull to one side of a region being imaged in a brain;
an acoustic detection module comprising an ultrasonic transducer device configured to detect photoacoustic waves transmitted from an opposing side of the region, the photoacoustic waves received by the ultrasonic transducer device through an acoustic window in the skull, the photoacoustic waves based on the diffuse light delivered to the region being imaged; and a data acquisition module comprising one or more data acquisition systems configured to receive acoustic signals from the acoustic detection module.

17. The photoacoustic imaging system of claim 16, wherein the light delivery module is configured to provide the diffuse light in a direction along a central axis that intersects the acoustic window.

18. The photoacoustic imaging system of claim 16, wherein the light delivery module further comprises a photon recycling element configured to receive light reflected from the skull and reflect the light back to the skull.

19. The photoacoustic imaging system of claim 18, wherein the diffuser is disposed within the photon recycling element.

20. The photoacoustic imaging system of claim 16, wherein the light delivery module comprises:
a laser articulating arm configured to propagate a laser beam; and
a diffuser and a photon recycling device coupled to an end of the laser articulating arm.

21. The photoacoustic imaging system of claim 20, wherein the diffuser and the photon recycling device comprise:
a diffuser in optical communication with one or more mirrors of the laser articulating arm to receive the laser beam, the diffuser configured to diffuse the laser beam to generate the diffuse light; and
a photon recycling element configured to receive light reflected from the skull and reflect the light received back to the skull.

22. The photoacoustic imaging system of claim 21, wherein the photon recycling element comprises a housing within which the diffuser is disposed.

23. The photoacoustic imaging system of claim 16, wherein the light delivery module comprises:
a fiber optic bundle having a first end and a second end, the first end in optical communication with one or more laser sources to receive a laser beam; and
a diffuser coupled to an end of the fiber optic bundle to diffuse the laser beam to produce the diffuse light.

24. The photoacoustic imaging system of claim 16, wherein the light delivery module comprises a diffuser in optical communication over free space with one or more laser sources to receive a laser beam, the diffuser configured to diffuse the laser beam to generate the diffuse light.

25. The photoacoustic imaging system of claim 16, wherein the acoustic detection module comprises one or more data acquisition systems.

26. The photoacoustic imaging system of claim 16, wherein the acoustic detection module comprises an ultrasonic transducer device placed in contact with, or in close proximity to, the skull during operation.

27. The photoacoustic imaging system of claim 26, wherein the acoustic detection module further comprises an angular scan mechanism coupled to the ultrasonic transducer device to rotate the ultrasonic transducer device during operation.

\* \* \* \* \*